(12) United States Patent
Hanuka et al.

(10) Patent No.: US 11,291,579 B2
(45) Date of Patent: Apr. 5, 2022

(54) GAS FILTER AND RELEASE FOR OSTOMY APPLIANCE

(71) Applicant: B. Braun Medical SAS, Boulogne-Billancourt (FR)

(72) Inventors: David Hanuka, Ramat-Yishai (IL); Meir Or, Doar-Na Misgav (IL); Refael Sommer, Nesher (IL); Tamir Shavit, Doar-Na Galil Maaravi (IL)

(73) Assignee: B. Braun Medical SAS, Saint-Cloud (FR)

( * ) Notice: Subject to any disclaimer, the term of this patent is extended or adjusted under 35 U.S.C. 154(b) by 646 days.

(21) Appl. No.: 14/889,991

(22) PCT Filed: May 8, 2014

(86) PCT No.: PCT/IL2014/050417
§ 371 (c)(1),
(2) Date: Nov. 9, 2015

(87) PCT Pub. No.: WO2014/181339
PCT Pub. Date: Nov. 13, 2014

(65) Prior Publication Data
US 2016/0166424 A1 Jun. 16, 2016

Related U.S. Application Data

(63) Continuation-in-part of application No. 13/890,433, filed on May 9, 2013, now Pat. No. 9,345,612, and a
(Continued)

(51) Int. Cl.
*A61F 5/441* (2006.01)
*A61F 5/445* (2006.01)
(Continued)

(52) U.S. Cl.
CPC .............. *A61F 5/441* (2013.01); *A61F 5/445* (2013.01); *A61F 5/4405* (2013.01);
(Continued)

(58) Field of Classification Search
CPC combination set(s) only.
See application file for complete search history.

(56) References Cited

U.S. PATENT DOCUMENTS 2,243,529 A 5/1941 Grossman et al.
2,341,984 A 2/1944 Graves
(Continued)

FOREIGN PATENT DOCUMENTS

CN 1694661 A 11/2005
DE 19921555 A1 2/2000
(Continued)

OTHER PUBLICATIONS

International Preliminary Report on Patentability for International Application No. PCT/IL2013/050401, dated Nov. 11, 2014 (10 pages).
(Continued)

*Primary Examiner* — Guy K Townsend
(74) *Attorney, Agent, or Firm* — Clark & Elbing LLP

(57) ABSTRACT

Ostomy appliance components providing filtered release of gasses from a surgical stoma. Filter shape, positioning, and positioning structure relate to potential advantages in manufacturing and operation of components.

19 Claims, 32 Drawing Sheets

Related U.S. Application Data continuation-in-part of application No. PCT/IL2013/050401, filed on May 9, 2013.

(60) Provisional application No. 61/903,523, filed on Nov. 13, 2013, provisional application No. 61/884,256, filed on Sep. 30, 2013.

(51) Int. Cl.
| | |
|---|---|
| *B29C 65/02* | (2006.01) |
| *A61F 5/44* | (2006.01) |
| *A61F 5/448* | (2006.01) |
| *B29L 31/00* | (2006.01) |

(52) U.S. Cl.
CPC ............ *A61F 5/4407* (2013.01); *A61F 5/448* (2013.01); *B29C 65/02* (2013.01); *A61F 2005/4415* (2013.01); *B29L 2031/753* (2013.01)

(56) References Cited

U.S. PATENT DOCUMENTS

| | | | |
|---|---|---|---|
| 2,510,766 A | 6/1950 | Surface | |
| 2,544,579 A | 3/1951 | Ardner | |
| 2,639,710 A | 5/1953 | Fazio | |
| 2,667,167 A | 1/1954 | Raiche | |
| 2,971,510 A | 2/1961 | Berger | |
| 3,398,744 A | 8/1968 | Hooper | |
| 3,447,533 A | 6/1969 | Spicer | |
| 3,718,141 A | 2/1973 | Goetz | |
| 3,976,076 A | 8/1976 | Beach | |
| 4,030,500 A | 6/1977 | Ronnquist | |
| 4,121,589 A | 10/1978 | McDonnell | |
| 4,170,231 A | 10/1979 | Collins | |
| 4,183,357 A | 1/1980 | Bentley et al. | |
| 4,209,010 A | 6/1980 | Ward et al. | |
| 4,210,131 A | 7/1980 | Perlin | |
| 4,211,224 A | 7/1980 | Kubach et al. | |
| 4,217,664 A | 8/1980 | Faso | |
| 4,232,672 A * | 11/1980 | Steer | A61F 5/441 604/333 |
| 4,233,325 A | 11/1980 | Siangan et al. | |
| 4,265,244 A | 5/1981 | Hill | |
| 4,338,937 A | 7/1982 | Lerman | |
| 4,344,434 A | 8/1982 | Robertson | |
| 4,351,322 A | 9/1982 | Prager | |
| 4,381,765 A | 5/1983 | Burton | |
| 4,399,809 A | 8/1983 | Baro et al. | |
| 4,421,124 A | 12/1983 | Marshall | |
| 4,460,363 A * | 7/1984 | Steer | A61F 5/448 604/336 |
| 4,462,510 A * | 7/1984 | Steer | A61M 1/69 222/48 |
| 4,516,974 A | 5/1985 | Davis | |
| 4,534,761 A | 8/1985 | Raible | |
| 4,634,421 A | 1/1987 | Hegemann | |
| 4,642,107 A | 2/1987 | Arnone et al. | |
| 4,662,890 A | 5/1987 | Burton | |
| 4,721,508 A | 1/1988 | Burton | |
| 4,786,283 A | 11/1988 | Andersson | |
| 4,804,375 A | 2/1989 | Robertson | |
| 4,810,250 A | 3/1989 | Ellenberg et al. | |
| 4,834,731 A | 5/1989 | Nowak et al. | |
| 4,854,316 A | 8/1989 | Davis | |
| 4,863,447 A * | 9/1989 | Smith | A61F 5/441 604/335 |
| 4,941,869 A | 7/1990 | D'Amico | |
| 4,950,223 A | 8/1990 | Silvanov | |
| 4,981,465 A | 1/1991 | Ballan et al. | |
| 5,004,464 A | 4/1991 | Leise, Jr. | |
| 5,026,360 A | 6/1991 | Johnsen et al. | |
| 5,045,052 A | 9/1991 | Sans | |
| D323,213 S | 1/1992 | Iacone | |
| 5,108,430 A | 4/1992 | Ravo | |
| 5,125,916 A | 6/1992 | Panebianco et al. | |
| 5,135,519 A | 8/1992 | Helmer | |
| 5,163,897 A | 11/1992 | Persky | |
| 5,163,930 A | 11/1992 | Blum | |
| 5,236,426 A | 8/1993 | Schottes et al. | |
| 5,250,057 A | 10/1993 | Chen | |
| 5,261,898 A | 11/1993 | Polin et al. | |
| 5,269,774 A | 12/1993 | Gray | |
| 5,372,594 A * | 12/1994 | Colacello | A61F 5/441 55/385.4 |
| D354,560 S | 1/1995 | Chase | |
| 5,401,264 A * | 3/1995 | Leise, Jr. | A61F 5/441 604/333 |
| 5,501,678 A | 3/1996 | Olsen | |
| 5,549,588 A | 8/1996 | Johnsen | |
| 5,569,216 A | 10/1996 | Kim | |
| 5,658,266 A | 8/1997 | Colacello et al. | |
| 5,658,267 A | 8/1997 | Colacello et al. | |
| 5,672,163 A * | 9/1997 | Ferreira | A61F 5/441 604/333 |
| 5,683,372 A | 11/1997 | Colacello et al. | |
| 5,693,035 A * | 12/1997 | Leise, Jr | A61F 5/441 604/333 |
| 5,771,590 A | 6/1998 | Colacello et al. | |
| 5,785,677 A | 7/1998 | Auweiler | |
| 5,785,695 A | 7/1998 | Sato et al. | |
| 5,947,942 A | 9/1999 | Galjour | |
| 6,033,390 A * | 3/2000 | von Dyck | A61F 5/441 600/29 |
| D422,357 S | 4/2000 | Niedospial, Jr. et al. | |
| 6,050,982 A | 4/2000 | Wheeler | |
| 6,071,268 A | 6/2000 | Wagner | |
| 6,329,465 B1 | 12/2001 | Takahashi et al. | |
| 6,350,255 B1 | 2/2002 | von Dyck | |
| 6,357,445 B1 | 3/2002 | Shaw | |
| 6,481,589 B2 | 11/2002 | Blomdahl et al. | |
| 6,485,476 B1 * | 11/2002 | von Dyck | A61F 5/441 604/332 |
| 6,543,453 B1 | 4/2003 | Klima et al. | |
| 6,589,222 B1 | 7/2003 | Olsen | |
| 6,595,971 B1 | 7/2003 | von Dyck et al. | |
| 6,659,988 B1 | 12/2003 | Steer et al. | |
| 6,689,111 B2 | 2/2004 | Mulhauser et al. | |
| 6,695,825 B2 | 2/2004 | Castles | |
| 6,723,079 B2 | 4/2004 | Cline | |
| 6,963,772 B2 | 11/2005 | Bloom et al. | |
| 7,001,367 B2 | 2/2006 | Arkinstall | |
| D516,714 S | 3/2006 | McAllister et al. | |
| 7,083,569 B2 | 8/2006 | Boulanger et al. | |
| 7,087,041 B2 * | 8/2006 | von Dyck | A61F 5/442 604/332 |
| 7,250,040 B2 | 7/2007 | Andersen | |
| 7,258,661 B2 * | 8/2007 | Davies | A61F 5/445 600/32 |
| 7,314,443 B2 | 1/2008 | Jordan et al. | |
| 7,582,072 B2 | 9/2009 | McMichael | |
| 7,628,767 B1 | 12/2009 | Simmons et al. | |
| 7,670,289 B1 | 3/2010 | McCall | |
| 7,704,240 B2 | 4/2010 | Buhl | |
| 7,722,586 B2 | 5/2010 | Mullejans et al. | |
| 7,857,796 B2 | 12/2010 | Cline et al. | |
| 7,867,207 B2 | 1/2011 | Therkelsen et al. | |
| 7,946,417 B2 | 5/2011 | Plishka et al. | |
| 7,976,522 B2 | 7/2011 | Hansen et al. | |
| 8,070,737 B2 * | 12/2011 | Cline | A61F 5/445 604/338 |
| 8,092,437 B2 | 1/2012 | Cline | |
| 8,100,875 B2 | 1/2012 | Cline et al. | |
| 8,142,406 B2 | 3/2012 | Blum | |
| 8,217,221 B2 * | 7/2012 | Davies | A61F 5/445 604/378 |
| 8,372,015 B2 | 2/2013 | Escutia et al. | |
| 8,388,586 B2 | 3/2013 | Weig | |
| D685,094 S | 6/2013 | Green et al. | |
| 8,460,259 B2 | 6/2013 | Tsai | |
| D687,144 S | 7/2013 | Gronberg | |
| 8,657,799 B2 | 2/2014 | Carrubba | |
| 8,690,848 B2 | 4/2014 | Cason | |

(56) References Cited

U.S. PATENT DOCUMENTS

| | | | |
|---|---|---|---|
| D710,977 S | 8/2014 | Chen | |
| 8,821,464 B2 | 9/2014 | Hanuka et al. | |
| 8,821,465 B2 | 9/2014 | Hanuka et al. | |
| 8,845,607 B2 | 9/2014 | Hanuka et al. | |
| 8,858,519 B2 | 10/2014 | Hanuka et al. | |
| 8,864,729 B2 | 10/2014 | Hanuka et al. | |
| 8,900,116 B2 | 12/2014 | Hanuka et al. | |
| 8,998,862 B2 | 4/2015 | Hanuka et al. | |
| D728,759 S | 5/2015 | Gonzalez | |
| D739,012 S | 9/2015 | Hanuka et al. | |
| D739,525 S | 9/2015 | Hanuka et al. | |
| D741,996 S | 10/2015 | Strong et al. | |
| D743,552 S | 11/2015 | Bronnimann et al. | |
| 9,314,365 B2 | 4/2016 | Hanuka et al. | |
| 9,345,612 B2 | 5/2016 | Hanuka et al. | |
| 9,517,157 B2 | 12/2016 | Hanuka et al. | |
| D783,814 S | 4/2017 | Hanuka et al. | |
| D796,029 S | 8/2017 | Hanuka et al. | |
| 9,801,754 B2 | 10/2017 | Masters et al. | |
| 9,883,964 B2 | 2/2018 | Hanuka et al. | |
| 9,987,160 B2 | 6/2018 | Hanuka et al. | |
| 10,524,953 B2 | 1/2020 | Hanuka et al. | |
| 10,537,461 B2 | 1/2020 | Hanuka et al. | |
| 2002/0077611 A1* | 6/2002 | von Dyck | A61F 5/445 604/333 |
| 2003/0004477 A1 | 1/2003 | Nielsen et al. | |
| 2003/0150050 A1 | 8/2003 | Tanaka et al. | |
| 2003/0187393 A1* | 10/2003 | Cline | A61F 5/448 604/131 |
| 2003/0199783 A1 | 10/2003 | Bloom et al. | |
| 2003/0220621 A1 | 11/2003 | Arkinstall | |
| 2004/0029467 A1 | 2/2004 | Lacroix | |
| 2004/0073179 A1 | 4/2004 | Andersen | |
| 2004/0122527 A1 | 6/2004 | Imran | |
| 2004/0167376 A1 | 8/2004 | Peters et al. | |
| 2004/0171999 A1 | 9/2004 | Andersen et al. | |
| 2004/0181197 A1 | 9/2004 | Cline | |
| 2004/0193122 A1 | 9/2004 | Cline et al. | |
| 2005/0027159 A1 | 2/2005 | Feng et al. | |
| 2005/0054996 A1 | 3/2005 | Gregory | |
| 2005/0065488 A1 | 3/2005 | Elliott | |
| 2005/0104457 A1 | 5/2005 | Jordan et al. | |
| 2005/0115857 A1 | 6/2005 | Homann | |
| 2005/0175665 A1* | 8/2005 | Hunter | A61K 45/06 424/423 |
| 2005/0186244 A1* | 8/2005 | Hunter | A61P 35/00 424/423 |
| 2005/0187140 A1* | 8/2005 | Hunter | A61L 31/16 424/423 |
| 2005/0196421 A1* | 9/2005 | Hunter | A61L 31/16 424/423 |
| 2005/0208095 A1* | 9/2005 | Hunter | A61L 27/54 424/423 |
| 2006/0048283 A1 | 3/2006 | Sorensen | |
| 2006/0058576 A1* | 3/2006 | Davies | A61F 5/445 600/32 |
| 2006/0106354 A1 | 5/2006 | Vantroostenberghe | |
| 2006/0111682 A1* | 5/2006 | Schena | A61F 5/4407 604/334 |
| 2006/0206069 A1 | 9/2006 | Cline | |
| 2006/0229596 A1 | 10/2006 | Weiser et al. | |
| 2007/0049878 A1 | 3/2007 | Kim et al. | |
| 2007/0088300 A1 | 4/2007 | Cline et al. | |
| 2007/0123832 A1* | 5/2007 | Cline | A61F 5/445 604/335 |
| 2007/0129695 A1 | 6/2007 | Blum | |
| 2007/0142780 A1 | 6/2007 | Van Lue | |
| 2007/0191794 A1* | 8/2007 | Cline | A61F 5/445 604/335 |
| 2007/0219532 A1 | 9/2007 | Karpowicz et al. | |
| 2007/0260206 A1 | 11/2007 | Mullejans et al. | |
| 2007/0276346 A1 | 11/2007 | Poulsen et al. | |
| 2008/0004580 A1 | 1/2008 | Mullejans et al. | |
| 2008/0015405 A1* | 1/2008 | Davies | A61F 5/445 600/32 |
| 2008/0033380 A1 | 2/2008 | Andersen | |
| 2008/0091154 A1 | 4/2008 | Botten | |
| 2008/0108862 A1 | 5/2008 | Jordan et al. | |
| 2008/0135044 A1 | 6/2008 | Freitag et al. | |
| 2008/0269698 A1* | 10/2008 | Alexander | A61F 5/445 604/332 |
| 2008/0275410 A1 | 11/2008 | Burt | |
| 2009/0043151 A1 | 2/2009 | Gobel | |
| 2009/0076532 A1 | 3/2009 | Rebuffat et al. | |
| 2009/0138030 A1 | 5/2009 | Gronberg | |
| 2009/0216206 A1 | 8/2009 | Nishtala et al. | |
| 2009/0247969 A1 | 10/2009 | Nishtala et al. | |
| 2010/0069859 A1* | 3/2010 | Weig | A61F 2/0027 604/335 |
| 2010/0174253 A1 | 7/2010 | Cline et al. | |
| 2010/0241092 A1* | 9/2010 | Nguyen-Demary | A61P 31/00 604/336 |
| 2011/0015475 A1 | 1/2011 | Hanuka et al. | |
| 2011/0040231 A1 | 2/2011 | Gregory | |
| 2011/0040269 A1* | 2/2011 | Cline | A61F 5/4407 604/335 |
| 2011/0106032 A1 | 5/2011 | Kratky | |
| 2012/0059341 A1 | 3/2012 | Masters | |
| 2012/0109086 A1 | 5/2012 | Tsai | |
| 2012/0136324 A1 | 5/2012 | Hanuka et al. | |
| 2012/0179124 A1* | 7/2012 | Nguyen-Demary | A61F 5/445 604/333 |
| 2012/0215188 A1* | 8/2012 | Salama | A61F 5/448 604/335 |
| 2012/0245535 A1 | 9/2012 | Jacobsson et al. | |
| 2013/0053802 A1* | 2/2013 | Maidl | A61F 5/445 604/332 |
| 2013/0053803 A1 | 2/2013 | Willoughby et al. | |
| 2013/0060212 A1 | 3/2013 | Hanuka et al. | |
| 2013/0060213 A1 | 3/2013 | Hanuka et al. | |
| 2013/0060214 A1 | 3/2013 | Willoughby et al. | |
| 2013/0072886 A1* | 3/2013 | Schertiger | A61F 5/445 604/333 |
| 2013/0079736 A1 | 3/2013 | Hanuka et al. | |
| 2013/0079737 A1 | 3/2013 | Hanuka et al. | |
| 2013/0079738 A1 | 3/2013 | Hanuka et al. | |
| 2013/0116642 A1 | 5/2013 | Hanuka et al. | |
| 2013/0304008 A1* | 11/2013 | Hanuka | A61F 5/448 604/334 |
| 2014/0148770 A1 | 5/2014 | Masters et al. | |
| 2014/0194844 A1 | 7/2014 | Edvardsen et al. | |
| 2015/0025488 A1 | 1/2015 | Hanuka et al. | |
| 2015/0057626 A1 | 2/2015 | Hanuka et al. | |
| 2015/0141944 A1 | 5/2015 | Hanuka et al. | |
| 2015/0305916 A1 | 10/2015 | Hanuka et al. | |
| 2015/0359657 A1 | 12/2015 | Argent et al. | |
| 2015/0359658 A1 | 12/2015 | Leise, Jr. | |
| 2016/0113810 A1* | 4/2016 | Hanuka | A61F 5/4401 604/333 |
| 2016/0166424 A1* | 6/2016 | Hanuka | A61F 5/448 604/333 |
| 2017/0143533 A1* | 5/2017 | Schertiger | A61F 5/441 |

FOREIGN PATENT DOCUMENTS

| | | | |
|---|---|---|---|
| DE | 102004001631 A1 | 8/2004 | |
| DE | 102007062133 B3 | 7/2009 | |
| DK | WO 2011057635 A1 * | 5/2011 | A61F 5/441 |
| EP | 1795157 A2 | 6/2007 | |
| EP | 2027835 A1 | 2/2009 | |
| FR | 2870112 A1 | 11/2005 | |
| GB | 2094153 A | 9/1982 | |
| JP | 2006-314479 A | 11/2006 | |
| JP | 2008-507308 A | 3/2008 | |
| WO | WO-87/03192 A1 | 6/1987 | |
| WO | WO-90/07311 A1 | 7/1990 | |
| WO | WO-96/32904 A1 | 10/1996 | |
| WO | WO-99/43277 A1 | 9/1999 | |
| WO | WO-01/49224 A1 | 7/2001 | |
| WO | WO-02/058603 A1 | 8/2002 | |
| WO | WO-03/065945 A1 | 8/2003 | |

(56) References Cited

FOREIGN PATENT DOCUMENTS

| WO | WO-03/071997 | A1 | 9/2003 | |
|----|----|----|----|----|
| WO | WO-2006/010556 | A1 | 2/2006 | |
| WO | WO-2007/030703 | A2 | 3/2007 | |
| WO | WO 2007030703 | A2 * | 3/2007 | ............ A61F 5/441 |
| WO | WO-2008/048856 | A2 | 4/2008 | |
| WO | WO-2008/103789 | A2 | 8/2008 | |
| WO | WO-2008/141180 | A1 | 11/2008 | |
| WO | WO-2009/083183 | A2 | 7/2009 | |
| WO | WO-2009/155537 | A1 | 12/2009 | |
| WO | WO-2011/007355 | A2 | 1/2011 | |
| WO | WO-2011/013872 | A1 | 2/2011 | |
| WO | WO-2011/039517 | A1 | 4/2011 | |
| WO | WO-2011/057635 | A1 | 5/2011 | |
| WO | WO-2011/138727 | A1 | 11/2011 | |
| WO | WO-2011/138728 | A2 | 11/2011 | |
| WO | WO-2011/138730 | A1 | 11/2011 | |
| WO | WO-2011/138731 | A2 | 11/2011 | |
| WO | WO-2013/022487 | A1 | 2/2013 | |
| WO | WO-2013/168165 | A2 | 11/2013 | |
| WO | WO-2014/081889 | A1 | 5/2014 | |
| WO | WO-2014/181338 | A2 | 11/2014 | |
| WO | WO-2014/181339 | A2 | 11/2014 | |

OTHER PUBLICATIONS

International Search Report and Written Opinion for International Application No. PCT/IL2013/050401, dated Dec. 20, 2013 (17 pages).
International Search Report for International Application No. PCT/IL2014/050417, dated Dec. 19, 2014 (7 pages).
Invitation To Pay Additional Fees and, Where Applicable, Protest Fee for International Application No. PCT/IL2013/050401, mailed Sep. 16, 2013 (6 pages).
Written Opinion for International Application No. PCT/IL2014/050417, dated Dec. 19, 2014 (8 pages).
Zhang et al., "Occlusion effect comparison of artificial silicone rubber closure devices with different diameters," Chinese Journal of Tissue Engineering Research. 16(8):1496-1500 (2012). Abstract in English.
U.S. Appl. No. 16/748,466, Hanuka et al.

* cited by examiner

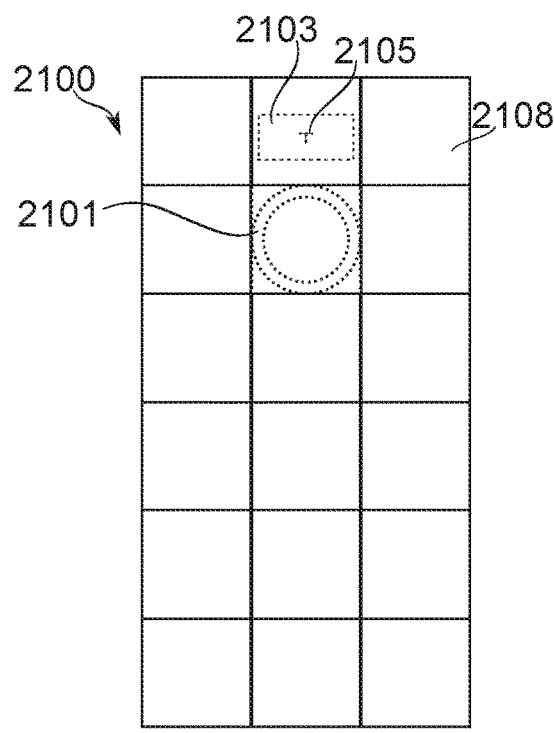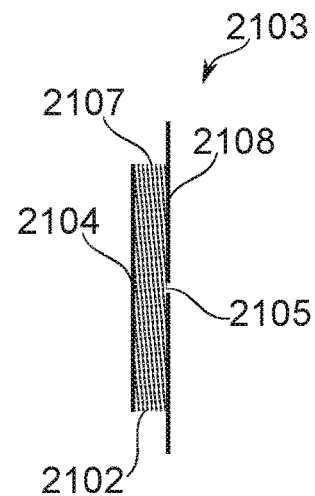
FIG. 17A  FIG. 17B
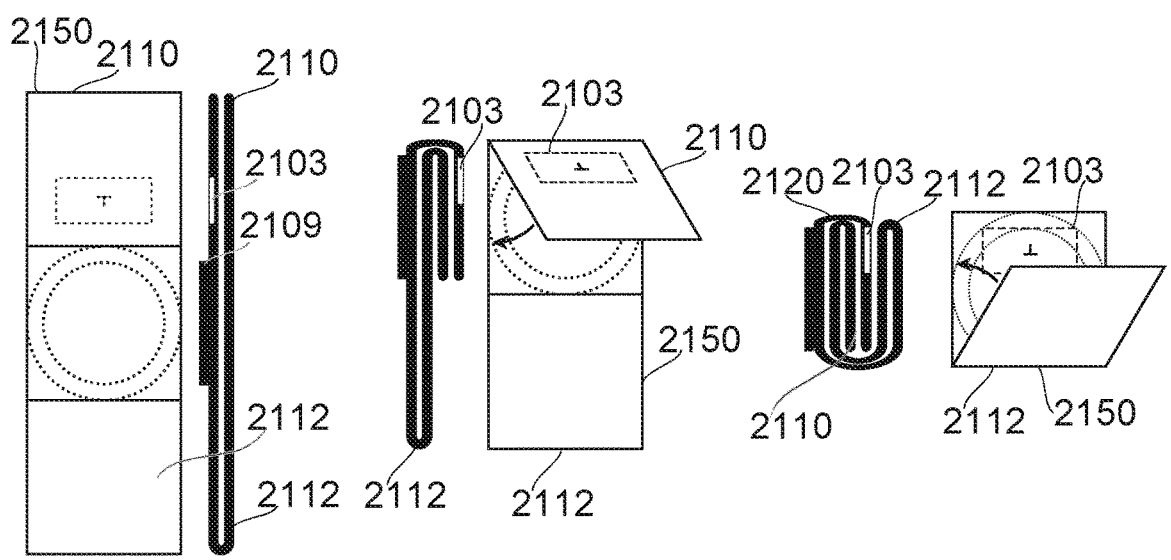
FIG. 17C  FIG. 17D  FIG. 17E

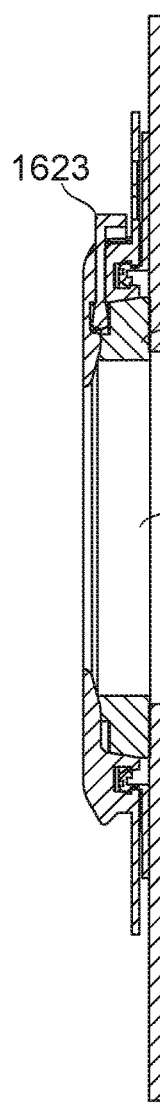
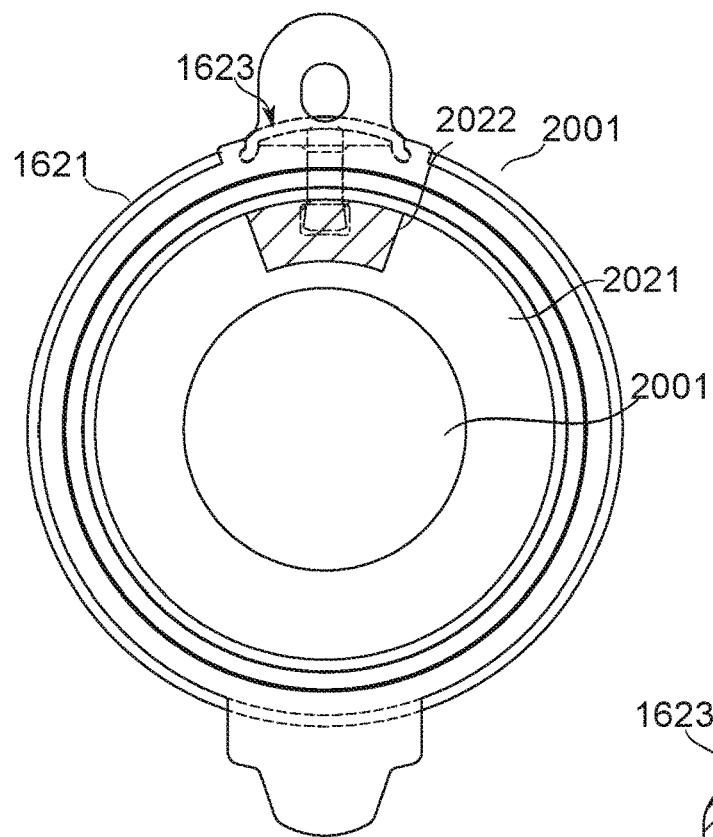
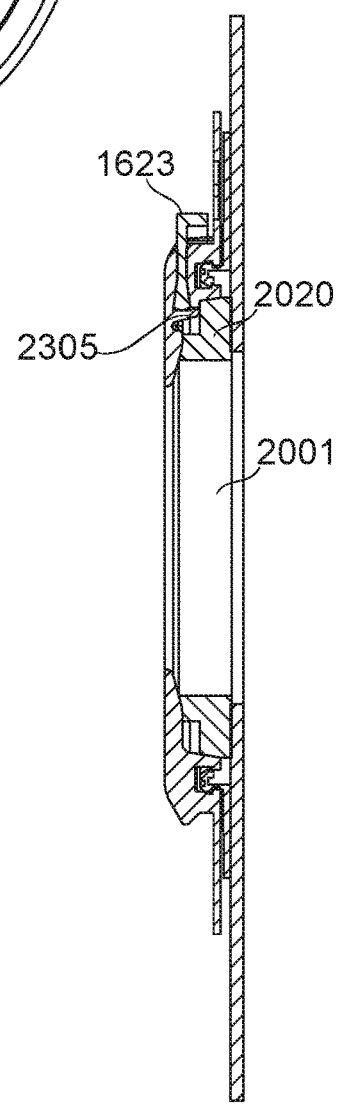
FIG. 20B
FIG. 20A
FIG. 20C

GAS FILTER AND RELEASE FOR OSTOMY APPLIANCE

RELATED APPLICATIONS

This application claims the benefit of priority of U.S. Provisional Patent Application No. 61/903,523 filed Nov. 13, 2013; U.S. Provisional Patent Application No. 61/884,256 filed Sep. 30, 2013; U.S. patent application Ser. No. 13/890,433 filed May 9, 2013; and International Patent Application No. IL2013/050401 filed May 9, 2013; the contents of which are incorporated herein by reference in their entirety.

This application is related to U.S. Provisional Patent Application No. 61/645,118 filed May 10, 2012, the contents of which are incorporated herein by reference in their entirety.

FIELD AND BACKGROUND OF THE INVENTION

The present invention, in some embodiments thereof, relates to the field of medical care for surgically created openings (stoma) in living subjects, and more particularly, to devices and methods for covering a stoma as may be used in the case of a colostomy, ileostomy or urostomy.

In ostomy surgeries, an end or a side of a healthy portion of intestine is surgically attached to a stoma formed in the abdominal wall. Attachment may be to the visceral side, or a surgeon may pass the intestinal portion through the stoma and attach it to the outside of the abdominal wall. Large or small intestine is attached, depending on the type of ostomy.

A stoma may be permanently left in a patient when intestinal content can no longer pass out through the anus, due, for example, to colon cancer, diverticulitis, trauma, or inflammatory bowel disease. A stoma may be temporary, for example, following an operation on a section of bowel requiring a healing period.

Use of an ostomy appliance is indicated for patients with a stoma, to help manage stomal discharge. According to the nature of the stoma, stomal discharge comprises, for example, fecal matter, urine, and/or mucus. Appliances may be wholly external, or at least partially internal. Common elements of ostomy appliances include a pouch for collecting stomal discharge, and a means to seal the pouch over the stoma. In some cases, a plug or cover is used in addition to, or in place of a pouch.

Described ostomy appliance designs include the following:

U.S. Patent Application Publication Number 2007/0191794 relates to "a controlled evacuation ostomy appliance compris[ing] a membrane that is urged into sealing engagement with a stoma, by the generation of radial tension in the membrane. A tensioning device applies tension, with respect to the stoma, at one or more positions that are (i) outboard of the periphery of the projecting portion of the stoma, and/or (ii) between the level of the peristomal skin and the level of the most projecting part of the stoma. Tension limiting means are disclosed. The membrane may be gas-permeable to allow flatus to be vented."

U.S. Patent Application Publication Number 2004/0181197 relates to "a flexible membrane [ . . . ] situated within a rigid or semi-rigid cap. The edge of the cap wall is adhesively fixed to the tissue surrounding the stoma. The interior of the cap is pressurized to press the membrane to seal the stoma against the discharge of solid and semi-solid waste. Gas escapes through a vent with a filter element. The cap can be pressurized by an external pump or an integral pump member situated on top of the cap. A relief valve prevents over pressurization. A collection pouch can be provided as part of a device. The device can be removably mounted on a standard two-piece faceplate."

U.S. Pat. No. 6,689,111 relates to "a balloon-like member [ . . . ] received in the bowel and inflated to seal the stoma. The member includes a thin, flexible wall defining an opening. A rigid or semi-rigid cap retains the member and closes the opening in the member wall. Skin comfortable adhesive adheres the edge of the cap to the tissue surrounding the stoma. A flexible dilation tube facilitates insertion of the member and cooperates with a pump to inflate the member. The cap is preferably removably attached to a standard two-piece ostomy faceplate and is provided with a filter element to vent flatus."

SUMMARY OF THE INVENTION

According to an aspect of some embodiments of the present invention, there is provided an ostomy appliance with a gas release valve, comprising: an ostomy appliance lumenal sidewall forming part of an enclosure for a stoma and having an aperture passing through the sidewall; a valve member crossing most of the way through the sidewall aperture and including: a stopper positioned to block gas outflow through the aperture, and a control member operable from the exterior of the ostomy appliance to unblock the aperture.

According to some embodiments of the invention, the valve member comprises a connecting member connecting the stopper to the control member across the aperture.

According to some embodiments of the invention, the stopper, the control member, and the connecting member are integrally formed.

According to some embodiments of the invention, the connecting member is elastic, and under tension urges the stopper into the blocking position.

According to some embodiments of the invention, the lumenal wall is deformed in compression against the stopper in the blocking position.

According to some embodiments of the invention, the ostomy appliance with a gas release valve comprises a spring in compression urging the stopper into the blocking position.

According to some embodiments of the invention, the ostomy appliance with a gas release valve comprises a spring in tension urging the stopper into the blocking position.

According to some embodiments of the invention, the stopper, the control member, and the spring are integrally formed.

According to some embodiments of the invention, the stopper comprises a filter body providing a portion of a passageway for gas outflow across the lumenal wall, and the blocking position prevents gas outflow passing around the filter body.

According to some embodiments of the invention, the gas outflow is blocked only below a predetermined threshold of a safe interior pressure.

According to some embodiments of the invention, an interior pressure of the ostomy appliance presses against the stopper to move it from the blocking position above a predetermined threshold of pressure.

According to some embodiments of the invention, the predetermined threshold of a safe interior pressure is between 50 mmHg and 100 mmHg.

According to some embodiments of the invention, the blocking position comprises the stopper being pressed against an interior surface of the lumenal wall.

According to some embodiments of the invention, the blocking position comprises the stopper pressed against an exterior surface of the lumenal wall.

According to some embodiments of the invention, the stopper comprises a member extending mostly through the aperture, and operation to move the stopper out of the blocking position comprises a rotation.

According to some embodiments of the invention, the control member comprises an external lever attached to the elongated member, and the lever is operable to rotate the elongated member so that gas is releasable.

According to some embodiments of the invention, the stopper comprises a region flaring toward one end of the valve member, and the blocking position comprises the narrow end of the flared region being at least partially inserted to the aperture, forming a seal therewith.

According to some embodiments of the invention, the stoma is separated from the stopper by a gas-permeable sealing element.

According to some embodiments of the invention, the being separated comprises blockage of solid and liquid waste from reaching the stopper from the stoma.

According to some embodiments of the invention, the lumenal wall comprises a thickness of at least 3 mm through which the connecting member extends.

According to an aspect of some embodiments of the present invention, there is provided an ostomy appliance with a filter element, comprising: a sidewall defining a first lumen enclosing a stoma; and a filter element held in an at least second lumen; the second lumen being an aperture in the sidewall connecting the first lumen to the ostomy appliance exterior.

According to some embodiments of the invention, the wall of the second lumen comprises portions of a base element and a cover element; the filter element contacts both the base element and the cover element; and the base element and the cover element are directly attached to each other on either side of the filter element.

According to some embodiments of the invention, the second lumen comprises a pocket region lined by portions of a base element and a cover element; and the base element and the cover element enclose the filter element within a circumferentially extending pocket closed on at least two circumferential sides.

According to some embodiments of the invention, an end of the first lumen is closed, and the aperture in the sidewall is flush against an interior surface of the closed end.

According to some embodiments of the invention, the cover element inserts into a recess of the base element to form the second lumen.

According to some embodiments of the invention, the filter element is replaceable in the second lumen during operation of the ostomy appliance.

According to some embodiments of the invention, an input channel in fluid communication with an input surface of the filter element separates the input surface from the first lumen.

According to some embodiments of the invention, the input channel comprises a membranous material attached over a base element.

According to some embodiments of the invention, the input channel comprises a recessed surface covered by a closure element to form a lumen.

According to some embodiments of the invention, the input channel comprises hydrophobic surfaces.

According to some embodiments of the invention, the hydrophobic surfaces comprise an aperture small enough to exclude water under pressure of its own weight to the depth of the radius of the first lumen.

According to some embodiments of the invention, the input channel comprises at least one valve between the input surface and the first lumen which closes when a pressure outside the input channel rises relative to a pressure inside the input channel.

According to some embodiments of the invention, the input channel comprises at least one valve between the input surface and the first lumen which opens when a pressure outside the input channel rises relative to a pressure inside the input channel.

According to some embodiments of the invention, the valve is a flutter valve.

According to some embodiments of the invention, the filter element protrudes into the first lumen.

According to some embodiments of the invention, the filter element comprises an open region through which the sidewall base element and cover element directly connect.

According to some embodiments of the invention, the whole input surface by which gas enters the filter element from the first lumen is radially offset from the closest part of the exit surface by which gas leaves the filter element to the exterior.

According to some embodiments of the invention, the second lumen comprises portions of the sidewall molded around the filter element.

According to some embodiments of the invention, the positioning of the filter element does not prevent the flow of waste through the first lumen.

According to some embodiments of the invention, the ostomy appliance with a filter element comprises a waste collection pouch, wherein the first lumen is configured to channel waste to enter the waste collection pouch, and the second lumen provides a channel avoiding the pouch.

According to some embodiments of the invention, the input surface of the filter element on the side of the first lumen extends in one direction at least 5 times the extent of the surface in another direction.

According to some embodiments of the invention, at least one surface of the filter element is laminated.

According to an aspect of some embodiments of the present invention, there is provided a method for manufacturing an ostomy appliance holding a filter element comprising: placing a filter element against an end portion of a sidewall defining a lumen of a first holding part comprised in the ostomy appliance; placing a second holding part against the filter element and the first holding part; and attaching the first and second holding parts together; such that the filter is held between the first and second holding parts.

According to some embodiments of the invention, the attaching is by pressing the first and second holding parts with a welding tool.

According to some embodiments of the invention, the welding tool does not press on at least one of the first and second holding parts over a region of the filter element.

According to some embodiments of the invention, the welding tool presses with reduced pressure on the first and second holding parts over a region of the filter element.

According to some embodiments of the invention, the welding tool does not seal together the first and second holding parts over a region leading to the filter element from the lumen of the first holding part.

According to an aspect of some embodiments of the present invention, there is provided a method for manufacturing an ostomy appliance holding a filter element comprising: placing a second holding part against a sidewall defining a lumen of a first holding part comprised in the ostomy appliance; attaching the first and second holding parts together, leaving therebetween an aperture sized to hold the filter element; and inserting the filter element into the aperture; such that the body of the filter element comprises a principle path of gas conductance through the aperture.

According to some embodiments of the invention, the attaching is by pressing the first and second holding parts with a welding tool.

According to some embodiments of the invention, the welding tool does not press on at least one of the first and second holding parts over a region of the aperture.

According to some embodiments of the invention, the welding tool presses with reduced pressure on the first and second holding parts over a region of the aperture.

According to an aspect of some embodiments of the present invention, including, for example, any of the embodiments described herein, there is provided an ostomy cap for sealing a surgical stoma comprising: an ostomy waste collection pouch, collapsed by crimped folding into a package comprising substantially parallel layers of sub-panels, and having a waste inlet into a first sub-panel; and a filter element, sealed across a break in the material of a second sub-panel of the pouch separated from the first sub-panel by a crimped fold, such that it is configured to receive flatus reaching it from the waste inlet pouch, and vent the flatus to the pouch exterior.

According to some embodiments of the invention, including, for example, any of the embodiments described herein, the first and the second sub-panels are separated by a crease located, when the ostomy cap is worn, above the waste inlet, and above the filter element.

According to some embodiments of the invention, including, for example, any of the embodiments described herein, the side of the second sub-panel to which the filter element is attached is overlaid on the outside of the pouch by a substantially parallel surface pressed thereagainst.

According to some embodiments of the invention, including, for example, any of the embodiments described herein, the crimped fold comprises a region which resists the flow of fluid into the second sub-panel.

According to some embodiments of the invention, including, for example, any of the embodiments described herein, the predetermined pressure level is between 1 mmHg and 10 mmHg.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example, and for purposes of illustrative discussion of embodiments of the invention. In this regard, the description taken with the drawings makes apparent to those skilled in the art how embodiments of the invention may be practiced.

In the drawings:

FIG. 17A schematically shows a filter element positioned to vent through the material of an ostomy pouch, according to some exemplary embodiments of the invention;

FIG. 17B schematically shows structural detail of a filter element, according to some exemplary embodiments of the invention;

FIGS. 17C-17E schematically illustrate positioning of a filter relative to folded structure of an ostomy pouch, according to some exemplary embodiments of the invention;

FIGS. 20A-20C show views of an ostomy appliance comprising a valve protected from stoma waste by a secondary sealing member, according to some exemplary embodiments of the invention.

DESCRIPTION OF SPECIFIC EMBODIMENTS OF THE INVENTION

Figure 1A:
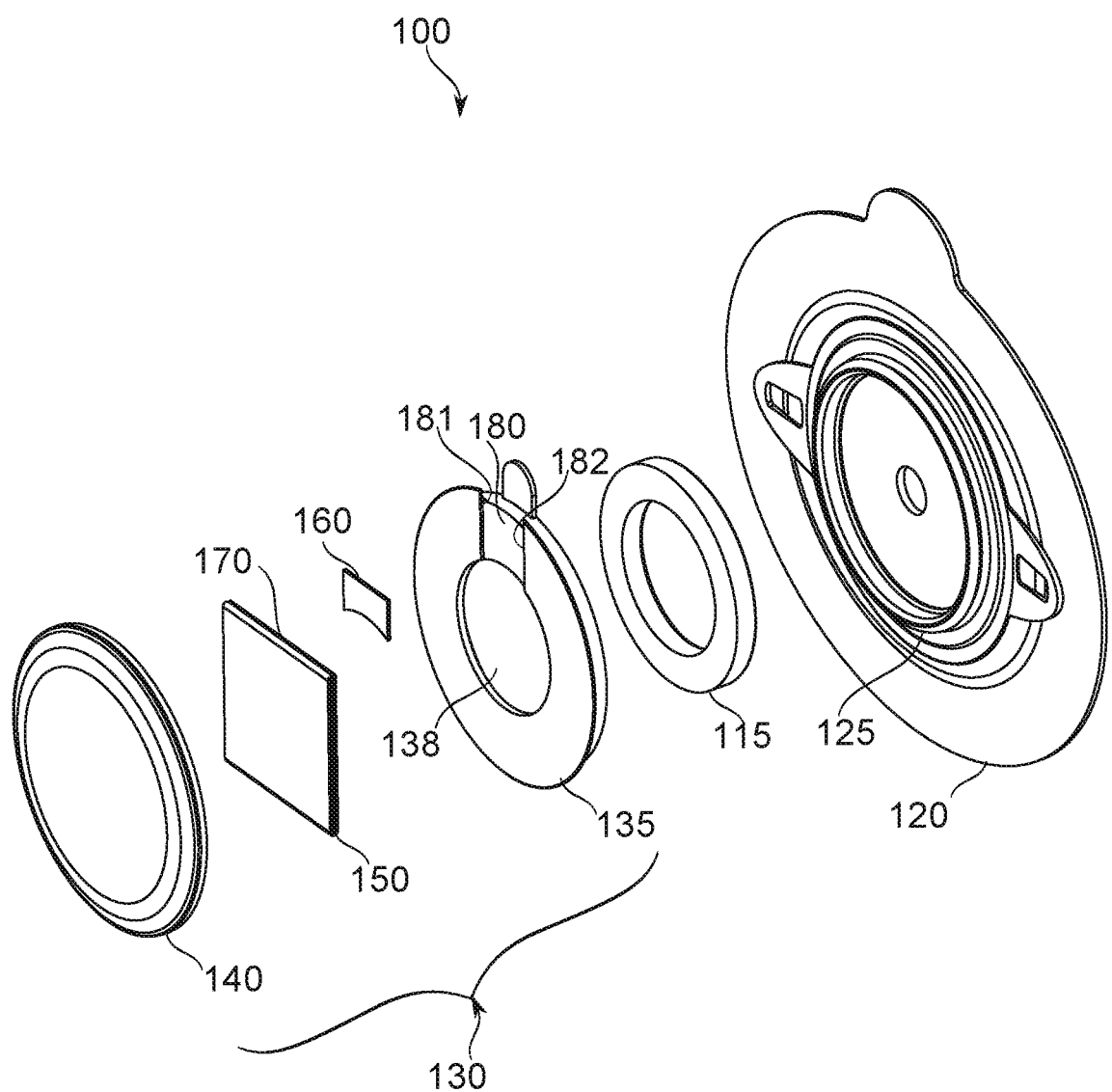
FIG. 1A schematically illustrates an exploded perspective view of an ostomy appliance comprising an integrated gas filter and filter supporting regions, in accordance with some exemplary embodiments of the invention.

The present invention, in some embodiments thereof, relates to the field of medical care for surgically created openings (stoma) in living subjects, and more particularly, to devices and methods for covering a stoma as may be used in the case of a colostomy, ileostomy or urostomy.

Overview

An aspect of some embodiments of the invention relates to the release of stomal gasses through the lumenal sidewall of an ostomy appliance.

In some embodiments, the lumenal sidewall is part of an ostomy appliance which comprises an enclosure for a stoma for controlling the passage of waste therefrom. The enclosure, in some embodiments, comprises a covering for the outer portions of the stoma. In some embodiments of the invention, the lumenal sidewall comprises a passageway for venting pressurized gasses from the digestive tract. Allowing the release of gasses emitted from a covered surgical stoma reduces the internal pressure held by the ostomy appliance. In some embodiments, the gas is filtered in the venting passageway, reducing fecal odors the gas may carry. Additionally or alternatively, slowing gas release through a filter potentially reduces odorant concentrations.

In some embodiments, liquid and/or solid waste are potentially held in the stoma and/or the stoma enclosure during a continent phase of ostomy appliance operation. In some embodiments, liquid and/or solid waste are evacuated to an ostomy pouch during an evacuation phase of ostomy appliance operation. Optionally, to pouch is kept collapsed and closed during the continent phase. Optionally, the pouch is deployed to receive waste. Optionally, a waste-filled pouch continues to be worn until it can be emptied. Optionally, the pouch is not deployed until the ostomate is in a situation which allows the pouch to be immediately emptied and/or replaced.

In some embodiments, the filter element is held within an aperture of a lumenal sidewall of one or more ostomy components. The aperture is formed from, for example, an ostomy cap, adaptor, wafer and/or waste collection pouch. In some embodiments, the aperture walls also guide gas to and/or through the filter element. A potential advantage of filtered release of stomal gasses through the lumenal sidewall of an ostomy appliance is a reduced cost and/or complexity of manufacture for a filter held by components of the ostomy appliance wall.

An aspect of some embodiments of the invention relates to the manufacture of an ostomy appliance which releases gas through a lumenal sidewall.

In some embodiments of the invention, the filter element extends over only a partial thickness and/or circumference of an ostomy appliance wall. Potentially, this reduces manufacturing costs and/or permits joining of walls to strengthen the appliance.

An aspect of some embodiments of the invention relates to providing a filter held between a plurality of supporting layers.

In some embodiments of the invention, an aperture for holding a filter comprises two ostomy components. In some embodiments, the two components form a pocket enclosing the filter element on at least two sides. In some embodiments, the two components are directly bonded to each other. In some embodiments, the aperture comprises a surface of a membranous structure such as a waste collection pouch film. Optionally, the filter is attached into position—for example, welded or adhered—to form a gas-resistant seal around its sides. Additionally or alternatively, a gas-resistant seal is formed by pressing. Optionally, a filter element is removable and/or replaceable while the ostomy components are in service.

An aspect of some embodiments of the invention relates to provision of a thin, flat filter element held within the lumenal sidewall.

In some embodiments, the cross section of the filter element through the lumenal sidewall has an aspect ratio (maximum to minimum crossing length) of 5 to 1 or greater. In some embodiments, the flat filter element is provided with a surface sufficiently flat and extended to receive a laminating membrane which restricts passage of gas therefrom.

An aspect of some embodiments of the invention relates to preserving adequate gas release and/or filtering capacity in a potentially contaminating environment.

In some embodiments, a strainer separates liquid and/or solids from gaseous stomal discharge before discharge reaches a filter element. Potentially, straining input extends the filter element's useful life, by reducing or preventing blockage of gas-receiving surfaces of the filter by liquids and/or solids.

In some embodiments, a strainer comprises patterned attachment of a surface to another surface. The surfaces are, for example, a waste collection pouch film attached to an ostomy component housing. In some embodiments, a single solid element is shaped to hold and/or protect a filter; for example by boring, excavating or molding. Optionally, the shaping of the solid element includes structure for input straining.

In some embodiments, a strainer comprises a gas input aperture is sized to exclude solid and/or liquid waste intrusion. In some embodiments, a plurality of input apertures is provided. In some embodiments, the aperture is distanced from a filter input surface by a channel. In some embodiments, the distancing comprises placing the filter element to the outer edge of the pocket which encloses it. In some embodiments, the channel is completely or partially circumferential. Optionally, the channel provides multiple paths to the filter input surface from one or more strainer input apertures. Optionally, the arrangement of input apertures and/or channels is configured to provide apertures distributed around the circumference.

Optionally, the input aperture is narrow, excluding solid waste by size and/or resisting fluid waste intrusion by surface tension. In some embodiments, strainer surfaces comprise a hydrophobic material. Potentially, hydrophobicity resists the intrusion of fluid waste. In some embodiments, flexible construction allows external pressure to collapse a gas input aperture, closing it against leakage. In some embodiments, external pressure on a gas input aperture opens a normally closed aperture. In some embodiments, the arrangement of input apertures and/or channels is configured with respect to gravity; for example, apertures are placed higher on the ostomy appliance, and/or given additional protection if located lower on the appliance.

In some embodiments of the invention, gas-receiving surface area of the filter element is increased by shaping of the filter element edge. For example, a filter element is shaped with edge irregularities and/or protruding shapes. Potentially, additional gas-receiving area maintains filter function even if surface contamination occurs.

An aspect of some embodiments of the invention relates to valve-controllable gas release.

In some embodiments, a valve for gas release comprises a closeable aperture in the housing sidewall or end cap wall of an ostomy appliance housing. In some embodiments, the valve comprises a member attached to a control such as a lever, handle, or button; the member being configured to enter a gas venting aperture. In some embodiments, the member positions a sealing element that blocks gas release from the aperture, the block being removable by manipulating the control. In some embodiments, the penetrating member itself seals the aperture, but is moveable to deform the aperture and allow gasses to escape. In some embodiments, the valve limits gas release, but allows leakage under at least some pressure conditions, for example as a safety gas release mechanism.

An aspect of some embodiments of the invention relates to the configuration of a filtering element with an ostomy pouch, such that the filter is operable to release gas while the ostomy pouch is collapsed.

In some embodiments of the invention, a filter is placed in a defined region of an ostomy pouch. Optionally, the region is chosen such that it functions when the ostomy pouch is collapsed, for example, folded, more particularly, folded in creased panels, or still more particularly, folded in creased panels comprising a plurality of panels of substantially equivalent in size to the largest panel (for example 80%, 90%, or another fraction of the largest panel size).

In some embodiments of the invention, the pouch being folded comprises having a plurality of substantially parallel panels (regions delimited by pouch boundaries and/or fold boundaries) in the package, the number of panels being, for example, 4, 9, 12, 16, 18, 20, 40, or another larger, smaller, or intermediate number of panels. In some embodiments of the invention, the pouch being folded comprises having a plurality of crease regions, through which the orientation of the pouch material bends by about 180°, the number of creases being, for example, 1, 2, 3, 4, 5, 6, or a larger predefined number of folds. In some embodiments of the invention, one or more crease regions comprise a change in the orientation of the pouch material through about 90°, for example, comprising a box-like configuration, an accordion-like configuration wherein a first set of panels lies perpendicular to another set of panels, or another configuration. In some embodiments, a fold comprises a crimp, such that material of the pouch from opposing plies is pressed together to form a region of sealing. In some embodiments, a crimp comprises a crease in pouch material of sufficient depth and/or permanence that it remains clear upon unfolding of the pouch. In some embodiments, a crimped fold line comprises a natural line along which a pouch does and/or would re-fold from an empty deployed position. In some embodiments, a crimped fold comprises a region which doubles over a ply of pouch material so that it touches itself within a short distance of the crimp, for example, within 0.5-1 mm, 1-2 mm, 2-4 mm, 3-6 mm, or within another range of distances having the same, intermediate, longer, and/or shorter bounds.

In some embodiments, the predefined package is compact, for example, comprising less than 75%, 50%, 25%, or less than a larger, smaller, or intermediate amount of empty space compared to the volume of packaged pouch material. In some embodiments, compactness comprises being under compression relative to a folded but loosely held state, for example, compacted to 95% or less of the loose volume, 80% or less of the loose volume, or having another larger, smaller or intermediate compaction ratio. A pouch package is "compact", in some embodiments, if it lies within a thickness which is not more than 50% greater than the ply thickness alone required, or not more than 25%, 75%, or another greater, lesser, or intermediate package thickness. In an exemplary embodiment, two plies of 60 micron pouch film are used to make a pouch, and the pouch itself is folded in a 3×6 pattern of square panels. The overall thickness of the plies alone is thus about 2160 microns (2.16 mm); 150% of this thickness is about 3.24 mm. Considering compactness from another perspective, an exemplary package is 2 mm thick, fully compressed, but if released again, it springs to twice this thickness (due, for example, to inherent "springiness" of the material, bulking issues around folds, or another reason). In some embodiments, a compression ratio of 75% is reached when the package is reduced to a thickness of 3 mm.

In some embodiments, the relative largest single side surface area of the packaged pouch is less than the open (unfolded or unfurled) single side surface area of the pouch, having a relative surface are of, for example, <5%, <10%, <25%, <50%, <75%, <100%, and/or fraction of the unfolded surface area of the pouch which is intermediate, smaller, or larger.

In some embodiments of the invention, one or more creases between panels functions to restrict the passage of liquid and/or solid waste. In some embodiments, the passage is restricted by crimping of a fold across a crease. In some embodiments, resistance to passage through a fold is maintained by restriction of expansion space by a pouch restraint.

It is a potential advantage to restrict the access of solid and/or liquid waste to a filter, to reduce the occurrence and/or rate of filter blockage. In some embodiments, the filter is overlaid by a membrane that is permeable to gases but impermeable to liquids and solids, potentially reducing production complexity and cost. In some embodiments, flatus passes the one or more creases to reach the filter. In some embodiments of the invention, the filter is placed within a designated panel of the folded ostomy pouch. In some embodiments, the designated panel is located in a panel separated by one crease from an intake aperture of the ostomy bag. In some embodiments, the designated panel is above the intake aperture in the deployed bag. In some embodiments, the designated panel is folded over the region of the intake aperture, such that waste, in order to reach the filter, must flow upward for at least a portion of its journey, for example, upward to reach a crease, then downward; and/or downward, to reach a crease, and then upward. In some embodiments of the invention, separating a filter from the pouch waste inlet by one, two, or more creases slows the progress of liquid and/or solid waste to reach the filter, relative to the progress of gas.

In some embodiments, relative resistance to liquid as opposed to gaseous flow across a crease comprises straining based on the relative viscosities and/or surface tensions of the two material types. In some embodiments, the influence gravity reduces liquid flow through a fold region while gaseous flow is relatively unaffected. In some embodiments of the invention, a greater mobility of gas under pressure allows it to reach and fill voids before liquid. Potentially, this reduces the pressure differential driving the movement of material. In some embodiments, a crease region comprises a narrow channel which resists the flow of liquid along its length more than the flow of gas, for example, due to surface properties of the pouch (such as hydrophobicity) interacting differently with the liquid and the gas.

In some embodiments, the designated panel is chosen to achieve a desired pathway of access of flatus to the filter element from within the folded pouch, for example, across one crease, two creases, three creases, or more. Optionally, the choice of path length is based on a desired relative amount of resistance to flatus passage and/or solid/liquid waste passage. In some embodiments, the designated panel is chosen based on the position of a venting aperture of the filter within the folded stomal waste pouch package. For example, the venting aperture is placed to be positioned on the outermost surface of the package, with access to the exterior after passing directly to an open side of a fold, and/or with access to the exterior after passing around one or more fold regions of the pouch package. It is a potential advantage to arrange the filter so that its exit aperture remains unblocked during wear, even if the pouch becomes partially inflated. In some embodiments, a compartment containing the ostomy waste collection pouch comprises one or more vents to the outer atmosphere, preventing occlusion of the filter by a buildup of back-pressure. For example, a pouch restraint element (such as a cover for an ostomy cap) comprises one or more apertures, and/or one or more regions where attachment to the ostomy appliance is incomplete, and/or permits the passage of gas. In some embodiments, the pathway of access of flatus to the filter element is set such that gas flow through the filter is low, for example no more than 1-10 ml/min, 2-5 ml/min, 3-8 ml/min, or another range of flow rates having the same, intermediate, larger and/or smaller bounds. A low degassing rate provides a potential advantage by enabling more effective filtering. More effective filtering potentially reduces fecal odors and/or enables using less filter material to achieve a given filtering requirement.

In some embodiments of the invention, a filter is placed at a designated position and/or orientation within a panel, for example, at a region of the panel which occupies a higher position when the pouch is in its folded configuration. Positioning at a high point provides a potential advantage for reducing the opportunity for contact with solid and/or liquid waste. In some embodiments of the invention, the filter is placed sufficiently far from creases that it substantially does not interfere with folding: for example, 1-2 mm away, 2-4 mm away, 3-8 mm away, 5-10 mm away, or another distance of separation from a crease. In some embodiments the filter is sized to avoid creases; for example, sized to remain 1-2 mm away, 2-4 mm away, 3-8 mm away, 5-10 mm away, or another distance away from all sides of the folded panel near a crease. In some embodiments, a filter element is placed to cross a crease region. In some embodiments, filter element bulk at a crease region is reduced, for example, by removal of bulk material at the crease, and/or by a notch and/or cut.

This is a potential advantage for preventing pinching of the filter such that its exit aperture is sealed, preventing the exit of gas from the stoma through it. In some embodiments of the invention, the filter is sealed on sides most liable to come into contact with waste, for example, on the side facing the direction from which waste reaches the filter, and/or on sides adjoining that face. This is a potential advantage for avoiding contamination of the filter with waste. Another potential advantage of side-sealing is to allow an exit aperture of the filter to be nearer to one (sealed) edge of the filter, without shortening the minimum path from the filter inlet surface to the filter outlet. Potentially, this allows a longer path, increasing filtering efficacy. Additionally or alternatively, this potentially allows less filter material to be used. Use of less filter material potentially reduces a materials cost, and/or reduces the bulk of the folded pouch package.

In some embodiments of the invention, the overall configuration of the filter, pouch, pouch restraint, and/or other ostomy appliance components is designed to control the rate of filter flow, and/or the pressure at which flow through the filter initiates (effective crack pressure). In some embodiments, the minimum outflow pressure is set to, for example, 1-10 mmHg. In some embodiments, the minimum outflow pressure is, for example, 1-5 mmHg, 3-7 mmHg, 5-10 mmHg, 8-15 mmHg, 12-20 mmHg, 10-50 mmHg, 45-120 mmHg, or another range of pressures having the same, intermediate, higher, and/or lower bounds. In some embodiments of the invention, the outflow pressure is set, for example, by one or more of the characteristics of the filter itself, the topological position of a sub-panel of the pouch to which the filter attaches (for example, across one or more folds, and the tightness of the folds), the folded position of said sub-panel (for example, at the outside of the folded package, or on the inside), the position on a sub-panel that the filter element occupies (for example, near an edge or buried inside a fold), and/or the susceptibility to leakage of a compartment containing the pouch.

A low effective crack pressure and/or high rate of flow is a potential advantage, for example, to reduce physiological bloating, and/or improve the durability of the sealing of the ostomy containment system (for example, sealing of a wafer against skin). A higher effective crack pressure and/or low rate of flow confers a potential advantage by allowing gas to partially pressurize pouch panel segments past the inlet panel, from where it resists pressurized filling with fluids or solids. Potentially, an effective filter life span is thereby increased. In some embodiments, a lower rate of flow allows use of a (potentially less expensive) filter which is less efficient at odor collection, while still providing sufficiently effective odor control. In some embodiments of the invention, the rate of flow through the filter is restricted by a component other than the filter itself, for example, a crimped fold of the pouch, a size and/or a shape of an outlet (exhaust) aperture of the filter, and/or a degree of compression (for example, by the pouch restraint) of the collapsed pouch.

Effective crack pressure and/or flow rate is regulated, in some embodiments, by (for example) the pattern of folding of a pouch, constraining containment placed on the pouch by a pouch restraint, and/or the design and/or positioning of the filter element itself.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Exemplary Ostomy Appliance with Flat Filter

Figure 1B:
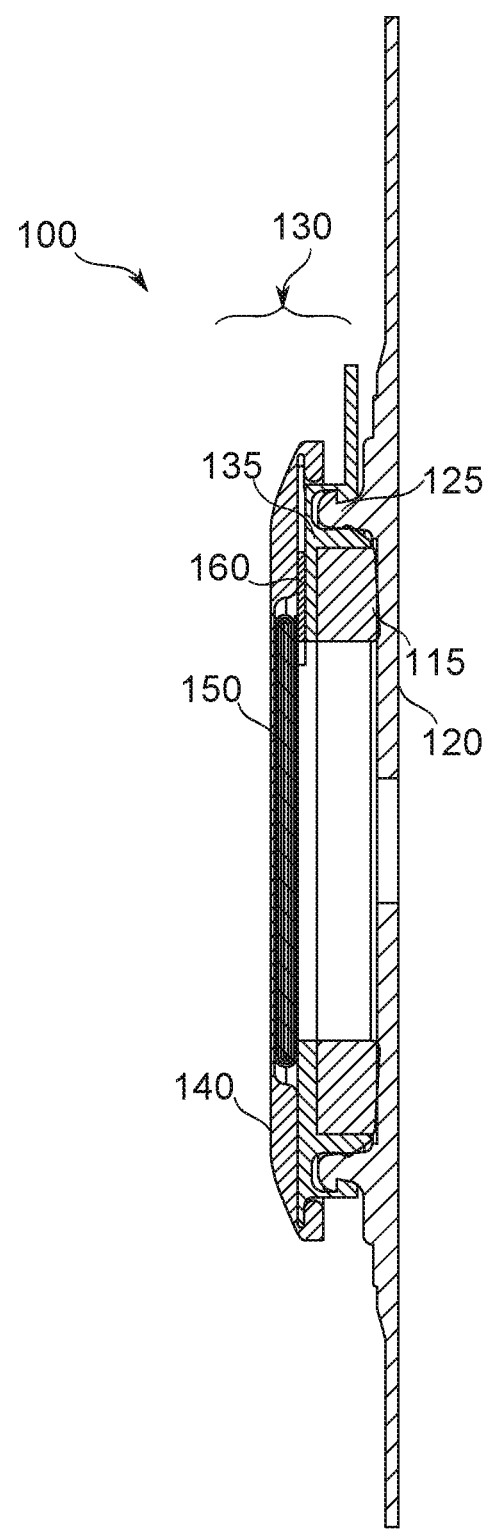
FIG. 1B schematically illustrates a sectional view of the ostomy appliance of FIG. 1A, in accordance with some exemplary embodiments of the invention.
Figure 1C:
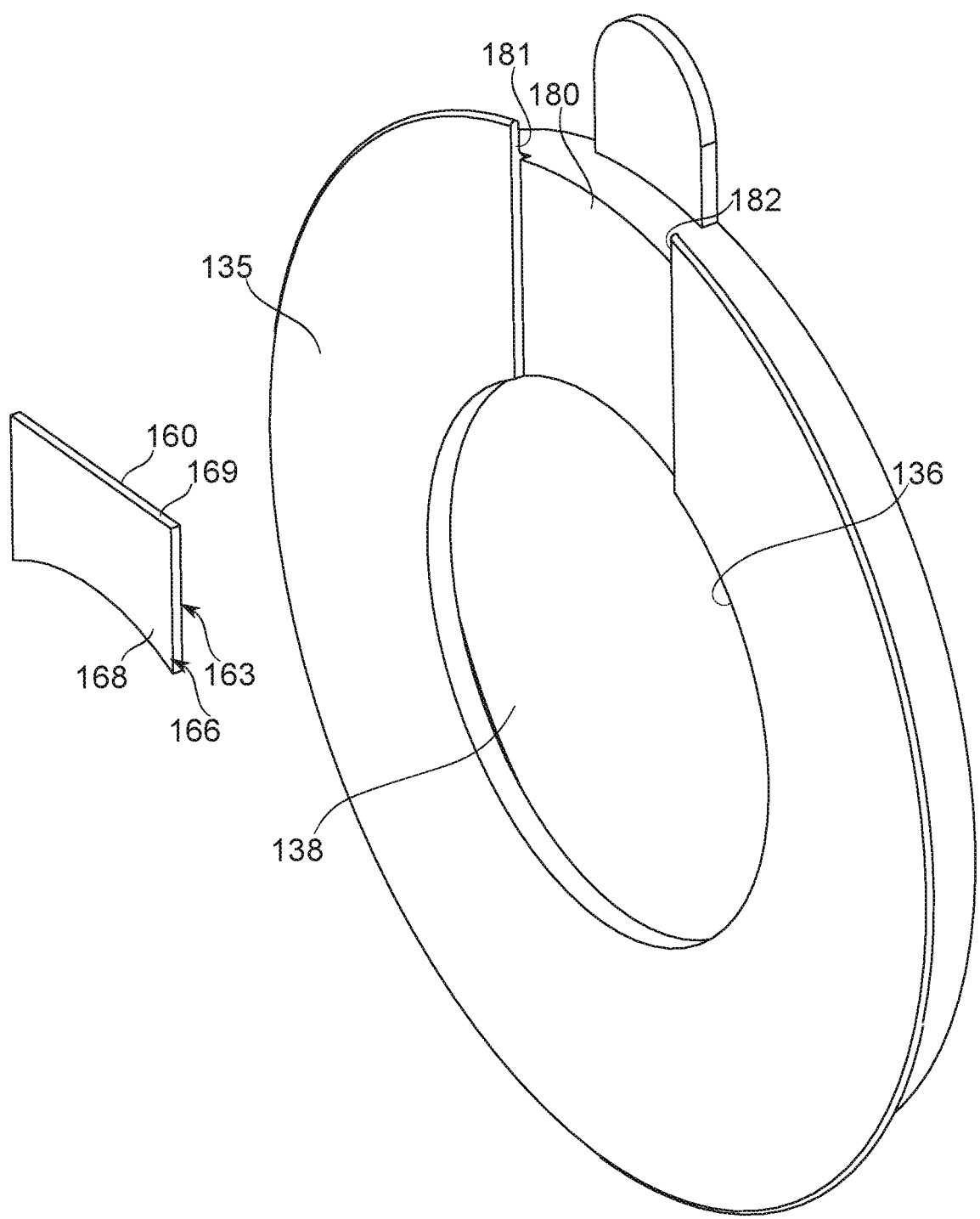
FIG. 1C shows the gas filter and cap housing of FIG. 1A in magnified view, in accordance with some exemplary embodiments of the invention.
Figure 2:
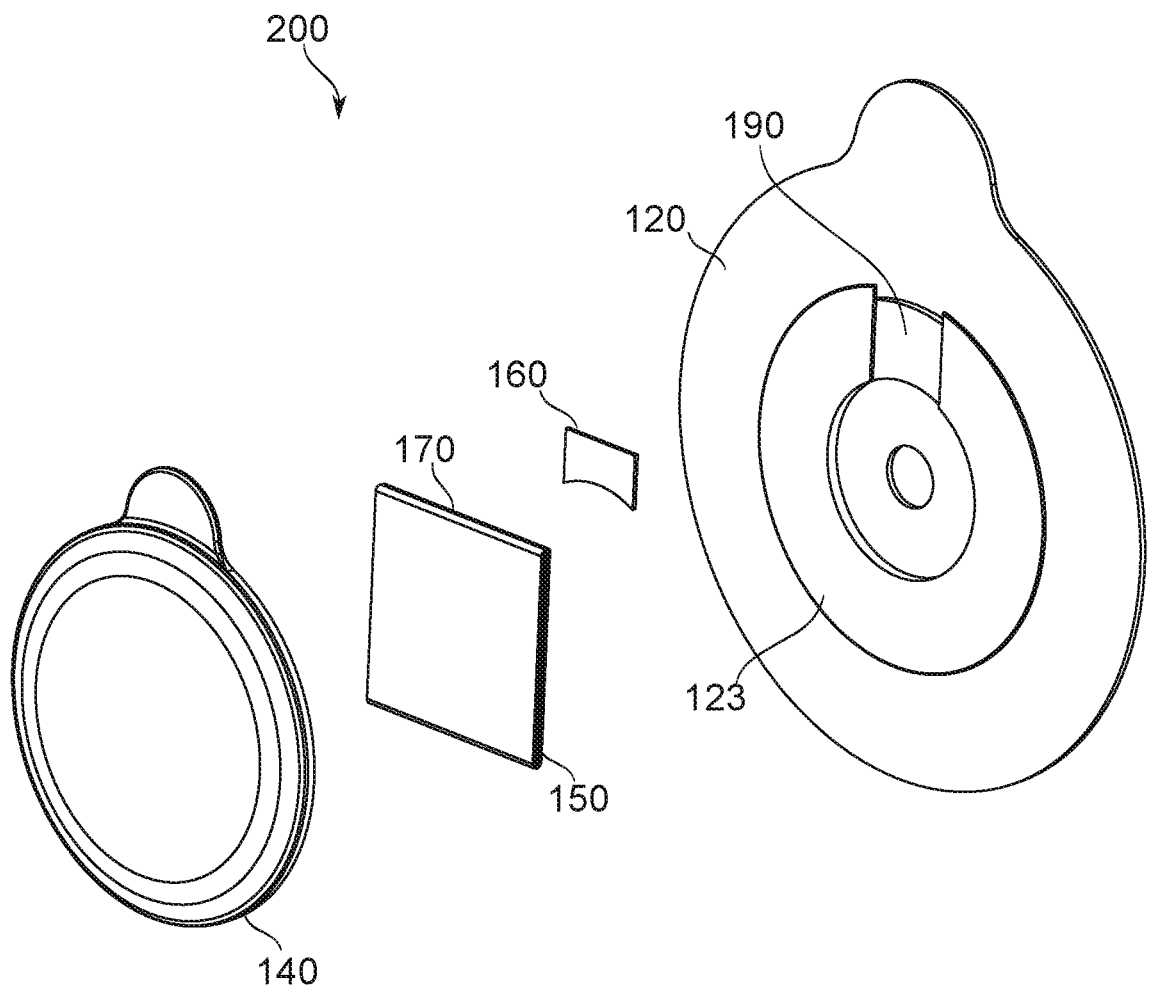
FIG. 2 schematically illustrates an exploded perspective view of an ostomy appliance, with integrated gas filter, in accordance with some exemplary embodiments of the invention.

Reference is now made to FIGS. 1A-1C and 2. FIG. 2 shows a gas filter 160 in a side wall of an ostomy appliance 200, according to some exemplary embodiments of the invention. Supporting region 190 is part of the ostomy wafer housing 123. Supporting region 170 is part of an optionally folded ostomy waste collection pouch 150.

In some embodiments, filter 160 and supporting regions 170, 190 are held together to form a filtering vent for gasses from the stoma. Optionally, the gasses are filtered of noxious odors during their passage through filter 160. In some embodiments, filter body 160 also comprises a barrier to the exit of solid and/or liquid stomal waste.

A sidewall enclosed filter is potentially an advantage for an ostomy appliance, by allowing the filter body to be enclosed and/or protected by appliance components that participate in other appliance functions such as mechanical support, waste containment, and/or stoma protection. Such a combination purpose potentially reduces a cost of manufacture associated with having a filtering functionality. A sidewall position also provides potential advantages by decoupling gas release from solid/liquid waste release. In some embodiments, pathways for evacuating solid/liquid waste or gaseous waste are separately actuatable. In some embodiments, physical separation of these functions allows greater specialization of structure for meeting their different requirements for release timing and control.

FIGS. 1A-1C exemplify an ostomy appliance 100 with separate gas and solid/liquid waste release channels, according to some exemplary embodiments of the invention. Ostomy appliance 100 includes a filter element 160 held in a sidewall of an adaptor housing 135 which is detachable from an ostomy wafer 120. FIG. 1C shows exemplary gas filter 160, filter supporting region 180 of and cap housing 135 of FIG. 1A in magnified view. FIGS. 1A-1B illustrate ostomy appliance 100 in overview (exploded perspective and sectional views, respectively).

In overview: in some embodiments of the invention, the ostomy appliance 100 comprises a stack of ostomy components. Most distal, and worn against the skin of the user (not shown), is ostomy wafer 120. Exemplary ostomy cap 130 is attached to ostomy wafer 120, for example, via flange 125. In some embodiments, a sealing element 115 is compressed between the ostomy cap 130 and the ostomy wafer 120. In some embodiments, cap 130 comprises one or more of a housing 135, cover 140, collapsed stomal discharge collection pouch 150, and/or gas filter 160. Wafer 120, sealing element 115, and cap housing 135 have apertures through which stomal discharge reaches collapsed pouch 150. Pouch 150 is releasable to expand and receive waste for disposal. Other configurations of ostomy stack components are found, for example, in U.S. Patent Application No. 61/645,118 by the Applicant.

In some embodiments, gas flow through filter 160 slows or prevents the build-up of internal pressure to an uncomfortable and/or dangerous level. Pressure buildup is prevented above, for example, 50 mmHg, 80 mmHg, 100 mmHg, 120 mmHg, 150 mmHg, or 200 mmHg. Potentially, lowered internal pressure increases the longevity ostomy appliance sealing, for example, sealing between the ostomy appliance and the skin.

Some potential advantages of a sidewall mounted filter relate to the restoration of continence functions to an ostomate.

Some continence restoration advantages potentially arise in combination with a collapsed pouch 150 configuration. A collapsed, optionally folded, pouch 150 potentially interferes with gas release through a filter located on cover 140, or integrated into the pouch 150 itself. A sidewall position can avoid interference—potentially, the filter is continuously operable to release gas, while pouch deployment can be delayed until there is a need to evacuate waste. In some embodiments of the invention, separation between gasses and solid/liquid waste occurs within the region defined by circumference 136. Separation may thus occur before waste reaches a waste disposal pouch, where gasses escape laterally through an aperture defined in the side wall. Liquids and wastes optionally continue proximally through lumen 138, and eventually into the pouch for disposal.

In one potential advantage for continence restoration, a continuously venting filter allows extended periods of wear without a need for pouch deployment to accommodate gas buildup. In some embodiments, an aspect of fecal continence is restored to an ostomate by restraining collapsed pouch 150 in a continence mode during normal wearing. In continence mode, solid and liquid waste are contained until pouch deployment for waste evacuation. Containment provided by continence mode is potentially complete or nearly complete, so that waste is unnoticeable by others (cryptic) in a social setting.

Fecal crypsis potentially increases freedom of activity for an ostomate, by reducing the need to hide and/or protect an external waste storage pouch. Fecal crypsis is also potentially aided by filtered gas release that reduces emitted odors. Also contributing to fecal crypsis is avoidance of a pouch potentially accumulating a volume of stagnant flatus. A gas-filled pouch is potentially visible to others and/or uncomfortable to wear—but does not fully deflate when flatus stops, since a filter ceases to be effective as soon as pressure equilibrates. The resulting stored reservoir of gas potentially also increases fecal odor released during evacuation, or if the bag is pressed on during wear. In contrast, a filter used with a collapsed bag potentially operates more effectively to prevent undesirable gas storage.

Timing evacuation according to need is another aspect of continence restoration. In particular, it is a potential advantage to not evacuate if pressure creating discomfort and/or an impression of intestinal fullness is primarily due to gas. Potentially, sensing of the difference used to determine a time of evacuation provides more time for liquids in stool to be reabsorbed by the body before stool evacuation. Potentially, the number of premature and/or unnecessary evacuations is reduced, reducing the cost of replacing consumable parts of an ostomy appliance. Other potential advantages include increased convenience due to a potentially increased duration between evacuations, and/or control of waste evacuation for an ostomate.

Another aspect of restored fecal continence is provision for pressure safety. In some embodiments of the invention, a pouch 150 deploys for filling with liquid and/or solid waste automatically, upon the occurrence of a threshold pressure. Optionally, this threshold is set to provide a safety release. In some embodiments, for example, cover 140 releases automatically upon a threshold pressure being reached, permitting deployment of pouch 150. Optionally, deployment is manual—for example, by removing cover 140—upon the sensing by an ostomate of a pressure which potentially indicates a need to evacuate. Pressure sensing by an ostomate can be a feeling of fullness. Optionally, sensing comprises a pressure indication by the ostomy stack itself; for example: a bulge, a stiffening of a pressurized surface, and/or an alert.

With respect to a safety release pressure, it is again a potential advantage to reduce or prevent ballooning pressure due to intestinal gasses. Potentially, a pathway for continuous release of gasses prevents a threshold pressure for automatic deployment from being exceeded by pressure due to gasses. Potentially, continuous release of gasses increases certainty that sensed pressure is (or is not) due to waste requiring pouch evacuation. Potentially, certainty is increased by keeping gas pressure normally low, and/or by providing an indication that gaseous pressure is being controllably released.

In some embodiments, the body 169 of filter 160 is of a known construction; for example: felt, cloth, foam, lattice, or cake. In some embodiments, the body 169 of gas filter 160 comprises an odor-absorbing material which filters odorants from outflowing gasses. Potentially, filtered odorants are noxious odorants, for example, fecal odors. According to the embodiment, odor absorption is, for example, by the use of activated charcoal, silica gel, zeolites, and/or carbide-derived carbon. In some embodiments, the filter is preloaded with perfumes and/or odor neutralizing substances, for absorbing gasses passing through the filter to render them less noxious. Potentially, filtering slows the release of gasses so that external concentrations of odorants are less noticeable to the ostomate and/or to others.

In some embodiments, elements of the ostomy appliance hold the filter element and/or protect it from fouling, while serving another functional role. Filter holding/protection includes, for example: keeping the filter element in place, sealing to the filter element, and/or straining of input to the filter element. Ostomy components adaptable for filter element housing include the pouch, cap, wafer, and/or ostomy appliance adaptor.

Figure 3A:
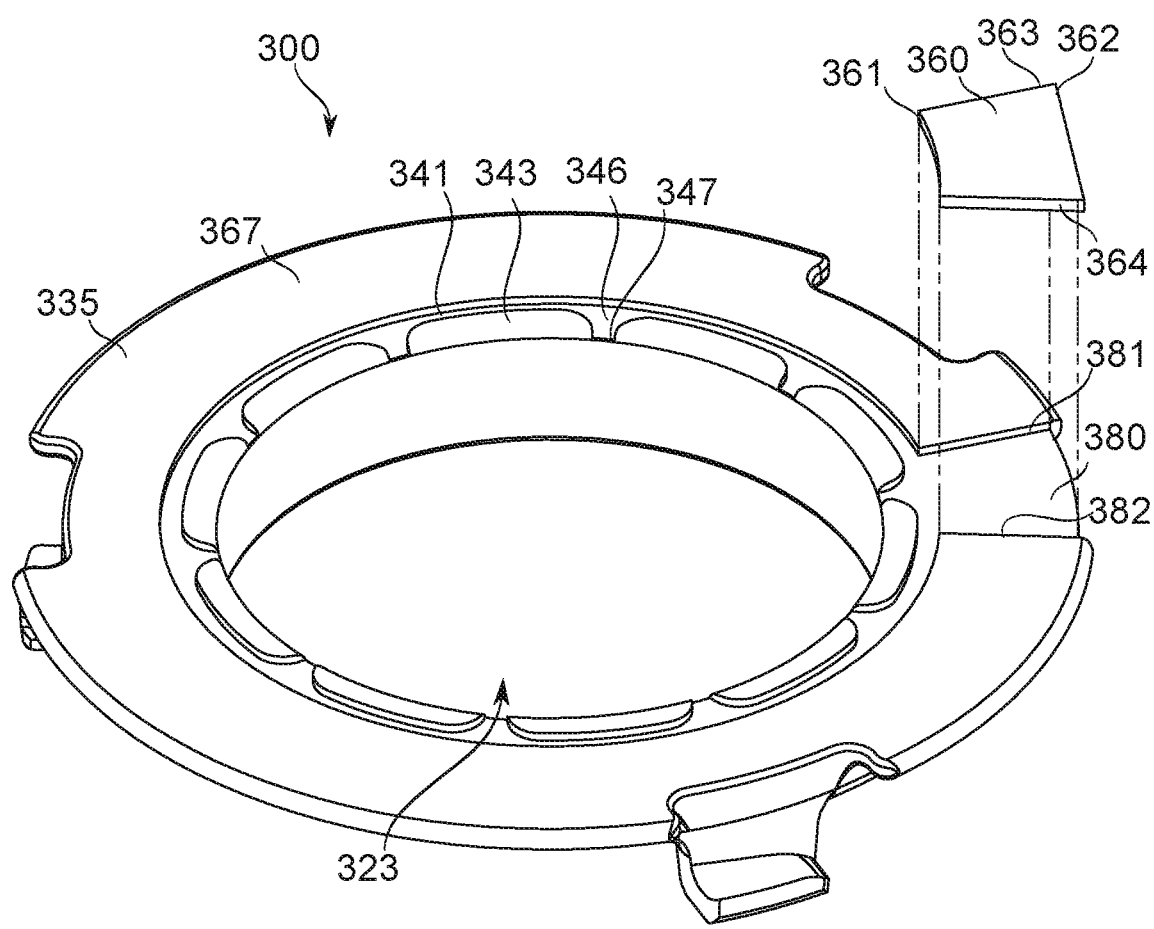
FIG. 3A schematically illustrates a perspective view of an ostomy cap housing together with a filter element, the housing including structures for straining input to the filter, in accordance with some exemplary embodiments of the invention.

In some embodiments of the invention, the filter holding aperture comprises at least a base element and a cover element, directly connected to one another. For example, gas filter 160 is housed between filter supporting regions 170 and 180. In some embodiments, the filter element comprises a pathway of communication for gasses to pass between a lumen of the housing and the housing exterior. The housing of the filter is such that exiting internal gas is primarily constrained to exit through body 169 of the filter. Flow is resisted outside side surfaces 163, 166, along enclosing surfaces 180, 170, 181, 182, and/or surfaces of the filter body 169 they enclose. FIG. 3A also illustrates pairs of housing and filter body surfaces 381, 363 and 382, 364 between which gas flow is resisted. Flow resistance is increased, for example, by sealing pressure, and/or by a sealing coating over surfaces of the filter body 360. In some embodiments, the base element is a housing 135 of an ostomy component; for example: a cap, adaptor, wafer, sealing element, or disc. In some embodiments, the housing comprises a rigid or semi-rigid material, for example polyethylene or polypropylene. In some embodiments, the housing comprises a flexible material, for example polyurethane rubber, silicone rubber, or thermoplastic elastomer (TPE).

In some embodiments, the base and/or cover element is a portion of an ostomy waste collection pouch 150. The pouch portion is, for example, a flange comprising a pouch mounting element, or a film comprising the containing portion of a pouch. In some embodiments, the cover element is a housing of an ostomy appliance component such as a closure, cap, adaptor, wafer, sealing element, or disc. In some embodiments, the cover element has a lumen and an exterior in common with a lumen and an exterior of the base element. In some embodiments, the cover element does not have a lumen, and/or does not have a lumen in common with the filter support base element. Optionally, the cover element comprises a membrane.

In some embodiments, the slot for filter 160 is sized to seal by a pressure fit on at least one side of filter 160. In some embodiments, bonding and/or adhering creates flow resistance between some filter element surfaces 163, 166, 169, and filter support surfaces 170, 180, 181, 182. In some embodiments, adhesive is applied between the filter element 160 and supporting regions 170, 180 of the aperture. Optionally, the adhesive applies as a liquid, paste, slurry, or polymer clay, to fill gaps between the filter and the aperture. According to the embodiment, adhesive is applied prior to inserting the filter element 160 into the aperture, or afterwards.

In some embodiments of the invention, the material of filter body 169 is directly in contact with filter supporting regions 170, 180. In some embodiments, filter body 169 is laminated on one or more surfaces (for example, surface 163, 166, 363, 364) by a filter sealing layer 168.

In some embodiments, filter sealing layer 168 covers an entire surface of filter body 169. In some embodiments, filter sealing layer 168 covers a partial surface of filter body 169.

According to the embodiment, the unconstrained thickness of filter element 160 is, for example, 0.25-0.4 mm, 0.3-0.5 mm, 0.7-1 mm, 1.4-3 mm, 2-4 mm, any thickness in between, or another larger or smaller thickness. In some embodiments, filter element 160 is compressed to, for example, 30-40% of its unconstrained thickness, 40-60%, 50-80%, 95-100%, or a smaller thickness. Filter element 160 in its narrowest (non-thickness) dimension is, for example, 3-4 mm across, 5-8 mm, 8-12 mm, 15-20 mm, larger, or smaller. Filter element 160 in its widest dimension is, for example, 3-4 mm across, 5-8 mm, 8-12 mm, 15-20 mm, 20-30 mm, larger, or smaller. In some embodiments, of the invention, filter element 160 is substantially flat, for example (but not only), as potentially results from a filter element cut from a sheet of filtering material of an above-described unconstrained thickness. In some embodiments, the ratio of filter thickness to the other two dimensions of the filter element is, for example, at least 5:1, at least 10:1, at least 20:1, or a greater ratio. In some embodiments, at least the broadest surface of the filter is sufficiently flat to receive a lamination such as filter sealing layer 168.

Gas throughput of filter element 160 is, for example, 1-2 ml/min, 2-5 ml/min, 7-13 ml/min, 20-30 ml/min, 40-80 ml/min, 75-125 ml/min, 150-200 ml/min, higher, or lower. For a reference, the throughput values given are under 100 mmHg of differential pressure between input and output surfaces.

Embodiments of Filter Input Strainers and Valves

Figure 3B:
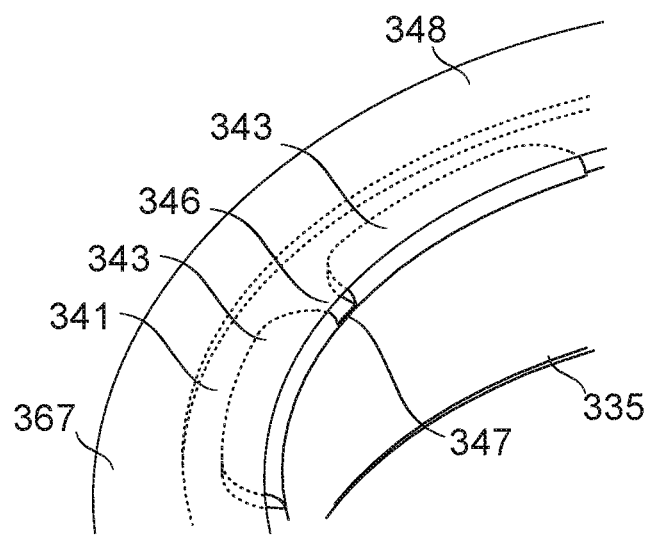
FIG. 3B schematically illustrates a perspective view of a portion of the cap of FIG. 3A, attached to a membranous material which closes an open face of waste-straining channel and inlet elements, in accordance with some exemplary embodiments of the invention.
Figure 3C:
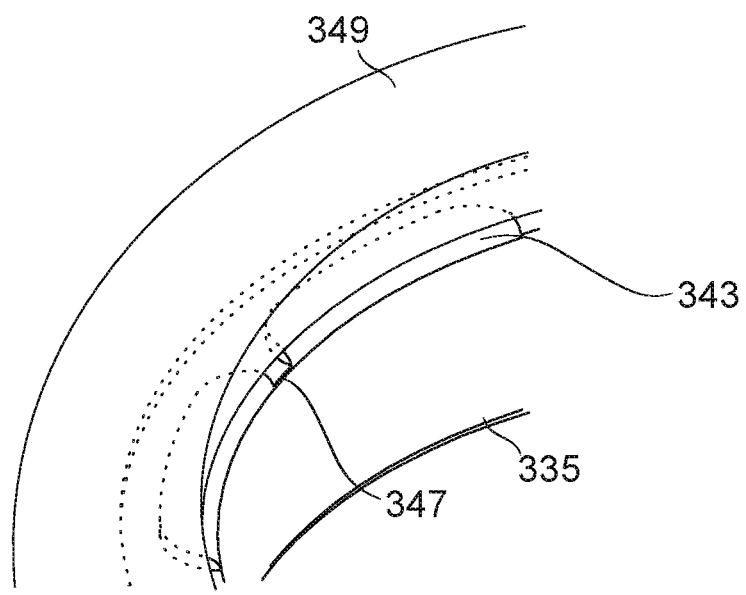
FIG. 3C schematically illustrates a perspective view of a portion of the cap of FIG. 3A pressed against a face closure structure that closes an open face of waste-straining channel and inlet elements, in accordance with some exemplary embodiments of the invention.

Reference is now made to FIGS. 3A-3C. These figures show examples of strainers protecting against blockage of filter 360, according to some exemplary embodiments of the invention. In some embodiments, strainers also resist blockage of their own channels that could lead to loss of gas release function.

In some embodiments of the invention, a strainer creates a separation between blocking waste and filter input structures. It is a potential advantage to thereby reduce the contact of input surface 361 of filter element 360 with non-gaseous material that could foul it. Fouling comprises, for example, increased resistance, reduced odorant absorption, and/or reduced throughput for the filter.

FIG. 3B shows a straining structure including housing 335 of FIG. 3A, and membranous material 348 attached to it, according to some exemplary embodiments of the invention. In some embodiments, conduit channel 341, inlet 346, and inlet aperture 347 comprise a gas-conductive connection separating input surface 361 and lumen 323. In some embodiments, inlet 346 and/or conduit channel 341 comprise recesses in housing 335. In some embodiments, one or more islands 343 help to define channel 341 and/or one or more inlets 346. In some embodiments, channel 341 is extended by placement of filter 360 toward the outer rim of the ostomy appliance, leaving a channel space more internally. Optionally, membranous material 348 is the material of an ostomy discharge collection pouch, for example, pouch 150.

FIG. 3C schematically illustrates solid-bodied ostomy stack elements fitted together to form straining structures, according to some exemplary embodiments of the invention. Housing 335 closes against closure structure 349, forming channel 341 and inlets 346. Optionally, closure structure 349 is a solid body which attaches, is fitted and/or flexibly seals to housing 335. Optionally, housing 349 is a housing of an ostomy appliance component such as an adaptor, wafer, or sealing element.

In some embodiments, venting stomal gasses are thus guided from inlet aperture 347 through inlet 346 to channel 341, and then to input surface 361. From input surface 361, they are filtered through the body of filter 360, and vented at filter output surface 362.

A long, narrow gas passageway before input surface 361 provides a potential advantage protecting against fouling by leakage past inlet aperture 347 by increasing a distance of travel. Potentially, intruding material is self-restricting due to the small channel size to form a plug preventing deeper contamination of the channel.

In some embodiments, a plurality of inlets 346 is provided. This potentially increases resistance to loss of gas-releasing function, for example, in the case that one or more inlets are fouled during use. In some embodiments of the invention, conduit channel 341 extends circumferentially around housing lumen 323. In some embodiments, channel 341 extends around the entire circumference. In some embodiments, channel 341 extends around a portion of the circumference. In some embodiments of the invention, there is a plurality of inlets 346 arranged at intervals (regular or irregular) around the stomal circumference. According to the embodiment, there are, for example, 16, 12, 10, 8, 6, 4, or 2 inlets 346. In some embodiments, there is one inlet 346. Optionally, an inlet is extended sufficiently so that plugging potentially occurs at a restricted extent of the inlet, without blocking it entirely.

In some embodiments, inlet apertures are themselves are configured to resist self-blockage. Straining comprises separating gas from solid and/or liquid waste in lumen 323, while directing gas toward filter element 360. In some embodiments, separation comprises size exclusion, wherein the dimensions of aperture 347 are small enough to exclude solid waste particles above a predetermined size. In some embodiments, aperture 347 is small enough that internal fluid pressure (for example, due to surface tension) prevents fluid from progressing through the aperture.

In some embodiments, the long dimension of inlet aperture 347 is, for example, 0.08-0.12 mm, 0.2-0.5 mm, 0.8-1.5 mm, 1.4-3 mm, 2.5-7.5 mm, 7-13 mm, a larger or smaller width, or any width in between. In some embodiments, the depth of the recess forming a portion of aperture 347 is, for example, 5-10 μm, 10-50 μm, 0.05-0.1 mm, 0.2-0.3 mm, 0.4-0.7 mm, 1-2 mm, 2-3 mm, a larger or smaller depth, or any depth in between.

In some embodiments of the invention, the surface of the material which forms inlet aperture 347 is hydrophobic. Potentially, this protects the filter element input surface from wetting. In some embodiments, the surface is treated to increase hydrophobicity. For example, the surfaces is coated with a wax or other hydrophobic substance, or treated to roughen the surface structure. Inlet aperture 347 hydrophobicity is, for example, equivalent exceeding a contact angle of 91-100°, 95-100°, 100-120°, 110-140°, or a higher contact angle.

Availability of alternate pathways for gas flow in the event of one or more apertures 347 becoming blocked during use is a potential advantage. Exemplifying use during the day, an ostomate wears housing 335 in a vertical position, with filter element 360 oriented at the top. Waste which reaches lumen 323 is potentially pulled downward by gravity. In this situation, lower apertures 347 potentially are blocked, while higher apertures (those nearer to the filter element) remain open to the passage of gasses. Exemplifying night use, an ostomate lies on a side, so input apertures to one side of the filter block before those on the other side.

When input apertures are flexible enough to be closed under pressure, they are potentially reversibly closable to the inflow of blocking waste. For example, pressure due to solid and/or liquid waste urging upon an inlet aperture 347 potentially closes the aperture before leakage into it occurs. Unobstructed apertures potentially remain open to gaseous exchange. When waste moves away from a pressure-blocked channel, for example after a change in ostomate position, the channel is potentially restored to function. An increase in gaseous pressure equilibrates on both sides of an aperture more easily, so the channel is potentially not closed thereby.

A potential advantage of multiple input apertures relates to a corresponding increase in input surface area. With multiple apertures, individual channels can be made small, while increasing the aggregate surface area of all apertures according to the number of channels. Also exemplifying night use, an ostomate lies on their back, at such an angle so that the housing is substantially horizontal in orientation. In some embodiments of the invention, input apertures are provided in sufficient number to overcome a predetermined average level of blockage. For example, ten apertures are provided where one is sufficient, so that 90% average blockage of all apertures still provides sufficient gas release.

In some exemplary embodiments of the invention, membranous material 348 is attached by welding and/or bonding to the surface of housing 335. Attachment is, for example, by adhesive, chemical treatment, and/or heat treatment. In some embodiments, the membranous material 348 is attached to one or more inlet- and conduit-channel wall structures 343. In some embodiments, the membranous material is attached to flange 367. In some embodiments, the membranous material prevents entry to the lumens of the input strainer from lumen 323 except at input aperture 347. Input aperture 347 is formed between the roof of membrane 348, and the floor and walls of the recess of inlet 346.

In some embodiments, membranous material 348 is a film known in the art for producing ostomy pouches. Optionally, the film is made from a single material, for example polyethylene, ethylene vinyl acetate, polyamide or cellulose. Optionally, the film is made from a plurality of materials, for example by a co-extrusion process combining two or more of the aforementioned film materials. In some embodiments, membranous material is a foil, for example, aluminum. In some embodiments, membranous material 348 is a porous structure such as a fabric or felt, sealed, for example, with a plastic coating. In some embodiments membranous material 348 is a layer of flexible material, for example silicone, polyester or polyethylene terephthalate. Optionally, the material is applied in wet form by techniques including spraying or brushing, and then dried. In some embodiments, the thickness of membranous material 348 is, for example, 0.01-0.025 mm, 0.045-0.055 mm, 0.09-0.11 mm, 0.18-0.22 mm, 0.25-0.35 mm, any thickness in between, or a greater or lesser thickness.

According to the embodiment, the lumen 323 diameter of housing 335 is 12-17 mm, 15-25 mm, 25-35 mm, 32-45 mm, 40-55 mm, larger, or smaller. The distance between the inner and outer diameters of flange 367 is, for example, 1-3 mm, 3-7 mm, 6-15 mm, 14-28 mm, more, or less. According to the embodiment, the overall length of lumen 323 is 0.8-1 mm, 1-2 mm, 2-7 mm, 5-15 mm, 15-25 mm, longer, or shorter.

Figure 4A:
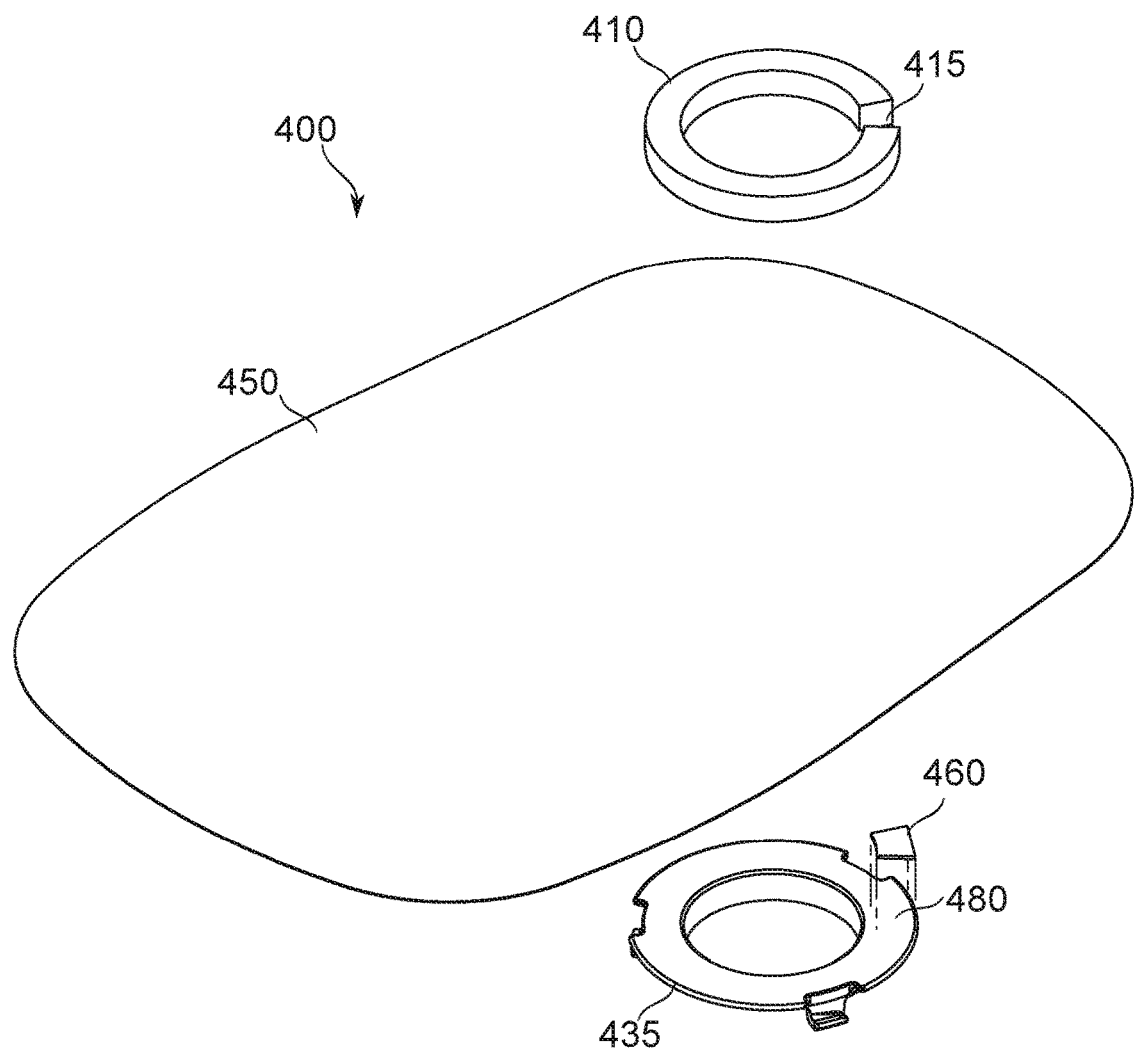
FIG. 4A schematically illustrates an exploded perspective view of an ostomy cap sub-assembly comprising a pouch and cap housing, together with a welding tool portion used in manufacturing the cap sub-assembly, in accordance with some exemplary embodiments of the invention.

Reference is now made to FIG. 4A, showing arrangements for manufacturing a pocket 480 for a filter 460, according to some exemplary embodiments of the invention. Cap sub-assembly 400 comprises a pouch film 450 and cap housing 435. These are shown with a portion of welding tool 410 used in manufacturing cap sub-assembly 400.

In some embodiments of the invention, supporting structures for filter 460 are constructed by selective bonding of surfaces. In some embodiments, one or more lumens are formed, for example, by selectively bonding adjoining surfaces on two or more sides of an unbonded region.

FIG. 4A shows pouch film 450 positioned over ostomy component housing 435. In some embodiments, film 450 and housing 435 are bonded, forming a pocket 480 for holding filter element 460. In some embodiments, bonding is performed with the use of welding tool portion 410. Welding tool portion 410 fits a press (not shown), and applies heat, pressure, radio frequency (RF) radiation and/or mechanical vibration to fuse ostomy component parts.

In some embodiments of the invention, welding tool 410 comprises a ring with a gap 415. Bonding during manufacturing comprises pressing tool 410 against pouch film 450 and housing 435. However, bonding does not occur in the region 480 underneath gap 415 where pressing does not occur. In some embodiments of the invention, this produces a pocket region at 480 between pouch film 450 and ostomy component housing 435. In some embodiments, the pocket region holds a filter element 460 in place. In some embodiments, a portion of the pocket region acts as an input straining structure.

Figure 4B:
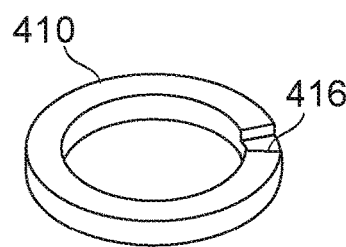
FIGS. 4B-4D schematically illustrate operation of a welding tool portion with a recess for assembling a filter to an ostomy housing, in accordance with some exemplary embodiments of the invention.
Figure 4C:
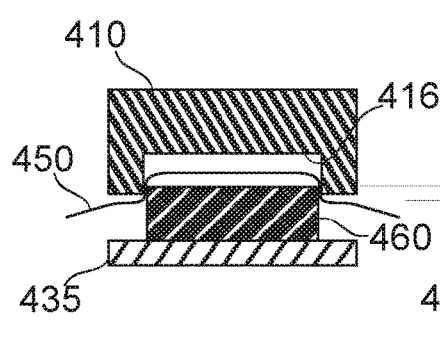
Figure 4D:
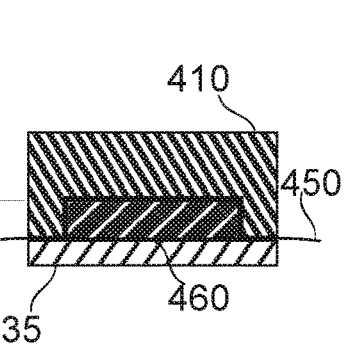

Reference is now made to FIGS. 4B-4D, showing use of an alternative tool portion 410 which has a recess 416 in place of gap 415. Tool portion 410 is inverted in FIG. 4B compared to FIG. 4A.

In some embodiments, recess 416 reduces or removes the pressure tool portion 410 exerts under the recess. In FIG. 4C, the tool portion 410 is in position over film 450, filter element 460 and housing 435 in preparation for welding. In FIG. 4D, the tool portion is pressed down over these elements to perform welding assembly.

In some embodiments of the invention, recess 416 is sized to substantially accommodate filter element 460 while compressing it by a distance 462. Distance 462 is, for example, 5%-20%, or 15%-30% of the uncompressed filter size. In some embodiments, the partial compression exerts sufficient pressure to seal film 450 to filter element 460. In some embodiments, the compression of filter body 460 during manufacture enhances sealing along the sides of the filter element, due to restorative forces.

According to the embodiment, filter 460 is placed either before or after bonding. In some embodiments, filter 460 is placed within region 480 before bonding forms the pocket that holds it. Alternatively, filter 460 is inserted into this pocket region after it is created. It may, for example, be compressed by an insertion tool, inserted, and the insertion tool removed. In some embodiments, filter 460 is held within a pocket region at 480 by pressing contact with pouch film 450 and/or ostomy component 435. In some embodiments, the pocket region at 480 holds filter element 460 so that it is in the path of least resistance for venting gasses. In some embodiments, the volume of pocket 480 comprises a depression in component housing 435, for example, as in supporting region 180 of FIG. 1C.

A potential advantage of holding filter 460 in place by compression and/or friction, rather than direct bonding, is that filter 460 is removable and/or replaceable without rendering the ostomy components that hold it inoperable. A potential advantage of a removable filter element is to allow filter replacement. Optionally, an external aperture of pocket region 480 is wider than the filter (easing filter entry), narrowing internally to seal against the filter body. Potentially, filter replacement allows longer use of an ostomy appliance after fouling of a first filter element preventing effective gas release and/or filtering. Additionally or alternatively, a user may decide to permanently or temporarily remove or break the sealing around a blocked filter to restore passive gas release.

Another potential advantage of compression holding for filter 460 is removing some bonding operations needed to produce the pouch, filter, and housing sub-assembly. Optionally, the body material of filter element 460 is not bonded to a backing layer, otherwise used to contain gasses passing through the filter body. Potentially, a simpler filter element 460 reduces manufacturing cost.

The shape of a lumen constructed by selective surface bonding is not limited to a single, to a straight, or to an unbranched lumen. For example, the channeled structures of FIGS. 3A-3C are constructible without a recess in housing 335 by selectively bonding membranous material 348 to define gas passageways. In some embodiments, this selective bonding is controlled by suitably arranging recesses and/or gaps in a bonding tool part such as 410.

Figure 4E:
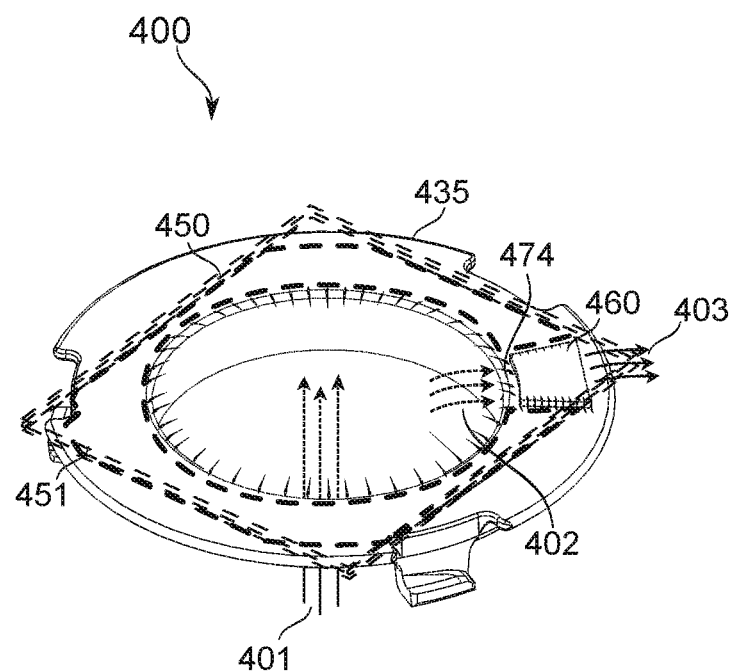
FIG. 4E schematically illustrates a perspective view of gas escaping from an ostomy cap sub-assembly comprising a pouch bonded to a cap housing and a filter, in accordance with some exemplary embodiments of the invention.

Reference is now made to FIG. 4E, which shows gas 401, 402, 403 escaping through a pressure-activated valve, according to some exemplary embodiments of the invention. Cap sub-assembly 400 comprises pouch film 450 bonded to a cap housing 435 at region 451, and a filter 460. Sub-assembly 400 is manufactured, for example, as described in relation to FIG. 4A. For clarity of illustration, the collapsed and folded pouch film 450 is shown fully or partially transparent, apart from dotted-line boundaries.

In some exemplary embodiments, region 474 comprises a pressure-activated valve formed by an arrangement of pouch film 450 selectively bonded to housing 435. Pressure (indicated by arrows 401) from within the ostomy appliance potentially pushes upwards against a surface of waste collection pouch film 450. Under sufficient pressure, pouch material at region 474 near the input surface of filter 460 lifts away from housing 435. The lifting creates an aperture through which escaping stomal gasses 402 can pass to the outside 403 of the stomal appliance. In some embodiments, pouch film 450 is pulled tight across region 474 so that the aperture there is closed in the absence of opening pressure. The pressure-dependent closing and opening at region 474 allows it to act as a flutter valve.

Figure 4F:
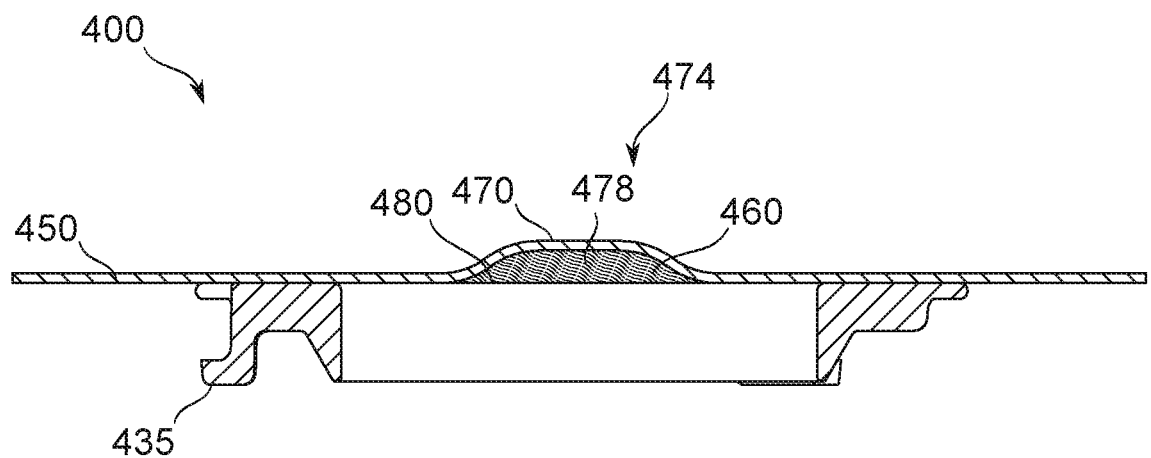
FIGS. 4F-4G schematically illustrate sectional views of an ostomy cap sub-assembly, showing details of the operation of a flutter valve, in accordance with some exemplary embodiments of the invention.
Figure 4G:
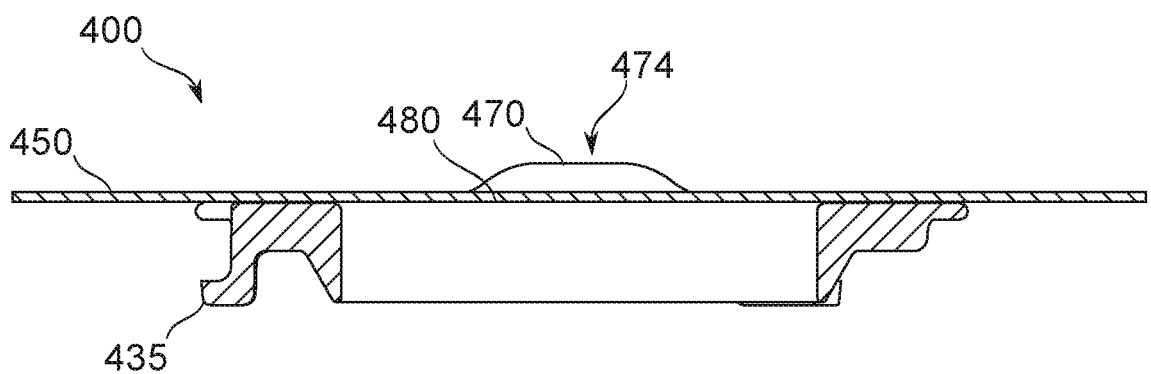

Reference is now made to FIGS. 4F-4G, which detail the operation of the flutter valve of FIG. 4B, according to some exemplary embodiments of the invention. The flutter valve comprises a portion of pouch 450 and the cap housing 435 at a region 474 near the input surface of filter 460. Potentially, the flutter valve helps to prevent or reduce fouling of the input surface of filter element 460.

In some embodiments, filter element 460 does not extend completely across the rim of the housing 435 at region 480. In some embodiments, an input strainer is formed in a region 474 where the material of pouch 450 and of housing 435 are not bonded.

In some embodiments (FIGS. 4E-4F), sufficient pressure within the stoma pushes a portion of pouch 450 away from the surface of housing 435. This creates an aperture 478 through which gasses can reach filter element 460. Once gas is released, the pressure decreases. In some embodiments, the material of pouch 450 comprising the flutter valve then returns to a position against the surface of housing 435 (FIG. 4G). Optionally, the material of pouch 450 is sufficiently tight and elastic to effect a full closure of aperture 478. Alternatively, aperture 478 is closed loosely, but with a sufficient reduction in aperture dimensions to resist the passage of fluid and solid waste.

A potential advantage of this flutter valve mechanism is to isolate filter element 460 from possible contamination by waste, except for periods when there is an immediate presence of stomal gasses to release. Optionally, when solid and/or liquid waste reaches the predetermined pressure required to open aperture 478, there is a likely need to evacuate in any case—since pressure that cannot be vented represents the presence of a significant quantity of waste. In some embodiments, the filter is disposed of after an evacuation event, so that a brief period of gas release impairment is acceptable.

In some exemplary embodiments, a flutter valve is positioned to distinguish between pressure from gasses, or from liquid/solid waste; for example as follows. In some embodiments, a flutter valve which opens and closes according to surrounding pressure is built into an input strainer such as that of FIGS. 3A-C. Optionally, a flutter valve is normally open, and closes under external pressure. With elevated gas pressure within the stomal appliance, the valves remain open, as pressure rapidly equilibrates on both sides of the flutter valve. However, in the presence of elevated pressure due to liquid or solid, input straining slows or prevents pressure equilibration. When the pressure differential across the flutter valve is great enough (due to waste pushing from outside), the aperture of the flutter valve closes. Potentially, this prevents an input aperture from itself becoming fouled. If pressure is later removed (for example, if the ostomate changes position), an unfouled input aperture may again be available to allow passage of gasses.

Shape in the Design of Filter Elements

Figure 5A:
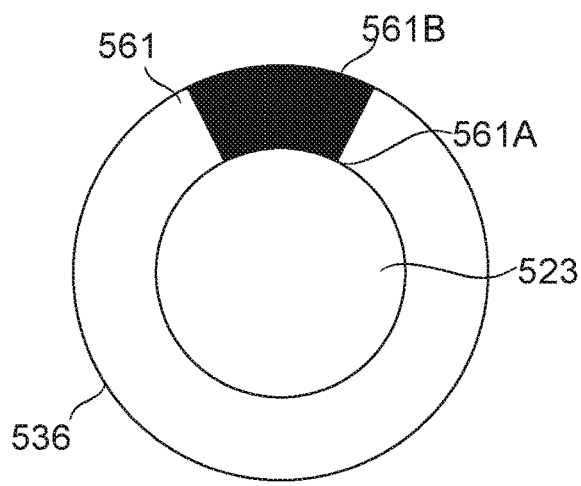
FIGS. 5A-5C schematically illustrate frontal views of filter elements with shapes adapted for different filtering and/or positioning requirements, in accordance with some exemplary embodiments of the invention.
Figure 5B:
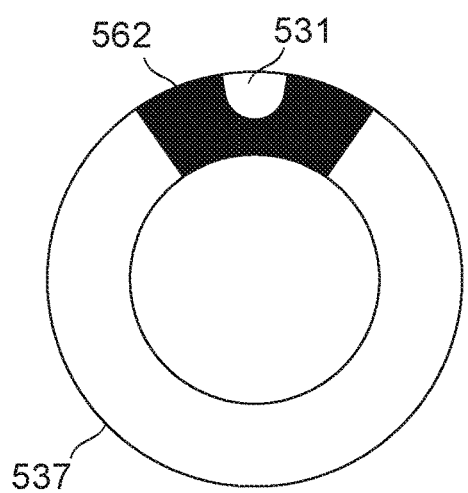
Figure 5C:
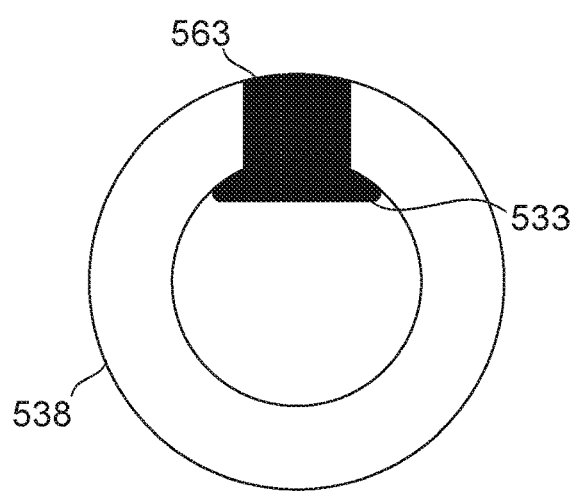

Reference is now made to FIGS. 5A-5C, which show filters 561, 562, 563 shaped for different filtering requirements, according to some exemplary embodiments of the invention.

In some embodiments of the invention, the shape of a filter element is chosen to increase the absorption area of a filter element. Additionally or alternatively, the shape is chosen to make room for additional surface attachments so that the strength of the lumenal wall is not compromised.

FIG. 5A illustrates an exemplary filter element 561 placed on or within a recess or pocket region of exemplary ostomy component housing 536. The filtering length stretches between input surface 561A, in contact with the lumen 523 of the housing 536, and the output surface 561B. In some embodiments of the invention, filter element 561 is restricted to occupy only a portion of the ostomy component wall circumference. The circumference portion is, for example, 90°, 60°, 45°, 20°, 10°, any portion in between, or a larger or smaller portion of the wall circumference.

A potential advantage of occupying a restricted portion of the wall circumference is that the remainder of the wall is available, for example, for connecting to the surface of another ostomy component, such as a waste collection pouch. As more surface area is available for connection, the strength of the overall ostomy appliance is potentially increased. Another potential advantage of occupying a restricted portion of the wall circumference is correspondingly reduced filter material use. A non-annular filter shape also allows use of a more efficient filter shape when cutting from a sheet of filter material, reducing wastage.

FIG. 5B illustrates an exemplary filter element 562 placed on or within a recess or pocket region of exemplary ostomy component housing 537. In some embodiments, filter material is cut from a region 531 within the arc occupied by filter element 562 in the housing wall. In some embodiments, region 531 is available for attachment, for example, to an ostomy waste collection pouch. Region 531 is, for example, on the outer wall of housing 537, on the inner wall, or enclosed within the outlines of an aperture of filter 562. Region 531 is of any shape; for example: rounded, square, rectangular or triangular. In some embodiments, housing 537 comprises a recess complementary in shape to filter element 562, within which filter element 562 fits. In some embodiments, housing 537 is flat, and attachment, for example, to a pouch, comprises pressing the membrane past the filter so that it contacts region 531.

A potential advantage of filter material-free regions within the body of the filter is additional points of attachment between housing 537 and another ostomy component such as a pouch to which it attaches. Potentially, additional points of attachment allow the circumferential extent of filter element 662 to be increased without compromising strength.

FIG. 5C illustrates an exemplary filter element 563 placed on or within a recess or pocket region of exemplary ostomy component housing 538. In some embodiments of the invention, filter element 563 has a portion 533 which extends into the lumen of housing 538. In some embodiments of the invention, the extended portion 533 is shaped to increase an available edge surface area. In some embodiments, the surface area exposed by the extended portion is increased by lengthening its contour; for example, by making the contour wavy or jagged. In some embodiments, the surface area is increased by making slits in the body of the filter. Potentially, narrow slits serve a straining function resisting the intrusion of solid or liquid waste. In some embodiments, extended portion 533 is left uncoated on its faces so that the body of the filter is exposed.

A potential advantage of increased exposed surface area of filter 563 is to mitigate the effects of filter input surface fouling. A tenfold increase in surface area, for example, potentially mitigates a tenfold reduction in gas absorption due to fouling.

Filter element 563 extends into the lumen of housing 538, for example, by 1-3 mm, 2-5 mm, 3-8 mm, 7-13 mm, any length in between, more, or less. In some embodiments, the exposed input surface area of filter element 563 is larger than the surface area which would be exposed if the extension was removed. The relative difference is 20-50%, 50-150%, 100-300%, 300-1000%, or a larger or smaller percentage.

It should be noted that the design features and relative advantages discussed in relation to FIGS. 5A-5C can be combined; and, according to the embodiment, can be synergistic. Thus, for example, a requirement to reduce the amount of filter material used is met in some embodiments by a low-wastage shape. In some embodiments, that a shape with a "bite" taken from one side allows attachment of holding surfaces mid-way along the filter length. In some embodiments, the protruding complement to this "bite" is not discarded, but extends into the lumen of the ostomy component on the other side, increasing filter input surface area.

Figure 6:
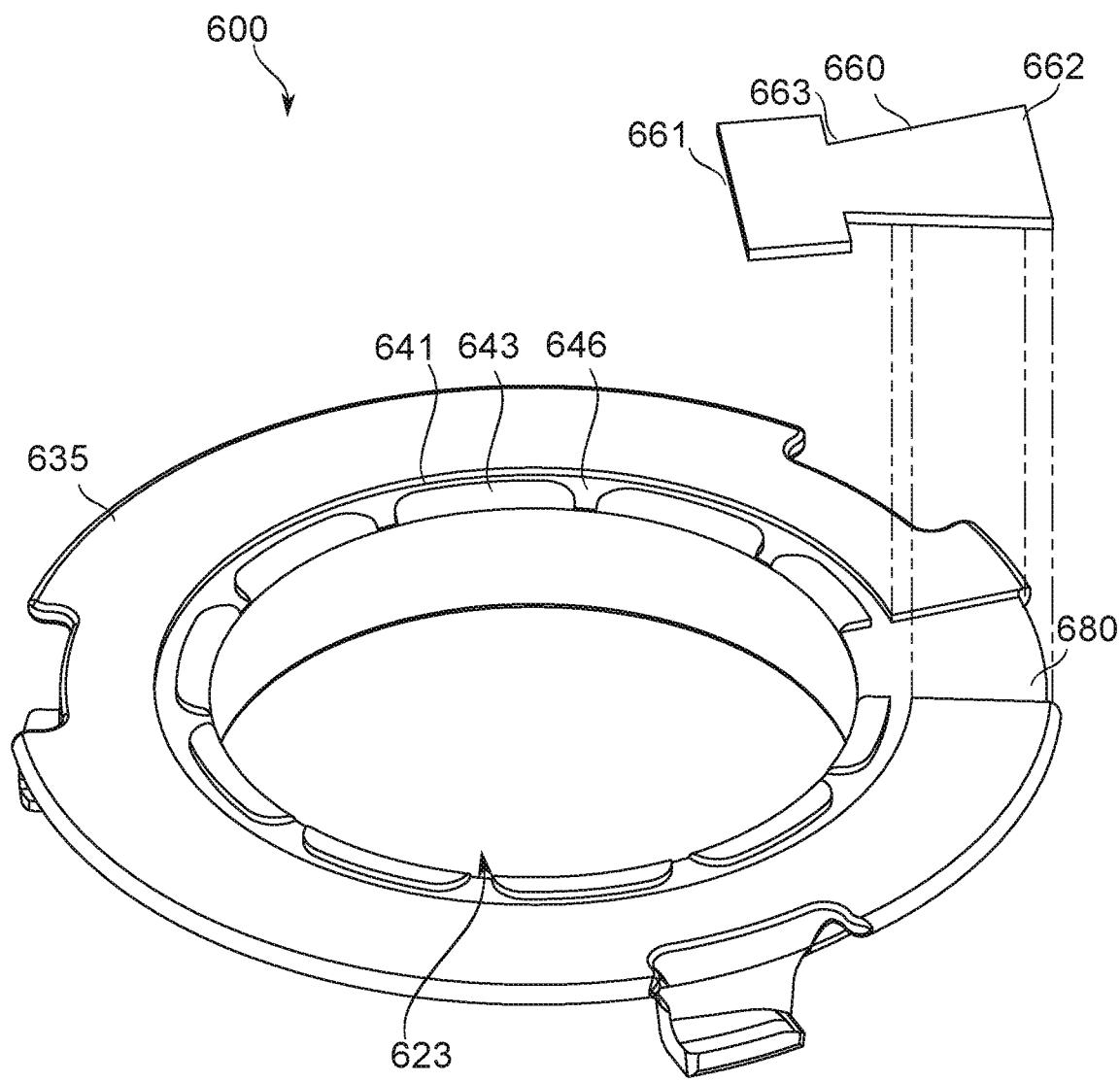
FIG. 6 schematically illustrates an exploded perspective view of a cap sub-assembly of an ostomy appliance comprising a housing adapted to strain gas input to a filter element, in accordance with some exemplary embodiments of the invention.

Reference is now made to FIG. 6, showing combined mechanisms of filter throughput protection, according to some exemplary embodiments of the inventions. Housing 635 is adapted to strain gas input to a filter element 660. Input surface 661 of filter element 660 is furthermore shaped to increase the area potentially available for gas absorption into the filter body.

In some embodiments of the invention, considerations of filter shape design (exemplified in FIGS. 5A-5C) are combined with an input strainer (exemplified in FIGS. 3A-3C). In FIG. 6, an exemplary input strainer is shown (for clarity, it is illustrated without overlying membrane or other channel closure). The strainer comprises gas input 646, input channel 641, and channel walls 643 surrounding the lumen 623 of ostomy component housing 635. Filter element 660 is shown with at least two types of filter input surface regions. Surface region 663 is the "clean" input region, protected by the input strainer. Surface region 661, by contrast, is unprotected, and extends into lumen 623. There, although it is exposed to fouling by waste, increased surface area potentially allows accepting gas fast enough to prevent pressure buildup.

A potential advantage of combining both filter protection types in one device is that each serves as a backup for the other. Potentially, each protection type is relatively more robust in different circumstances, for example due to orientation or waste consistency.

Figure 7:
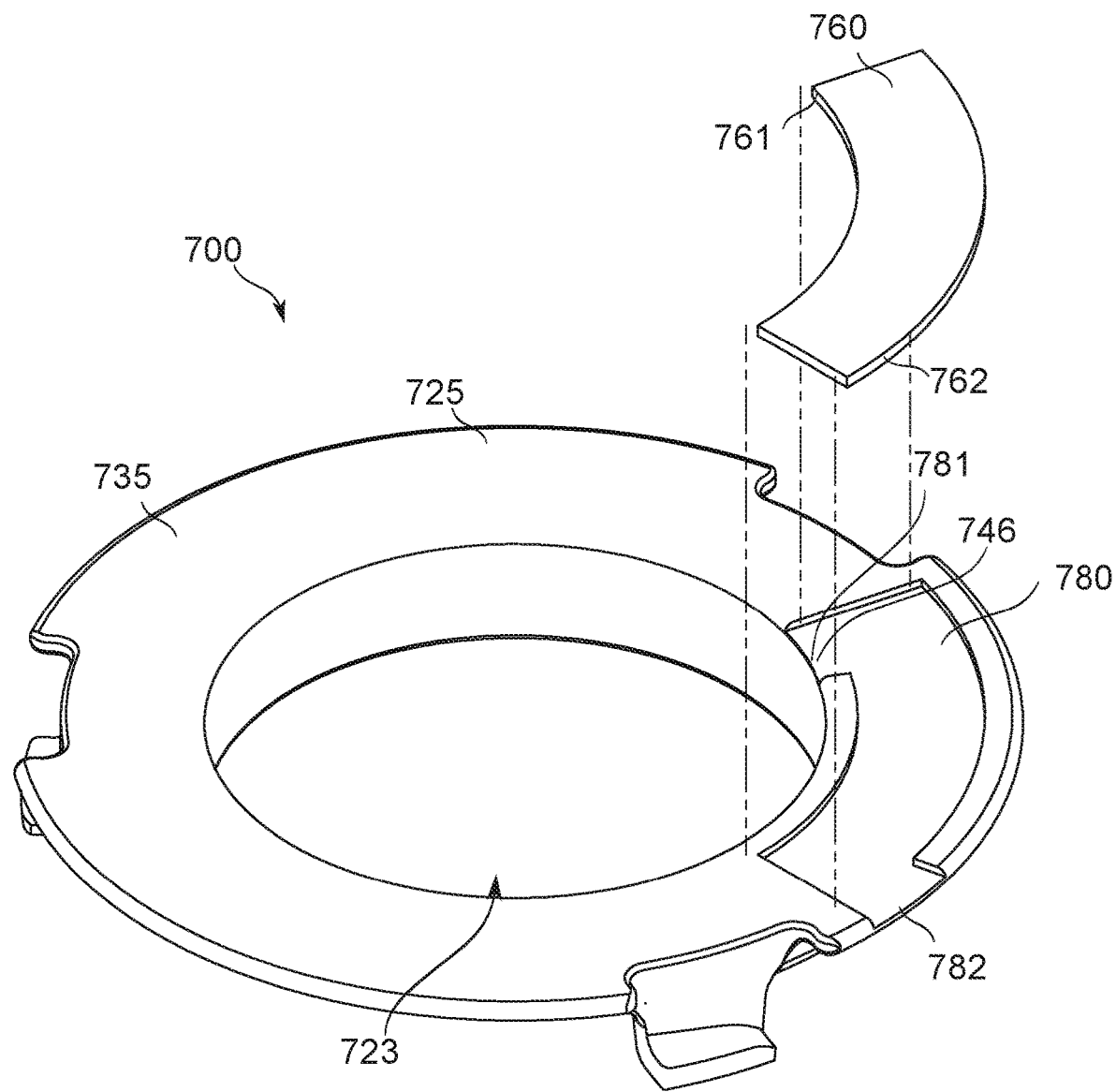
FIG. 7 schematically illustrates a perspective view of a cap sub-assembly of an ostomy appliance comprising a housing adapted to form a minimum-length pathway of filtered gas flow across a relatively narrow flange, in accordance with some exemplary embodiments of the invention.

Reference is now made to FIG. 7, showing housing 735 shaped to lengthen the venting path through filter element 760, according to some exemplary embodiments of the invention.

In some embodiments of the invention, the minimum filtering pathway through filter element 760 is longer than the shortest distance across the filter. A lengthened venting path potentially allows greater reduction in odor by filtering, and/or reduces the chance of leakage making its way all the way across the filter element. In some embodiments, the input surface 761 of filter element 760 is circumferentially offset from output surface 762. The offset, formed by the surrounding walls, forces gasses escaping lumen 723 to the exterior to route circumferentially as well as radially.

In some embodiments of the invention, a housing 735 comprises a recess 780 fitted to the shape of filter element 760. In some embodiments, recess 780 has an open section 781 near lumen 723 which defines the input surface 761 of filter element 760 when it is inserted. In some embodiments, recess 780 has an outer open section 782 which defines the output surface 762 of filter element 760.

In some embodiments, an additional or alternative enclosure defines a filter input surface 761 and/or an output surface 762. For example, an embodiment such as that of FIG. 9B hereinbelow is adapted so that the pattern of attachment of a pouch film defines offset input and output surfaces.

A potential advantage of using a circumferential offset to define a minimum gas filtering path length is that the width of flange 725 can be made narrower than the desired filtering path length. Additionally or alternatively, filter element 760 can be made narrow relative to the flange 725, so that there is room for a deeper input protecting region 746 to be defined. In some embodiments, input region 746 comprises an input straining aperture and/or a flutter valve.

Figure 8:
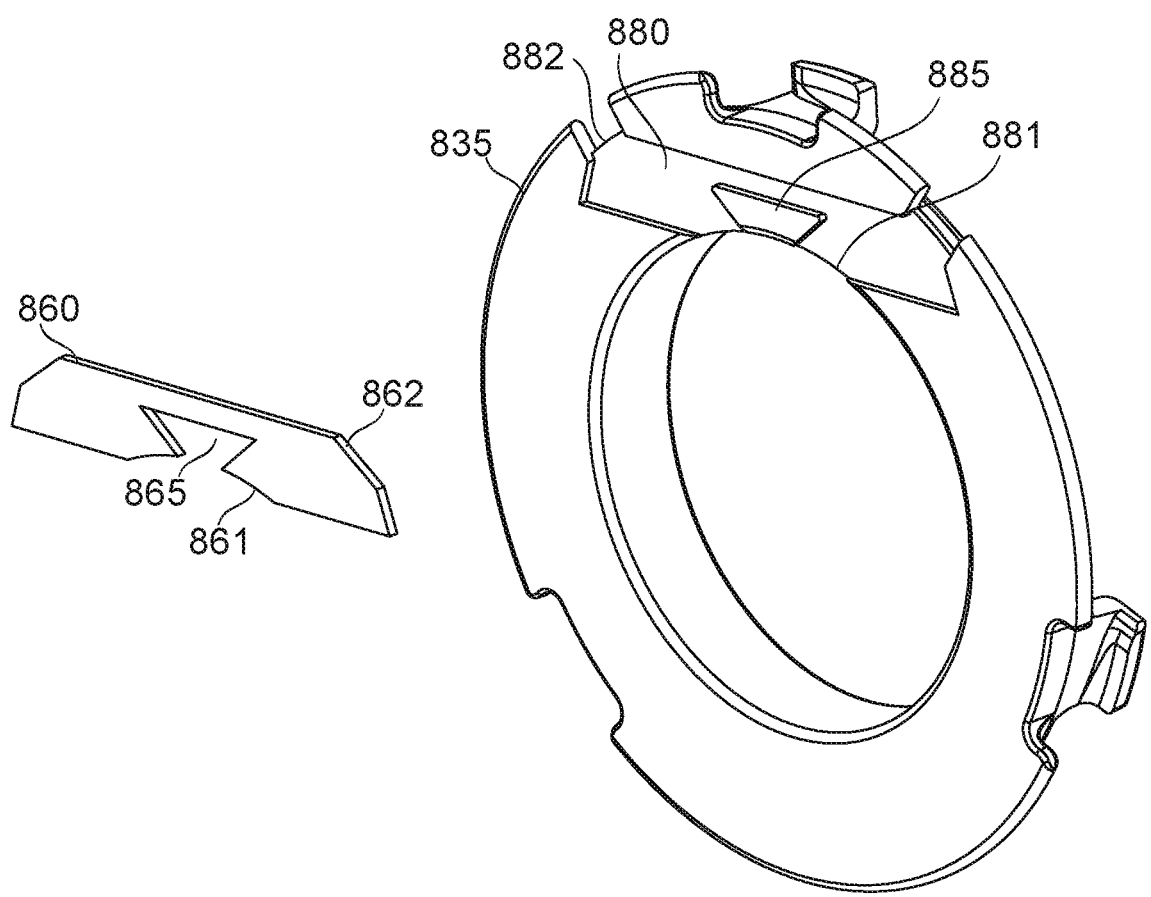
FIG. 8 schematically illustrates a perspective view of an ostomy cap housing and a filter element shaped for multiple filtering and/or positioning requirements, in accordance with some exemplary embodiments of the invention.

Reference is now made to FIG. 8, which shows a filter element 860 shaped to combine design elements previously described, according to some exemplary embodiments of the invention.

In some embodiments of the invention, filter element 860 comprises a plurality of input surfaces 861. In some embodiments, filter element 860 comprises a plurality of output surfaces 862. In some embodiments, input and/or output surfaces 861, 862 are defined by openings 881, 882 in depression 880 in housing 835.

In some embodiments, filter element 861 comprises a notched region 865 with a shape complementary to the shape of an attachment region 885 of housing 835.

In some embodiments, filter element 860 fits within a substantially rectangular profile, modified as necessary to fit the shape of recess 880 in housing 835. A potential advantage of a rectangular profile for a filter element is that it can be manufactured from a sheet of filter material with low wastage in the spacing between individual elements cut from the material.

The design of exemplary filter element 860 combines considerations for filter design previously described. A circumferential offset between input and output surfaces increases filter pathway length. An open central region permits attachment of two holding surfaces. Furthermore, an efficient shape reduces wastage of filter material.

It should be noted that recess 880 is only one example of a way to constrain the flow of gasses through filter element 860. Selective bonding by adhesion and/or welding, for example to the membrane of a waste collection pouch, is another way to house filter element 860.

Pouch-and-Housing Filter Element Holders

Figure 9A:
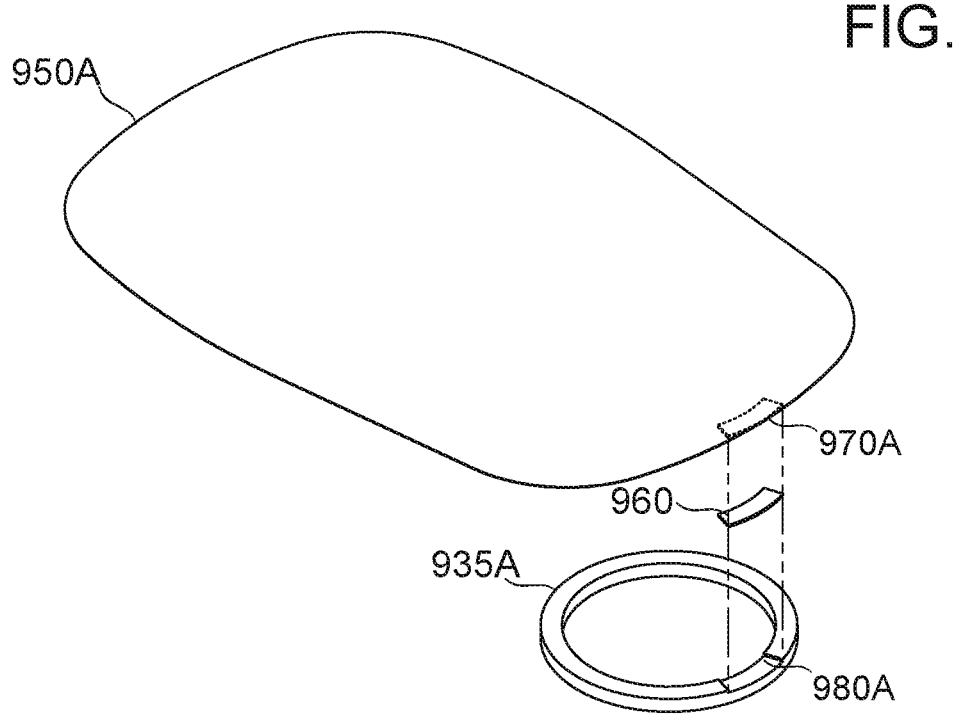
FIGS. 9A-9B schematically illustrate filter element holding structures with and without a preformed recess, in accordance with some exemplary embodiments of the invention.
Figure 9B:
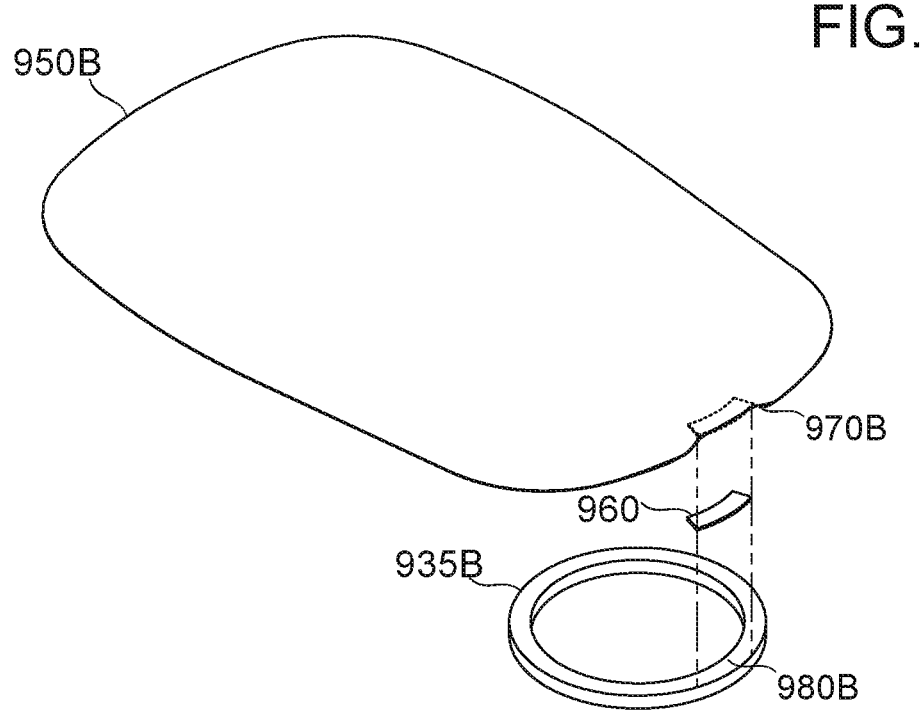

Reference is now made to FIGS. 9A-9B, which show alternative examples of pockets for holding a filter element 960, according to some exemplary embodiments of the invention. The pockets comprise the membranous material of a waste collection pouch 950, and an ostomy component housing 935A, 935B. In general, a solid-bodied housing may fully or partially accommodate a filter in a recess. Additionally or alternatively, a membrane may bulge over part or all of a filter to accommodate it.

In some embodiments of the invention, ostomy component housing 935A has a recess 980A fitted to the size of filter element 960. In some embodiments, ostomy pouch 950A is attached to housing 935A, for example by adhesion or welding. In some embodiments, a holding region for filter element 960 is thereby created between recess 980A and a region 970A of pouch 950A.

In some embodiments of the invention, ostomy component housing 935B is flat. In some of these embodiments, a region 970B of pouch 950B bulges over filter element 960, pressing it to housing 935B.

In some embodiments, filter element 960 is thicker than recess 980A, while region 970B of ostomy pouch 950B bulges over it.

In some embodiments, filter element 960 is placed between two holding surface regions during or before joining of the surfaces. Alternatively, filter element 960 is inserted between region 970A or 970B and 980A or 980B after attachment of pouch 950A, 950B and housing 935A, 935B.

Figure 10A:
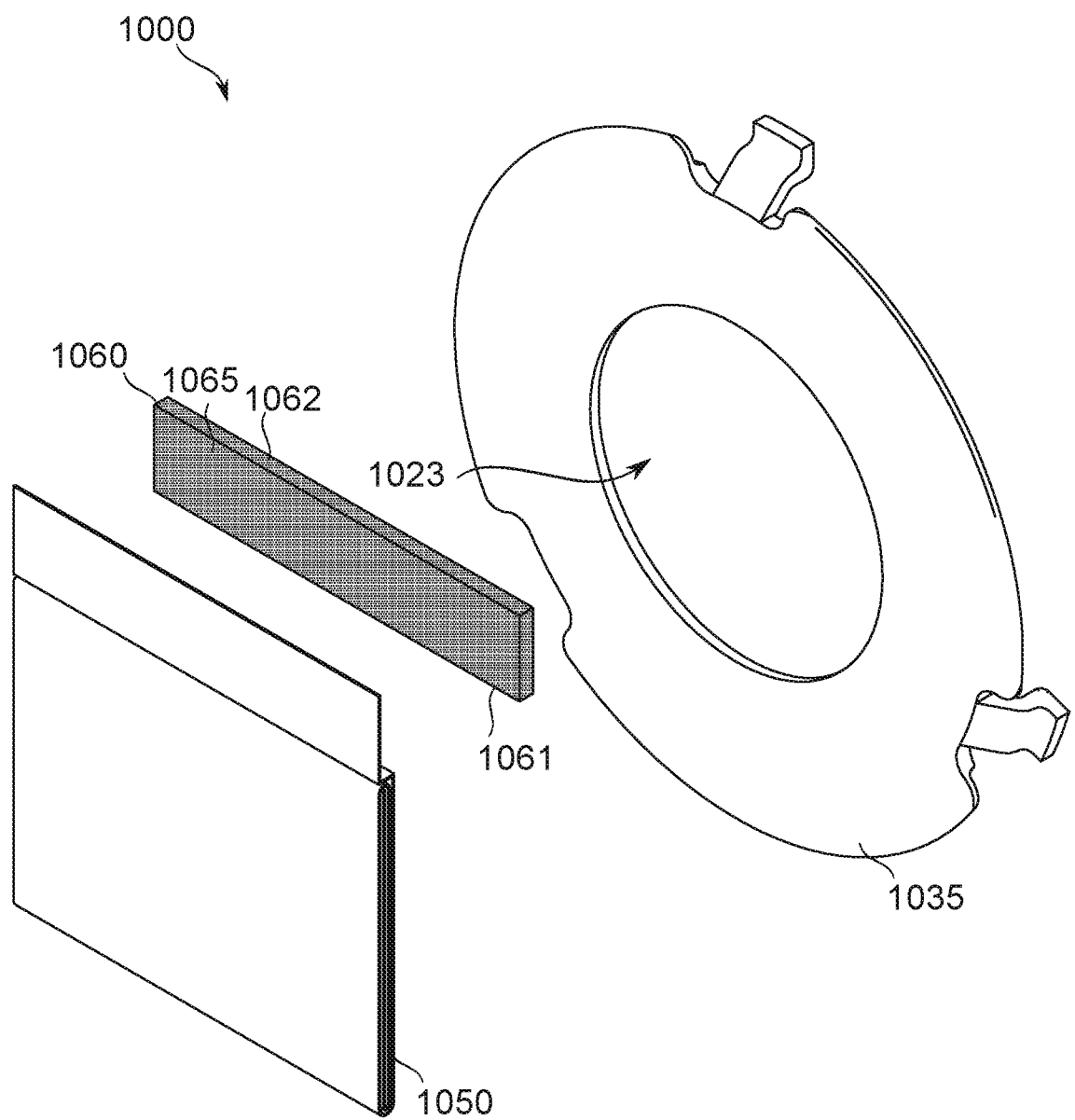
FIG. 10A schematically illustrates an exploded perspective view of a cap sub-assembly comprising a flat filter element and a flat-folded pouch attached alongside each other to a surface of a cap housing, in accordance with some exemplary embodiments of the invention.
Figure 10B:
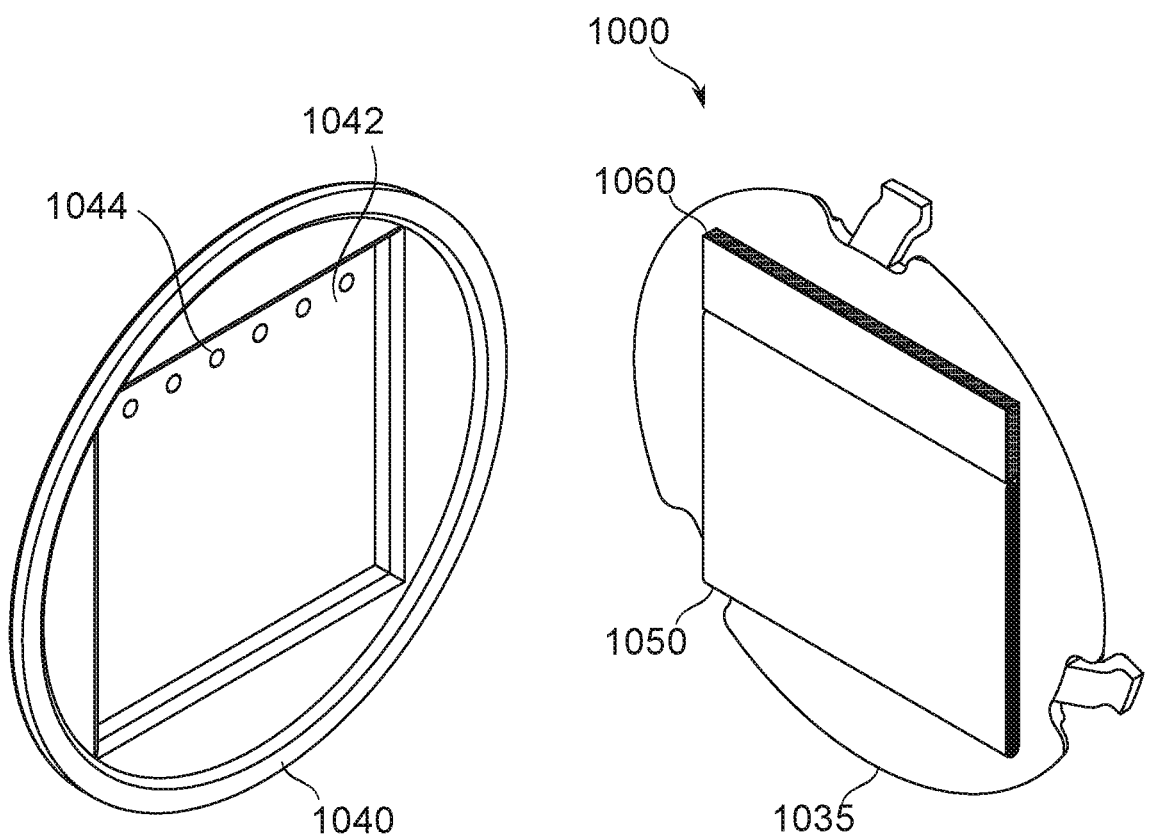
FIG. 10B schematically illustrates a perspective view of the sub-assembly of FIG. 10A together with a cap cover shaped to receive the pouch and filter element, in accordance with some exemplary embodiments of the invention.

Reference is now made to FIGS. 10A-10B, showing a filter element 1060 and folded pouch 1050 attached beside each other to a housing 1035, according to some exemplary embodiments of the invention. Potentially, this configuration provides some protection against contamination to filter input surface 1061 in a low combined pouch/filter profile.

In some embodiments of the invention, an input surface 1061 of filter element 1060 is positioned over a lumen 1023 of a housing 1035. The illustrated position allows access by interior stomal gasses. In some embodiments, an output surface 1062 is open to the exterior of the ostomy appliance.

In some embodiments, a portion of a folded ostomy pouch 1050 lies next to the filter element 1060 on a surface of the housing 1035. Potentially, this protects input surface 1061 from fouling. In some embodiments, one or more faces 1065 of the filter element are sealed against gas exit, for example, by a portion of pouch 1050.

A potential advantage of assembling filter element 1060 and pouch 1050 side-by-side on a surface of housing 1035 is a reduction in overall ostomy component height.

In some embodiments of the invention, cover 1040 overlays housing 1035, pouch 1050, and filter element 1060 during normal wear. In some embodiments, a recess 1042 of cover 1040 fittingly encloses pouch 1050 and filter 1060. In some embodiments, cover 1040 presents a flat outer surface appearance as a result of the fitting enclosure by recess 1042. In some embodiments, cover 1040 is removed to allow deployment of pouch 1050. In some embodiments, cover 1040 is fully detachable from the ostomy appliance.

In some embodiments, cover 1040 has ventilation holes 1044, which allow gas filtered through filter element 1060 to exit the apparatus. In some embodiments, cover 1040 bulges outward when there is an internal pressure exerted through lumen 1023. Venting gas potentially allows distinguishing a pressure bulge due to gas, which can be vented, from a bulge due to waste needing evacuation for disposal.

In some embodiments, a flat-folded bag is used along with a filter in another configuration. It is, for example, folded in front of the filter (proximally), as in exemplary embodiments of FIGS. 1A-1B, 2, and/or 13A-13B.

Insertable/Removable Filter Elements and Filter Holders

Figure 11:
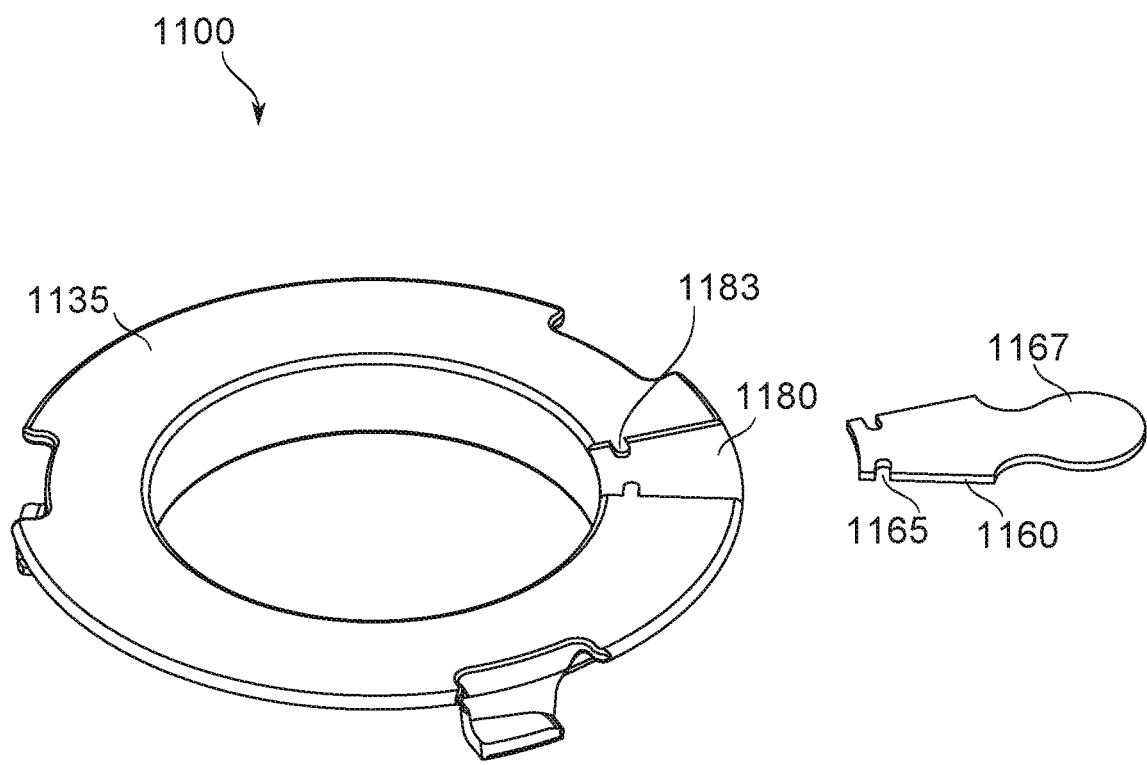
FIG. 11 schematically illustrates a perspective view of a cap housing with a flat filter element adapted to be removably held within a recess of a cap housing, in accordance with some exemplary embodiments of the invention.

Reference is now made to FIG. 11, which illustrates a removable filter element 1160 of ostomy sub-assembly 1100, according to some exemplary embodiments of the invention.

In some embodiments, the open face of housing 1135 and/or of recess 1180 is covered over by another component (not shown for clarity). The additional component is, for example, another ostomy component housing, or a portion of an ostomy pouch.

In some embodiments of the invention, filter element 1160 is insertable and/or removable by the ostomate during operation (wearing) of the ostomy appliance. In some embodiments, a grip 1167 allows filter element 1160 to be manipulated for insertion and/or removal from a holding region 1180. In some embodiments, grip 1167 is a relatively inflexible tab, for example of stiff plastic, so that the filter can be inserted without collapsing. In some embodiments, a stiff backing extends over a larger surface region of filter element 1160, or a whole surface. In some embodiments, insertion is by pressing filter element 1160 into an aperture without a protruding tab. Optionally, filter element 1160 is retrievable by pulling on a protruding element other than a tab, such as a string.

In some embodiments of the invention, holding region 1180 comprises one or more snaps 1183 adapted to fit into hollows 1165 on filter element 1160. In some embodiments, inserting filter 1160 into holding region 1180 briefly deflects flexible and elastic snaps 1183. Snaps 1183 snap back into hollows 1165 when filter element insertion is completed. In some embodiments, portions of filter 1160 deflect and/or compress during insertion, and return to place after passing snaps 1180.

A potential advantage of a removable filter element 1160 is that a filter element which has become fouled during use can be removed, and a new filter element put in its place. Optionally, removable filter element 1160 is temporarily removable or loosenable to release overpressure, for example, due to a sudden gas bolus, and then returnable to position. Optionally, removable filter element 1160 is reused in a new cap sub-assembly 1100 after a used cap sub-assembly 1100 has been disposed of.

Figure 12A:
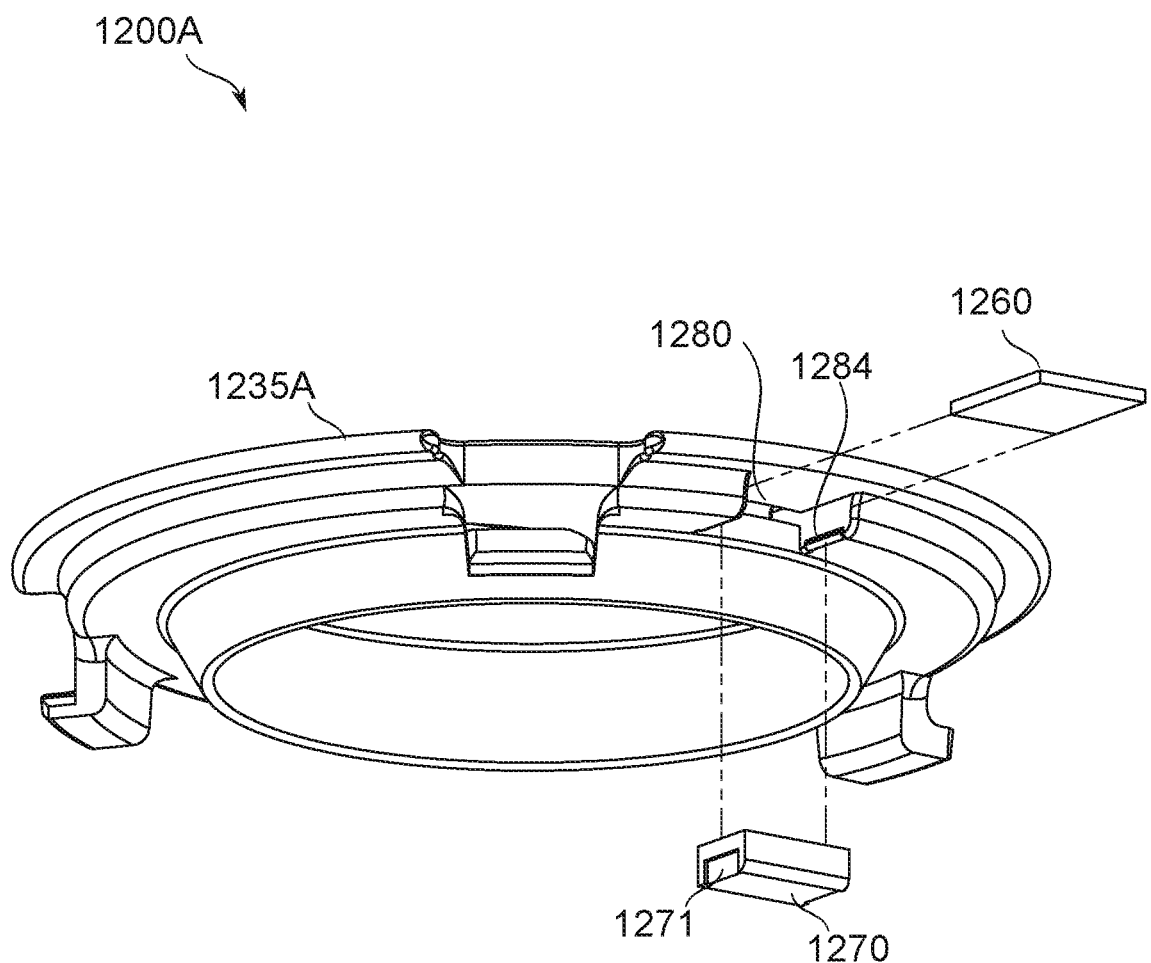
FIG. 12A schematically illustrates a perspective view of a cap housing with a flat filter element adapted fit within a recess of cap housing, and secured on at least one side by an insert element, in accordance with some exemplary embodiments of the invention.

Reference is now made to FIG. 12A, showing flat filter element 1260 removably held within a recess 1280, according to some exemplary embodiments of the invention. Filter element 1260 is secured on at least one side by an insert element 1270.

In some embodiments, filter element 1260 of sub-assembly 1200A is held within a recess 1280 of cap housing 1235A by a retaining insert element 1270. In some embodiments, insert element 1270 is in turn held in position by, for example, hollows 1271 which are occupied by retaining flanges 1284. In some embodiments, a portion of cap housing 1235A separates between recess 1280 and a face of cap housing 1235A weldable to a collection pouch. In some embodiments, a distance of said separation is, for example, 0.3-0.6 mm, 0.4-0.7 mm, 1-2 mm, 2-4 mm, 3-7 mm, any distance in between, or a larger or smaller distance.

The firm sides of the resulting aperture for holding the filter element are potentially well-suited to the use of a replaceable filter. A potential advantage of a firm-sided filter holder is firmer holding of the filter element in place. A potential advantage of a filter element positioned not between a cap housing and a portion of a collection pouch is that a fully annular welding tool can be used in attaching the pouch portion to the cap housing. A potential advantage of a recess separated from a face intended for welding is reduced risk of damage to the filter element caused by heat produced during welding.

Figure 12B:
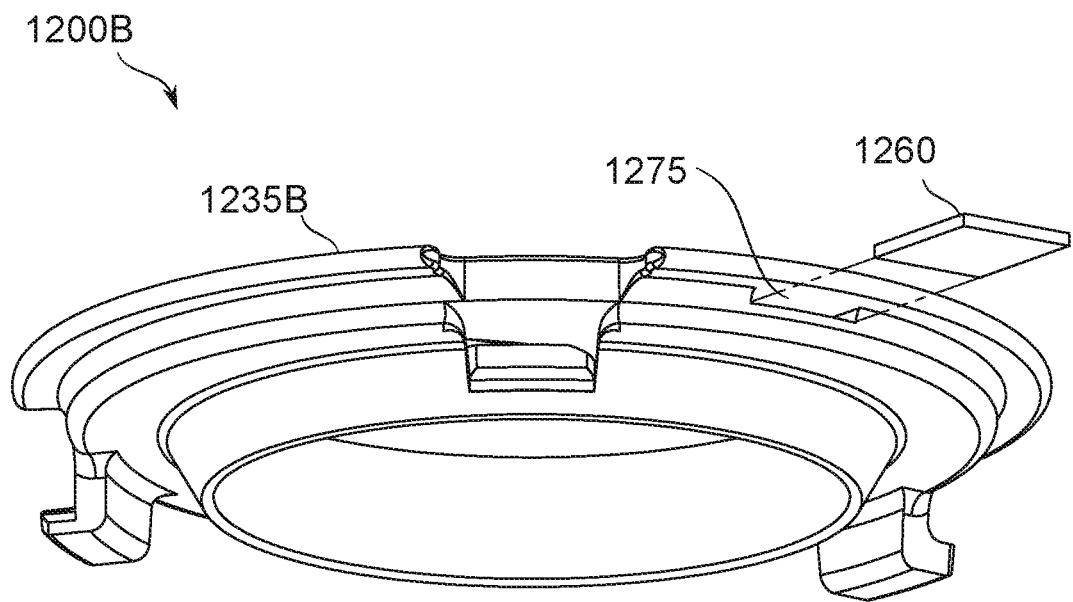
FIG. 12B schematically illustrates a perspective view of a cap housing with a flat filter element adapted to be held within an aperture of the cap housing, in accordance with some exemplary embodiments of the invention.

Reference is now made to FIG. 12B. In the figure, cap sub-assembly 1200B of an ostomy appliance, according to some exemplary embodiments of the invention. Cap sub-assembly 1200B comprises a flat filter element 1260 adapted to be removably held within an aperture 1275 of cap housing 1235B.

In some embodiments of the invention, filter element 1260 is held within an aperture 1275 of a cap housing 1235B. The firm sides of the holder for the filter element are potentially well-suited to the use of a replaceable filter. The one-piece construction of the filter holder is potentially of particular durability. One-piece construction of the filter holder is potentially cheaper for production, as fewer components are produced and less assembly is required.

Figure 12C:
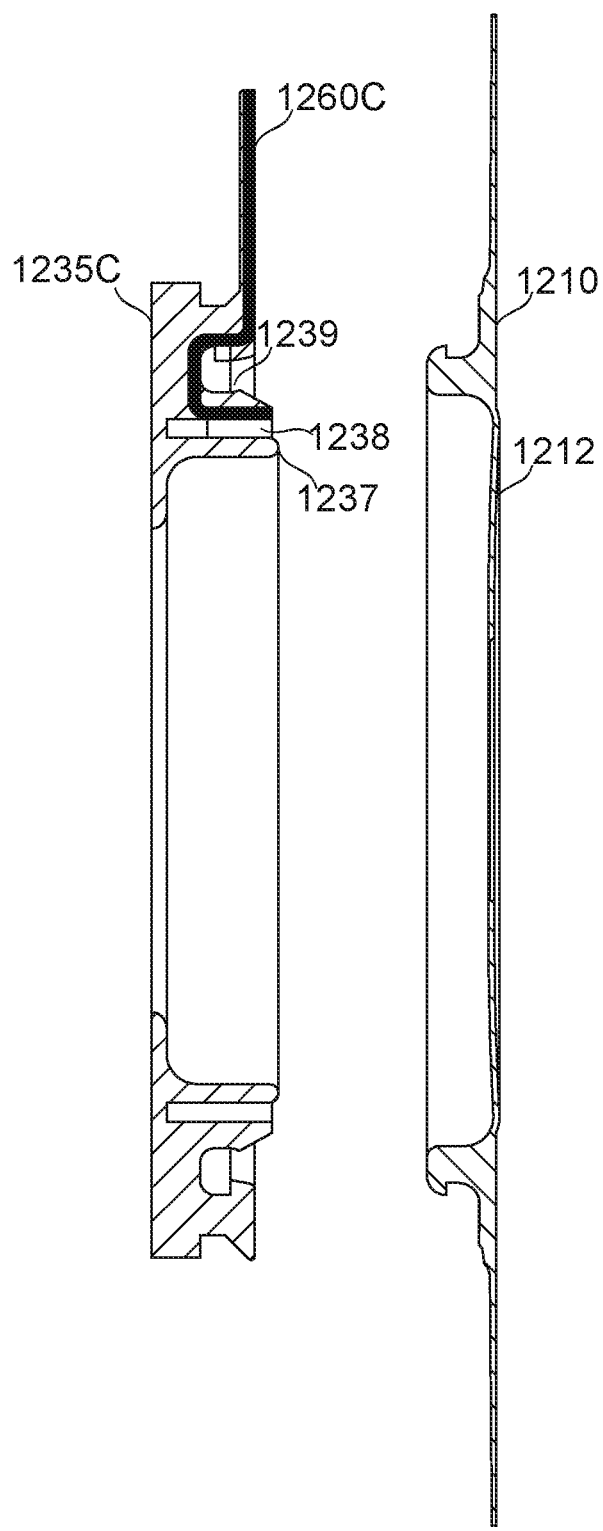
FIG. 12C schematically illustrates a sectional view of an ostomy appliance housing and wafer comprising a flat filter element embedded in the housing by overmolding, in accordance with some exemplary embodiments of the invention.

Reference is now made to FIG. 12C, which illustrates a filter embedded in a housing 1235C by overmolding, according to some exemplary embodiments of the invention.

In some embodiments of the invention, filter element 1260C is embedded within a cap or adaptor housing 1235C by an overmolding technique. In some embodiments, filter element 1260C is placed in the mold used for the manufacture of housing 1235C, and the material of the housing is molded around it.

Potentially, this construction provides an advantage for manufacture by removing an assembly step of manufacture. Potentially, the molded fit between filter and housing allows more reliable resistance to the outflow of gasses around the filter body edges. In some embodiments, for example, inner ring 1237 (or another secondary sealing element) presses against a floor 1212 of wafer 1210 when housing 1235C is assembled to the wafer 1210. Optionally, the contact is sufficient to resist the passage of liquid and/or solid waste, but loose enough to permit the passage of gas. Optionally, an aperture for gas passage is provided. Gas reaching secondary lumen 1238 can thus exit through a protected input surface of filter 1260C.

In some embodiments, molded incorporation allows a filter body shape which does not need a width profile suitable to be pushed through an enclosing aperture. Optionally, the filter 1260C is bent, either during molding, or by manufacturing steps to change the filter shape (for example, heat forming) before overmolding. Potentially, a non-planar configuration increases the filtering length of the filter. Potentially, a non-planar configuration allows the filter to be shaped to avoid other structures of the ostomy appliance, such as attachment fitting 1239.

Manual Gas Release

Figure 13A:
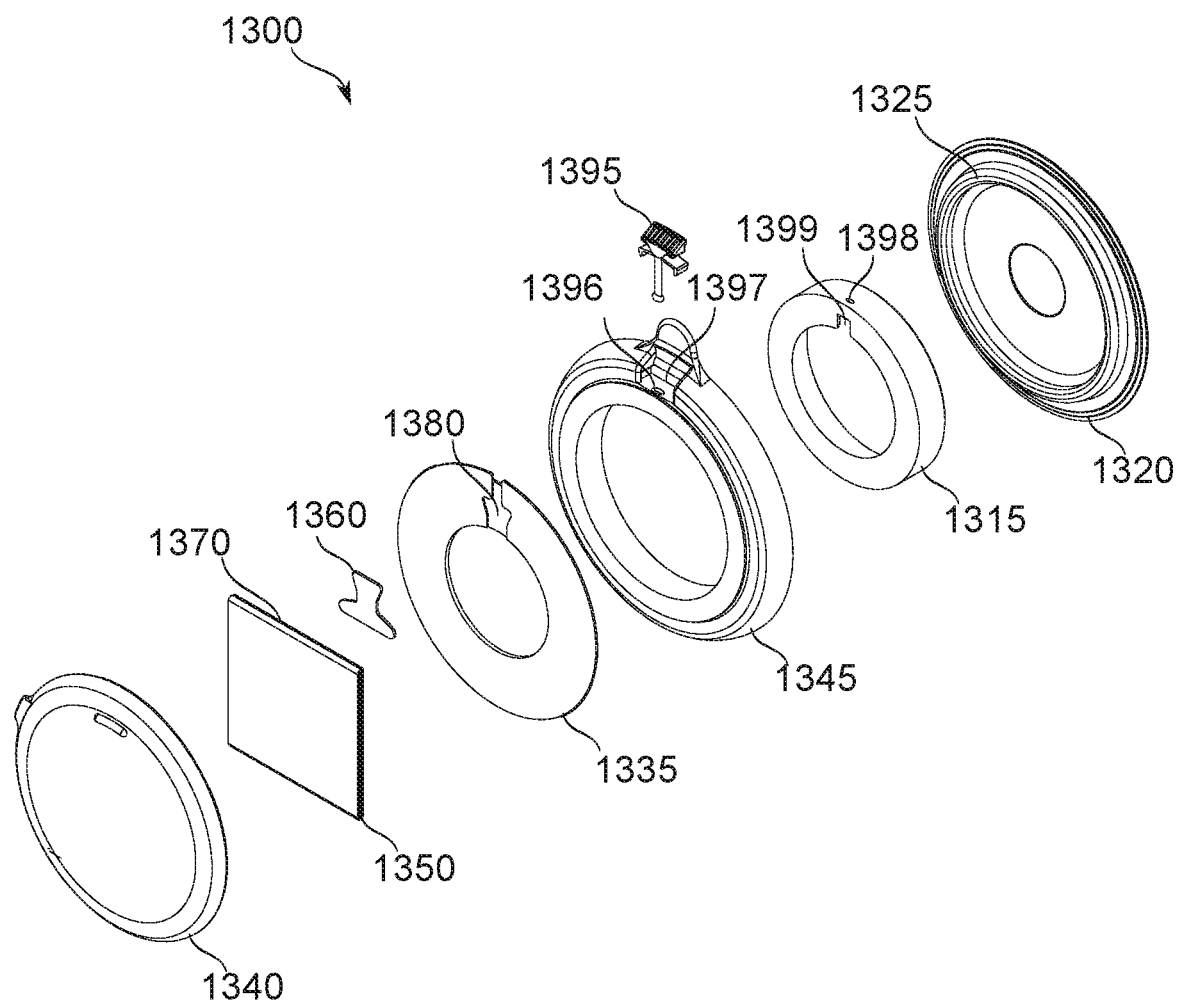
FIG. 13A schematically illustrates an exploded perspective view of an ostomy appliance stack comprising a gas filter and a manual gas release valve stem, in accordance with some exemplary embodiments of the invention.
Figure 13B:
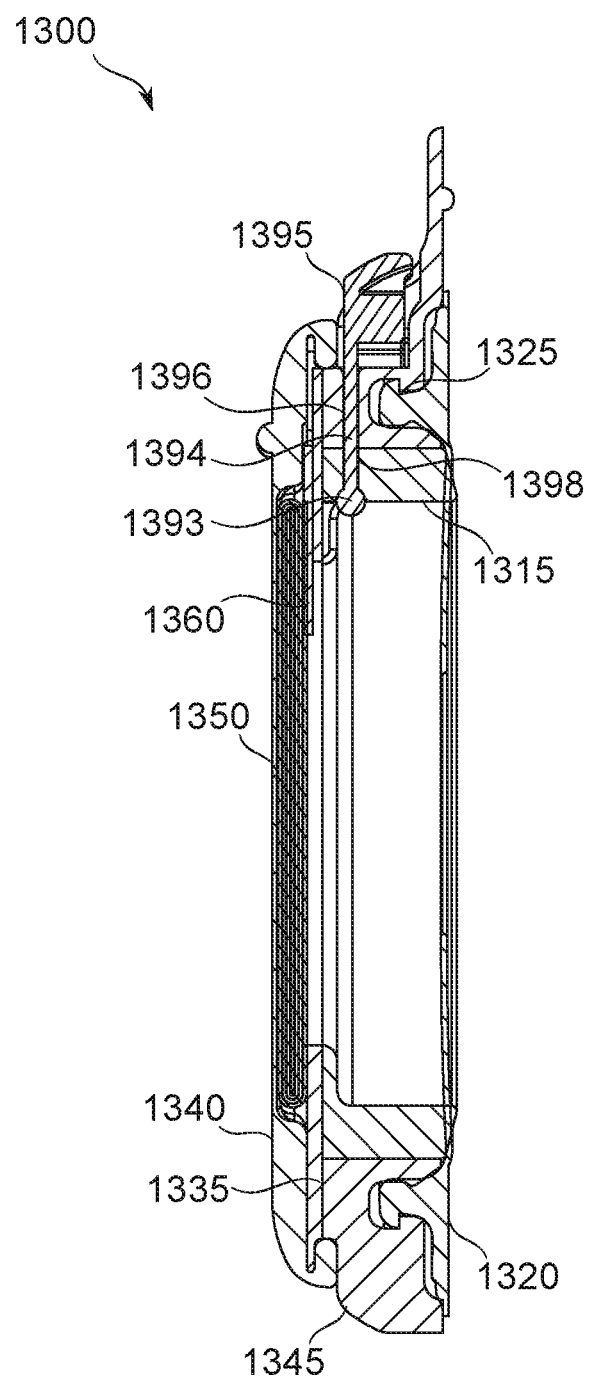
FIG. 13B schematically illustrates a sectional view of the ostomy appliance stack of FIG. 13A, in accordance with some exemplary embodiments of the invention.
Figure 13C:
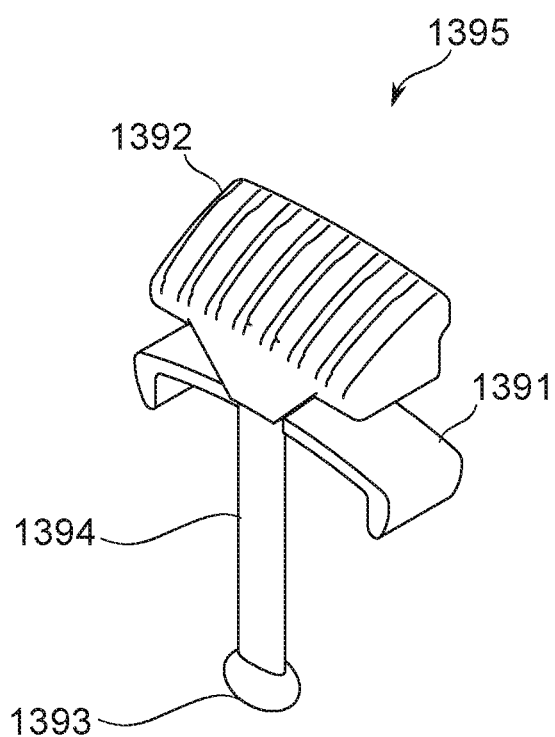
FIG. 13C shows a magnified perspective view of the manual gas release valve stem of FIG. 13A, in accordance with some exemplary embodiments of the invention.

Reference is now made to FIGS. 13A-13C. FIG. 13A shows an ostomy appliance stack 1300 comprising a transmural gas release valve stem 1395, according to some exemplary embodiments of the invention. FIG. 13B illustrates a sectional view of the ostomy appliance stack 1300 of FIG. 13A, according to some exemplary embodiments of the invention. FIG. 13C shows a magnified perspective view of the manual gas release valve stem 1395 of FIG. 13A, according to some exemplary embodiments of the invention.

A transmural valve potentially provides a manually actuatable alternative and/or adjunct to filtered gas release. For example, in the case of a sudden gas bolus, the valve can be activated to reduce gas pressure faster than the filter element alone. A transmural valve potentially provides potential means for testing whether a felt pressure is due to solid/liquid waste, or to gas, by brief opening to determine if gas is released. In some embodiments, a transmural valve comprises a safety release mechanism for gaseous overpressure. Optionally, loss of gas release function due to a blocked filter can be worked around by activation of the valve.

In some embodiments of the invention, ostomy appliance 1300 comprises an actuatable valve for manual gas release. In some embodiments, the manually actuatable valve comprises a shell 1345, a stem part 1395, and/or a secondary sealing element 1315. In some embodiments, a filter element 1360 for passive gas release is provided along with the manually actuatable valve.

In some embodiments of the invention, shell 1345 comprises a stem-receiving hole 1396 and a stem part holding region 1397. In some embodiments, sealing element 1315 comprises a stem receiving hole 1398 and a stem part holding region 1399.

In some embodiments, stem part 1395 assembles to the ostomy appliance with a rigid stem 1394 of the stem part 1395 inserted through hole 1396. In some embodiments, stem 1394 inserts through hole 1398. In some embodiments, stem end 1393 comprises an expanded region for pressing an inner aperture of hole 1398 to seal it. In some embodiments of the invention, the expanded region of stem end 1393 inserts partially or completely into hole 1398. In some embodiments, stem end 1393 is tapered (for example, conically), with the narrow end oriented toward the hole 1398. In some embodiments, hole 1398 is tapered to receive part or all of stem end 1393. Optionally the main body of stem 1394 is a tether, for example a string. The tether optionally provides a link sized to tension between an internal sealing body 1393 and an external control such as push button 1392. In FIG. 15E, for example, stem member 1591A comprises a string.

In some embodiments, stem part 1395 comprises a spring 1391, which is, for example, a leaf spring or a coil spring. In some embodiments, spring 1391 is integrally formed with stem part 1395. Integral formation provides the potential advantage of greater simplicity and/or lowered cost of manufacture compared to embodiments where spring and stem part are separate components. In some embodiments, spring 1391 presses against a portion the stem part holding region 1397 of the shell 1345. The pressing pulls stem end 1393 up into the aperture of hole 1398 and maintains sealing.

In some embodiments, button 1392 is actuatable to counteract spring 1391 (or another tensioner or compressor), pushing stem end 1393 away from hole 1398. The pushing breaks the gas seal.

In some embodiments, stem 1394 fits one or both of holes 1397, 1399 closely, to resist solid/liquid waste leakage when the gas seal is broken. The clearance is, for example, 0.01-0.03 mm, 0.02-0.08 mm, 0.07-0.11 mm, 0.1-0.15 mm, a clearance in between, or a greater or lesser clearance.

A secondary sealing element 1315 is provided in some embodiments, for example, to exclude waste from accumulating external to the stoma and/or from contact with skin. In some embodiments, exclusion is by sealing as such, for example, by compression against one or more internal surfaces of an ostomy appliance. In some embodiments, exclusion is by occupying volume around the stoma, such that waste material from the stoma is prevented from accumulating outside the stoma. In some embodiments, secondary sealing element 1315 performs its functions without pressing on the stoma. In some embodiments, secondary sealing element 1315 comprises a flexible material, for example, a thermoplastic elastomer (TPE) or a silicone rubber. The durometer of the material is, for example, in the range of 30-80 Shore A. In some embodiments, secondary sealing element 1315 is a highly elastic material. Such material is, for example, silicone rubber of durometer ranging from 1-30 Shore A, 2-20 Shore A, 2-15 Shore A, 3-10 Shore A, or 3-8 Shore A.

Potentially, the softness of sealing element 1315 assists in forming a seal with stem part 1395. In some embodiments, sealing element 1315 additionally or alternatively restricts the access of stomal discharge to regions of the ostomy wafer 1320 and/or shell 1345. The restriction potentially decreases leakage through outer seals, for example, the seal at 1325 between the ostomy wafer 1320 and ostomy appliance shell 1345. Potentially, the restriction decreases leakage of stomal discharge to the underside of wafer 1320, which can cause tissue irritation and/or loosening of stomal wafer attachment. In some embodiments, sealing element 1315 reduces the accumulation of waste inside the ostomy appliance by occupying internal volume of the ostomy appliance.

In some embodiments of the invention, shell 1345 comprises a flexible material such as TPE or silicone rubber. The flexible material has a durometer, for example, in the range of 30-80 Shore A. In some embodiments, shell 1345 comprises a rigid or semi-rigid material, such as polyethylene or polypropylene. In some embodiments of the invention, shell 1345 and/or secondary sealing element 1315 are sufficiently flexible for a simple method of valve manufacture. In this manufacture, stem 1394, including its expanded region, is pressed through holes 1396 and/or 1398 from the outside to assemble the valve.

Figure 15A:
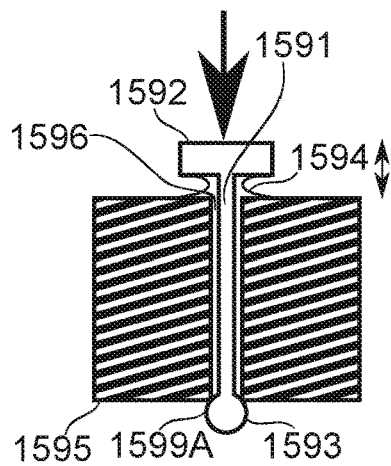
FIGS. 15A-15J schematically illustrate configurations of gas release valves, in accordance with some exemplary embodiments of the invention.
Figure 15B:
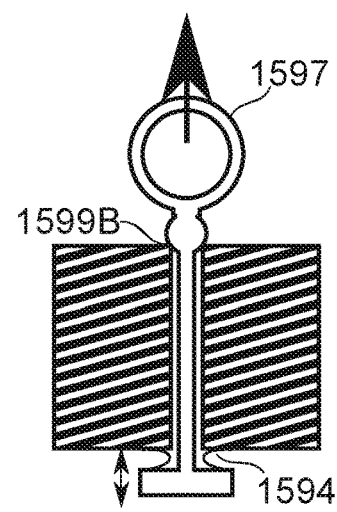
Figure 15C:
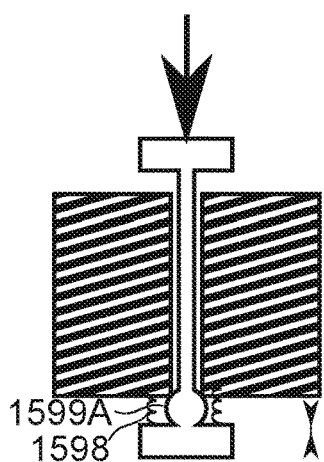
Figure 15D:
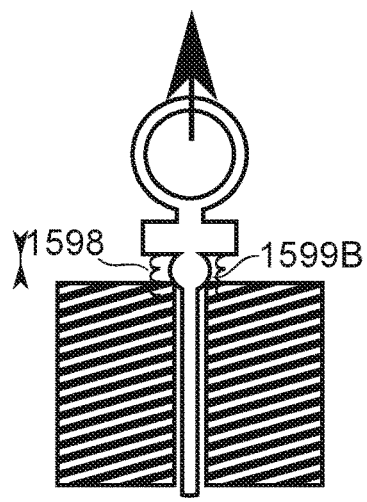
Figure 15E:
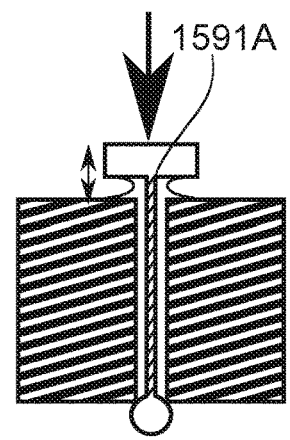
Figure 15F:
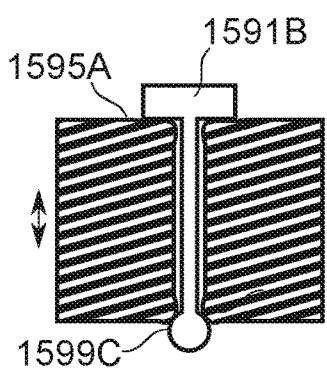
Figure 15G:
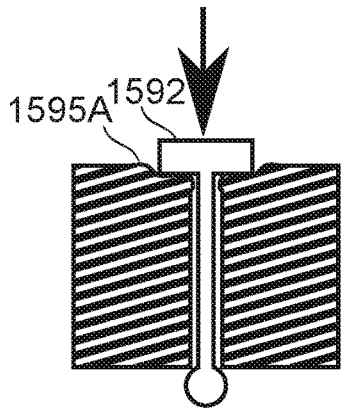
Figure 15H:
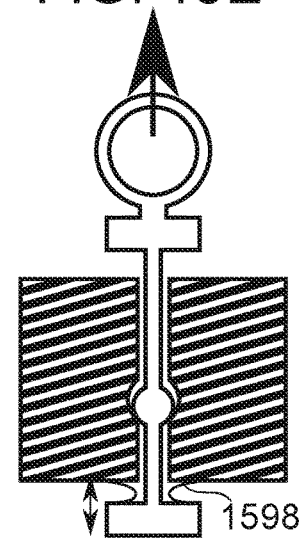
Figure 15I:
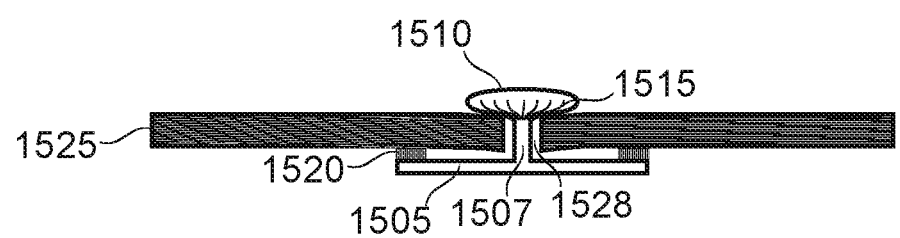
Figure 15J:
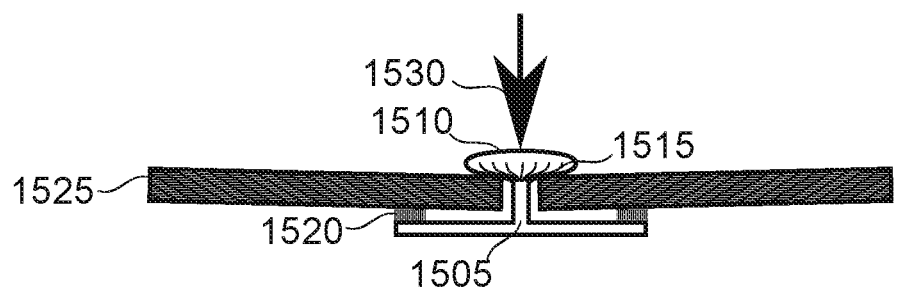

Reference is now made to FIGS. 15A-15J, which show a variety of transmural valve configurations, according to some exemplary embodiments of the invention. FIG. 15A illustrates an exemplary valve with components disposed similarly with respect to the ostomy appliance wall 1595 as in the exemplary valve illustrated in FIGS. 13A-13C. Wall 1595 comprises the shell and/or a sealing element of an ostomy appliance, according to the embodiment. Button 1592 and spring 1594 are outside wall 1595. Stem 1591 penetrates wall 1595 through aperture 1596, and stopper 1593 and sealing region 1599A are inside the wall 1595. In FIGS. 15A-15H, the large arrows represent directions of manual activation force. Small double-headed arrows represent directions of force exerted on components of the valve at the level indicated.

In some embodiments (FIGS. 15B, 15D), stopper 1593 is on the exterior of ostomy appliance wall 1595. To activate, a spring 1594, 1598 or other force urges stopper 1593 to a sealing region 1599B around aperture 1596. Optionally, spring 1594, 1598 (FIGS. 15B, 15C) is disposed in the interior of ostomy appliance wall 1595 to pull stopper 1593 toward sealing region 1599B, 1599A. Optionally, closure of sealing region 1599A, 1599B is overcome by pulling against the sealing force. In some embodiments, a handle 1597 for pulling to release pressure is provided in place of button 1592.

In some embodiments (FIGS. 15C, 15D), spring 1598 and stopper 1593 are both on the interior or both on the exterior the appliance wall 1595. In some embodiments, spring 1598 is anchored to the wall 1595 and to the valve stem assembly. The anchoring is such that the spring is disposed to pull stopper 1593 to a sealing region 1599A, 1599B unless another force is applied.

In some embodiments of the invention (FIG. 15H), a sufficient pressure from within the device displaces stopper 1593 from its sealing position, allowing gas release. Optionally, the sufficient pressure is selected as a safety and/or comfort release threshold. According to the embodiment, the sufficient pressure is, for example, 45-55 mmHg, 55-65 mmHg, 63-78 mmHg, 75-90 mmHg, 80-105 mmHg, larger, or smaller. In some embodiments, manual operation of this pressure release valve is also possible, for example, by pulling on handle 1597. Optionally, other embodiments of the invention (exemplified, for example, in FIGS. 15B and 15D) are configured to allow gas release above a predetermined pressure threshold.

In some embodiments of the invention (FIGS. 15F-15G), the shape and/or size of stem assembly 1591B compresses an elastic portion of appliance wall 1595A for sealing. For example, stem assembly 1591B is optionally formed with a shaft slightly too short to reach the end of an aperture 1596 it inserts into. To reach the end, force is applied to compress the appliance wall 1595A and/or elastically extend the shaft. Upon insertion, compressive forces between the ends of stem assembly 1591B and the wall 1595A create a seal, for example at 1599C. Pressing on button 1592 breaks the seal.

In some embodiments of the invention (FIGS. 15I-15J), sealing force is provided by an annular elastic sealing element 1520. The sealing element 1520 is urged by a portion of a stem assembly 1505 to press against an ostomy appliance wall 1525. Optionally, the wall is a proximal (front) wall of an ostomy appliance, for example a portion of a cover or cap. In some embodiments, the stem 1507 of stem assembly 1505 passes through wall 1525 at aperture 1528. The stem 1507 is anchored on an exterior surface of wall 1525 by a control member 1510 wide enough to resist passing through aperture 1528. In some embodiments, upon an inward force 1530 being applied to control member 1510, wall 1525 deflects. Deflection breaks the seal between sealing element 1520 and wall 1525 so that gas can exit the appliance through aperture 1528. In some embodiments, the under-surface 1515 of control member 1510 is shaped to avoid seal formation to wall 1525 when control member 1510 is activated. Optionally, sealing element 1520 comprises a filter element body, allowing continuous gas release even if the valve mechanism is in a closed position. Optionally, stoppers in other embodiments of the invention (for example, FIGS. 15A-15H) are permeable to gas (for example, comprise filter material), such that opening a valve comprises changing from a relatively slow rate of gas release to a faster one.

Returning to FIGS. 13A-13C, optional features of the ostomy appliance include filter element 1360, supported between a disc 1335 and an ostomy waste collection pouch 1350. In some embodiments, disc 1335 partially houses the filter element as a housing does in some other embodiments (for example, housings 135, 335, 435). In some embodiments, a region 1370 of ostomy pouch 1350 partially houses filter element 1360. In some embodiments of the invention, filter element housing region 1380 of disc 1335 comprises a recess. In some embodiments, filter element housing region 1380 is flat. In some embodiments, material of the filter element 1360 comprises at least a portion of the aperture sealed by a valve member. Optionally, the valve member is operable to deform a portion of the filter element to permit gas release bypassing the filter.

Housing of a filter element comprises different aspects, alone or in combination. One aspect is holding the filter element in place. Another is sealing against the filter element by pressure and/or attachment to prevent gasses from bypassing the filter element body. Another is straining waste input to the filter element. Yet another aspect is sealing against the intrusion of solid and/or liquid to the filter element.

In some embodiments of the invention, ostomy appliance 1300 comprises a cover 1340 for restraining waste collection pouch 1350 and/or preventing deployment during wear. In some embodiments, ostomy wafer 1320 comprises an attachment mechanism 1325, for example a flange, which shell 1345 is adapted to attach to.

Figure 16A:
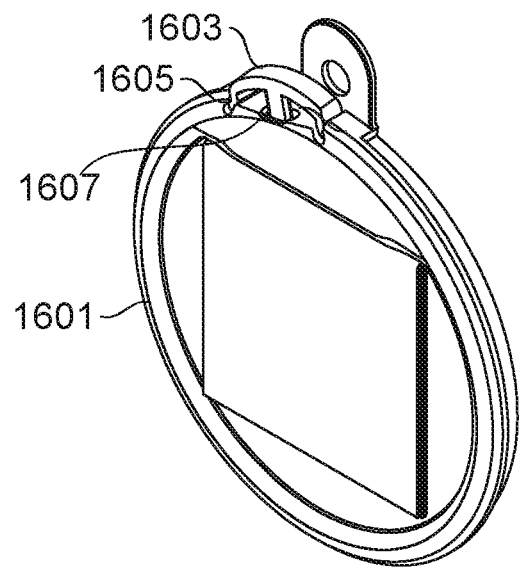
FIGS. 16A-16B schematically illustrate a manual gas release valve, in accordance with some exemplary embodiments of the invention.
Figure 16B:
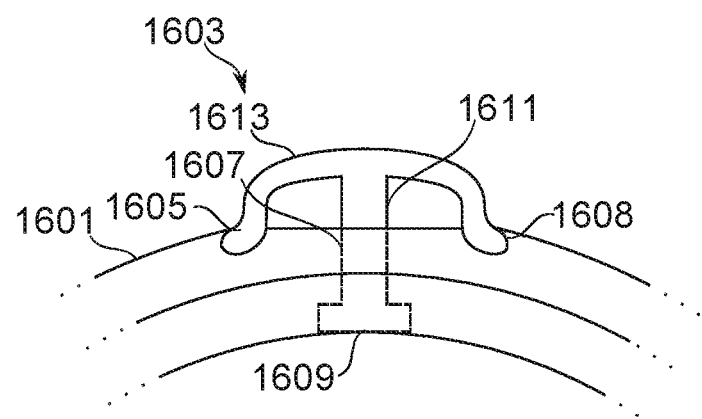
Figure 16C:
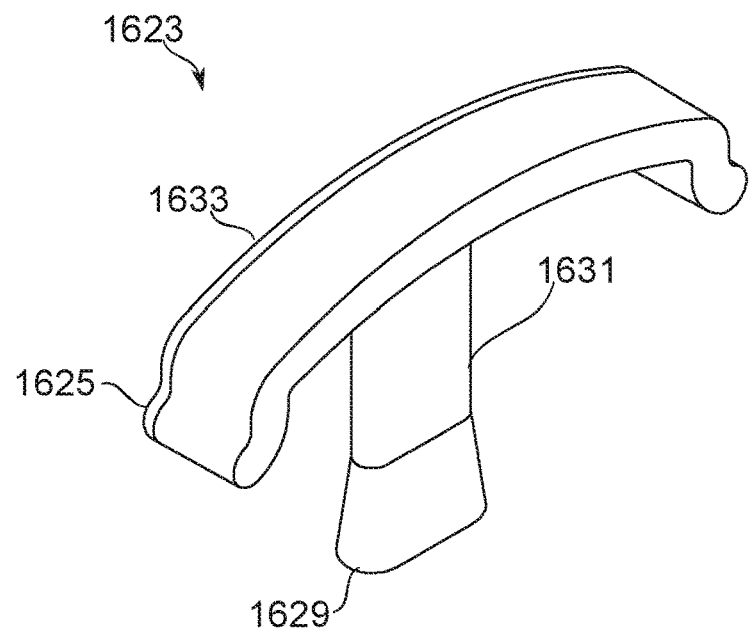
FIGS. 16C-16D schematically illustrate a manual gas release valve, in accordance with some exemplary embodiments of the invention.
Figure 16D:
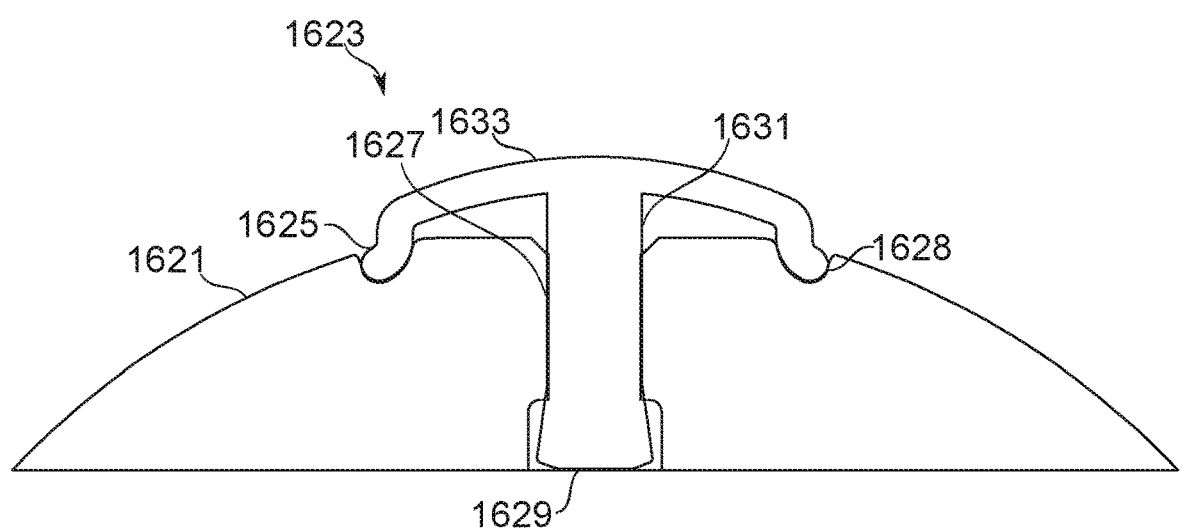

Reference is now made to FIGS. 16A-16B, which schematically illustrate a manual gas release valve, in accordance with some exemplary embodiments of the invention. Reference is also made to FIGS. 16C-16D, which schematically illustrate another manual gas release valve, in accordance with some exemplary embodiments of the invention.

In some embodiments of the invention, valve stem end 1629 comprises a flared, or reverse-tapered end. Optionally, the taper extends into lumen 1627, such that a degree of sealing is controlled by the amount by which the flared region presses against the lumen wall. A potential advantage of flared valve stem end 1629 is that the rate of gas release is controllable by the size of the gap opened as valve member 1632 is displaced downward. Potentially, this also allows control of effluent from the valve, as the size of the gap can be modulated, for example, to allow the escape of gas, without the escape of solid or liquid material.

In some embodiments, a blunt-tipped valve stem end 1609 is provided. A valve comprising a blunt stem end 1609 is relatively insensitive to the amount of displacement it receives, potentially giving an "all or none" response to activation. In exchange for the loss of control, a potential advantage of this design is a clearer indication (for example, by a release noise, and/or an odor) when pressure is sufficient to achieve valve activation.

In some embodiments, gas release valve member 1603, 1623 is insertable into a lumen 1607, 1627 of the body 1601, 1621 of an ostomy appliance component. In some embodiments, valve member 1603, 1623 comprises one or more anchor elements 1605, 1625 insertable into receiving apertures 1608, 1628 in body 1601, 1621. The receiving apertures 1608, 1621 are, for example, molded or cut into body 1601, 1621. In some embodiments of the invention, valve member 1603 1623 comprises a control pressure-receiving region 1613, 1633. In some embodiments, control pressure-receiving region 1613, 1633 comprises an elastic region which acts as a return spring, keeping stem end 1609, 1629 normally pressed into place against an aperture of lumen 1607, 1627 to seal it. Optionally, pressing on pressure-receiving region 1613, 1623 (for example, with a finger) displaces stem 1611, 1621, releasing stem end 1609, 1629 from being pulled against an internal aperture of lumen 1607, 1627.

In some embodiments of the invention, valve member 1603, 1623 is formed from a single molded piece which integrates functions of anchor 1605, 1625 pressure-receiving region 1613, 1623 (including return-spring properties thereof), stem 1611, 1621, and stem end 1609, 1629. The molded piece is formed, for example, of polypropylene, polyethylene, or another polymer resin. In some embodiments of the invention, the material surrounding body lumen 1607, 1627 comprises a material which is sufficiently flexible to stretch, allowing valve stem end 1609, 1629 to be inserted therepast, even though stem end 1609, 1629 is larger than the relaxed size of the lumen 1607, 1627.

It is a potential advantage for valve functions of anchoring, tensioning, sealing, and/or control to be integrated into a part manufacturable as a single unit, for example, for reduction of the cost and/or complexity of device manufacture.

Figure 14A:
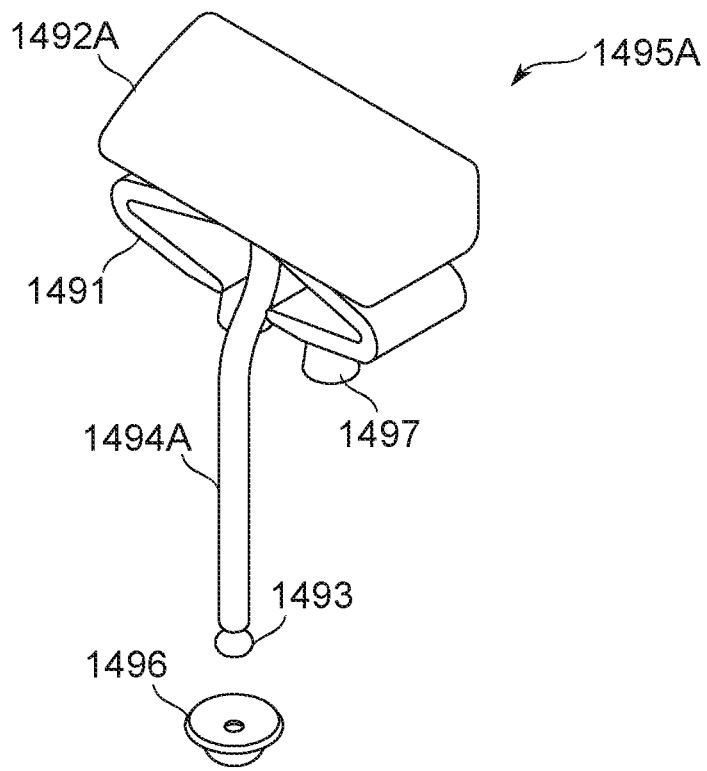
FIG. 14A schematically illustrates a perspective view of a gas release valve stem part, in accordance with some exemplary embodiments of the invention.
Figure 14B:
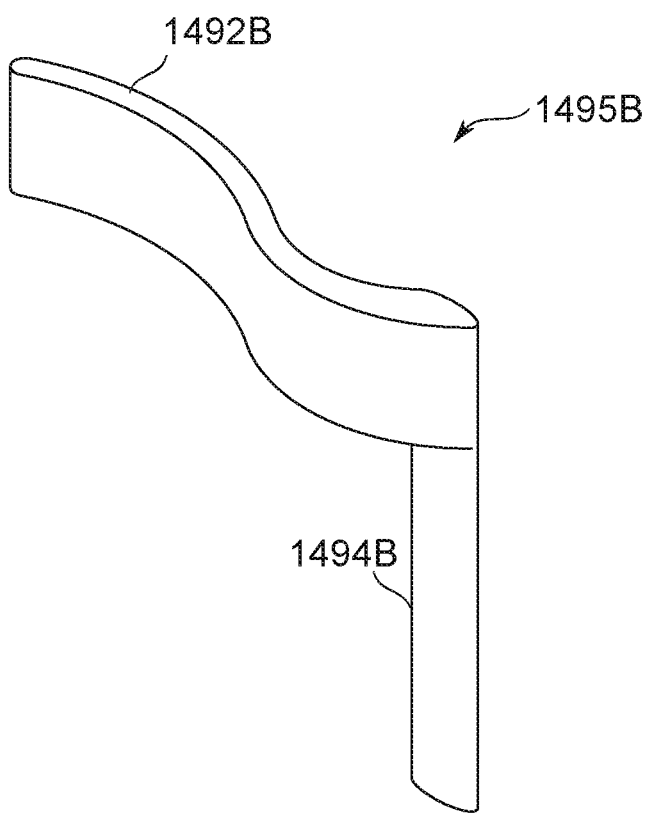
FIG. 14B schematically illustrates a perspective view of a gas release valve stem part, in accordance with some exemplary embodiments of the invention.

Reference is now made to FIGS. 14A-14B. FIG. 14A shows a gas release valve stem part 1495A with a soft sealing tip, according to some exemplary embodiments of the invention. FIG. 14B shows a gas release valve stem part 1495B rotatable to seal or open a gas release aperture, according to some exemplary embodiments of the invention.

In some embodiments, valve stem part 1495A inserts into and seals a hole in a component of an ostomy appliance (appliance 1300, for example). In some embodiments, valve stem part 1495A comprises a stem 1394A, with a stem end 1493 adapted to fit with a stem end cup 1496. In some embodiments, stem end cup 1496 comprises a flexible material such as a thermoplastic elastomer or silicone rubber. In some embodiments, stem end cup 1496 is adapted to seal against the exit of gasses through the hole in which valve stem 1494A fits. A potential advantage of a flexible stem end cup 1496 is to allow closer form fitting against the aperture of a hole 1398. A flexible stem cup 1496 can potentially seal against a hard surface; for example, an inner surface of shell 1345 in embodiments where a secondary sealing element is not used.

In some embodiments of the invention, button 1492A is pressed to deform elastic spring element 1491, breaking the seal made by stem end cup 1496. In some embodiments of the invention, spring element 1492 has a doubled-over shape. In some embodiments, at least one securing pin 1497 extending from the spring is received by a complementary hole in, for example, shell 1345. A potential advantage of securing pin 1497 is to help anchor valve stem part 1495 in position.

In some embodiments of the invention, stem end cup 1496 is constructed to collapse under a sufficient outward pressure from the stoma. In some embodiments, collapsing breaks the seal which cup 1496 makes with another part of the stomal appliance, allowing gas to escape outward. A potential advantage of this feature is to provide a safety valve for gas release which operates both automatically upon a sufficient pressure threshold being passed, and operates manually as described above. The pressure causing collapse is, for example, 47-52 mmHg, 55-65 mmHg, 60-75 mmHg, 70-85 mmHg, 80-105 mmHg, or a greater or smaller pressure. Exemplary ranges between a minimum and maximum pressure causing collapse are 5 mmHg, 10 mmHg, 25 mmHg, any range in between, or a greater or smaller range. In some embodiments, a stemmed valve for automatic pressure release is provided separately from a manual pressure release. In some embodiments, another pressure-sensitive means for automatically breaking the seal of a stemmed valve is provided. For example, a stem end 1393 is sized to be pressed past a sealing portion of a sealing element 1315 under a sufficient outward pressure.

In some embodiments of the invention, stem 1494B of valve stem part 1495B is non-circular in cross-section, for example, lenticular. In some embodiments, one or more of the holes into which stem 1494B fits (for example, hole 1398) has a complementary and fitting cross-section. In some embodiments, release of gas is actuatable by turning stem 1494B in place. The resulting deformation of hole 1398 creates a gap which allows gas to escape. In some embodiments, a lever 1492B is attached to the top of valve stem part 1495B, which projects horizontally from the shaft of stem 1494B. Pressing on the lever potentially rotates the stem shaft 1494B, opening a channel for gas release.

Pouch-Attached Filter Elements

Reference is now made to FIG. 17A, which schematically shows a filter element 2103 positioned to vent through the material of an ostomy pouch 2100, according to some exemplary embodiments of the invention.

In some embodiments, a filter element 2013 is attached to an ostomy pouch 2100, at a position selected to allow ventilation therethrough even when the pouch is folded into a collapsed configuration. In some embodiments, a ventilation outlet 2105 comprises one or more slits in the pouch material, over which the filter element 2013 is sealed. In some embodiments, the position is defined by one or more of the following: (1) a side of the pouch toward or away from an ostomate, (2) the choice of a particular sub-panel 2108, and/or, more particularly, choice of a pouch sub-panel 2108 in relation to the sub-panel comprising an inlet aperture to the pouch 2101, and/or (3) a particular position and/or orientation within the selected sub-panel.

In some embodiments of the invention, the ostomy pouch 2100 is permanently attached at inlet 2101 to the housing of another ostomy component for mounting to the stoma. Ostomy components to which an ostomy pouch 2100 is attachable include an ostomy cap, wafer, ostomy appliance adaptor, and/or an aperture of an ostomy device insertable to an ostomy. In some embodiments of the invention, the pouch comprises an integral adaptor for separate attachment to another ostomy component. It is to be understood that ostomy pouch 2100 represents a general ostomy pouch, and is comprised, in some embodiments, of a different aspect ratio, rounded as opposed to sharp corners and/or sides, a different overall outline, and/or a different folding pattern. An ostomy pouch, in some embodiments, holds up to about 750 ml of waste volume, or for example, up to about 250 ml, 400 ml, 500 ml, 600 ml, or another greater, smaller, or intermediate volume of waste.

Reference is now made to FIG. 17B, which schematically shows structural detail of a filter element 2103, according to some exemplary embodiments of the invention.

In some embodiments, a filter element 2103 comprises fixed attachment to a portion of an ostomy pouch, for example, a sub-panel 2108. In some embodiments, attachment is to the inside of the pouch. Optionally, attachment is outside, in which case the "vent" and "inlet" portions of the filter are reversed relative to the body of the element (that is, the filter inlet is at an aperture of the pouch material, and the filter outlet comprises an edge region of the filter body). In some embodiments, portions of the filter element are bonded both inside and outside the pouch membrane material, across an aperture in the membrane material. In some embodiments, one or more surfaces of the filter body 2102 are sealed against the entry of gas by a sealing element 2104. In some embodiments, gas enters only through one or more defined inlet regions 2107. In some embodiments, gas exits through one or more outlets 2105. In some embodiments, the shortest distance between any given inlet 2107 and any given outlet 2105 is configured to ensure a desired level of odor clearance by the material of filter body 2102.

In some embodiments, the body 2102 of filter 2103 is of a construction such as felt, cloth, foam, lattice, or cake. In some embodiments, the body 2102 of gas filter 2013 comprises an odor-absorbing material which filters odorants from outflowing gasses. Additionally or alternatively, the filter adsorbs odorants, catalyzes their breakdown and/or conversion, or otherwise traps them, and/or neutralizes them as an odorant. Potentially, filtered odorants are noxious odorants, for example, fecal odors. According to the embodiment, odor absorption is, for example, by the use of activated charcoal, silica gel, zeolites, and/or carbide-derived carbon. In some embodiments, the filter is preloaded with perfumes and/or odor neutralizing substances, for absorbing gasses passing through the filter to render them less noxious. Potentially, filtering slows the release of gasses so that external concentrations of odorants are less noticeable to the ostomate and/or to others.

Reference is now made to FIGS. 17C-17E, which schematically illustrate positioning of a filter 2103 relative to folded structure of an ostomy pouch 2150, according to some exemplary embodiments of the invention.

In some embodiments, an ostomy pouch 2150 is folded to a package while worn, until a manual or automatic deployment for filling with waste. While worn collapsed, an ostomy pouch 2150, in some embodiments, does not fill with waste, but preserves a continent covering of a stoma. In some embodiments, passive (automatic) flatus evacuation is nevertheless performed, by means, for example, of a filter element 2103. In some embodiments, the filter element 2103 is comprised in the ostomy pouch 2150, in such a way that it functions to vent flatus even while the ostomy pouch 2150 is collapsed. In some embodiments, the structure of the pouch assists the filter venting function, for example by protecting the filter from contamination by waste, and/or controlling the rate of gas flow thereto.

In some embodiments, a nearly folded ostomy pouch 2150 comprises a remaining first flap 2110, and second flap 2112 (for example, a top flap and a bottom flap), foldable over a central panel region attached to a mounting element 2109 to complete the folding of the package. Folding to reach the configuration of FIG. 17C comprises, for example, doubling over of the pouch of FIG. 17A, followed by folding in of "wings" comprising the three panels on either side. A 3×6 panel has some advantages for use with an ostomy, and particularly for use as a folded ostomy bag. One potential advantage is that the aspect ratio is well suited to hanging waste in a relatively long downward-hanging compartment, which assists in the task of removing the pouch without undue risk of waste spilling back out of the inlet aperture. A one-panel upper protrusion potentially allows the pouch to expand while filling, to reduce the risk of blocking-up the inlet with the waste as it enters the bag. From the standpoint of packaging, two full panel-size wings provide enough material to allow the pouch to assume a bulging configuration when full, and also fold neatly into position to provide a clean package profile. Similarly, six panels vertically, once folded in half, also fold neatly in two additional steps to complete the package shape. It is to be understood, nevertheless, that many pouch shapes and folding configurations comprise embodiments of the current invention; the 3×6 panel embodiment show in these drawings is exemplary and not limiting. Not all panels are full sized in some embodiments. The shape of the pouch does not strictly follow the outline the shape and/or boundary orientations of the panels in some embodiments: it may be rounded on corners or sides, cut-off mid panel, or otherwise varied.

In some embodiments of the invention, filter element 2103 is attached to one of the walls of the material comprised in the pouch. As shown, the filter element is attached to the wall nearest to the ostomate in the pouch-deployed configuration, to the panel immediately above the mounting element-attached panel, near the bottom of that panel, but spaced from the panel fold-crease edges by, for example, 2-4 mm, 3-6 mm, 5-10 mm, or a distance in another range having the same, intermediate, larger and/or smaller bounds.

In some embodiments of the invention, folding flap 2110 over (FIG. 17D) results in the filter being brought to the front of the package, and positioned near its top. Optionally, this is done after flap 2112 is folded over. As shown, flap 2112 is folded (optionally) up over flap 2110. The resulting package (FIG. 17E) positions the filter close to a surface of flap 2112 which potentially occludes vent aperture 2105. In some embodiments, the risk of occlusion is reduced by the positioning of the filter 2103 (and thus vent aperture 2105) near the free end of flap 2112. In some embodiments, a crimp region 2120 is formed by the folding over of region 2110. In some embodiments, the crimp comprises an at least partial barrier to the intrusion of solid and/or fluid waste to the pouch compartment comprised in the panel containing the filter 2103. Barrier properties of some embodiments of the crimp region 2120 include, for example, that it comprises a restriction, and that it is located at the top of the pouch package, such that waste must first be pushed upward before it can descend to potentially foul the filter. Stomal gas, in contrast, potentially is free to diffuse into the region of the filter 2103, being relatively unaffected in its movement by the direction of gravity and/or the partial restriction comprised in crimp region 2120.

Figures 18A, 18B:
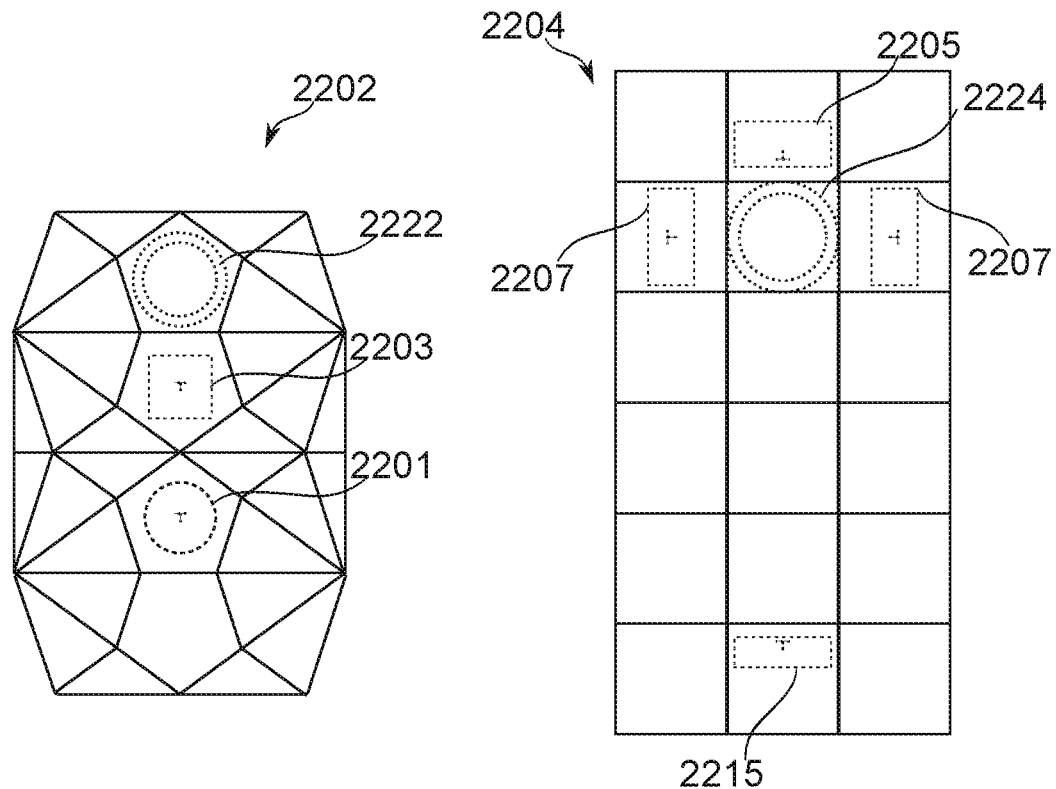
FIGS. 18A-18B show different configurations of filters attached to pouch embodiments, according to some exemplary embodiments of the invention.

Reference is now made to FIGS. 18A-18B, which show different configurations of filters 2201, 2203, 2207, 2205, 2215 attached to pouch embodiments 2202, 2204, according to some exemplary embodiments of the invention.

An ostomy pouch, in some embodiments, is folded into a packaged configuration which comprises, for example, a square, rectangular, pentagonal, hexagonal, or other polygonal shape. FIGS. 18A and 18B indicate fold lines by means of which the ostomy pouch is collapsible from its open state (shown) to a collapsed state, shaped, for example, like one of the pentagons of pouch 2202, or one of the square panels of pouch 2204. In some embodiments, the package, when folded, lies to one side of the inlet aperture sub-panel 2222, 2224.

In some embodiments, a filter element has any desired shape appropriate to the constraints of the panel within which it is placed, for example, round filter element 2201, square filter element 2203, or rectangular filter elements 2205, 2207, 2215. Constraints comprise, for example, being sized and shaped such that crease edges are avoided. Placement within the panel, in some embodiments, is such the filter outlet aperture is away from a region likely to be blocked, and/or such that the filter inlet aperture is raised up relative to potential accumulation of fluid or solid within the collapsed structure of the pouch.

In some embodiments of the invention, the pouch panel in which the filter 2203, 2205, 2207 is placed is chosen to be one crease away from the inlet to the pouch. This allows a potential advantage of separation of flatus from other waste material by the resistance of a crease, without increasing resistance to the point where flatus itself is blocked. Nevertheless, in some embodiments, a filter element is placed two or more creases beyond a pouch inlet (for example, filter elements 2201, 2215). This potentially increases the separating function which helps protect the filter inlet regions. Potentially, it slows the rate at which flatus escapes the filter element 2215, 2201. Potentially, this in turn improves stench control for continuous release, though it may also increase stomal pressure and/or reliance on manual venting. In some embodiments of the invention, the filter flow rate is set to be, no more than 1-10 ml/min, 2-5 ml/min, 3-8 ml/min, or another range of flow rates having the same, intermediate, larger and/or smaller bounds.

The panel, in some embodiments, is above (filter 2205), below (filter 2215), and/or to the side (filter 2207) of the inlet aperture. In some embodiments, a plurality of filter elements is provided, for example, both of the marked side filter elements 2207.

Figures 18C, 18D:
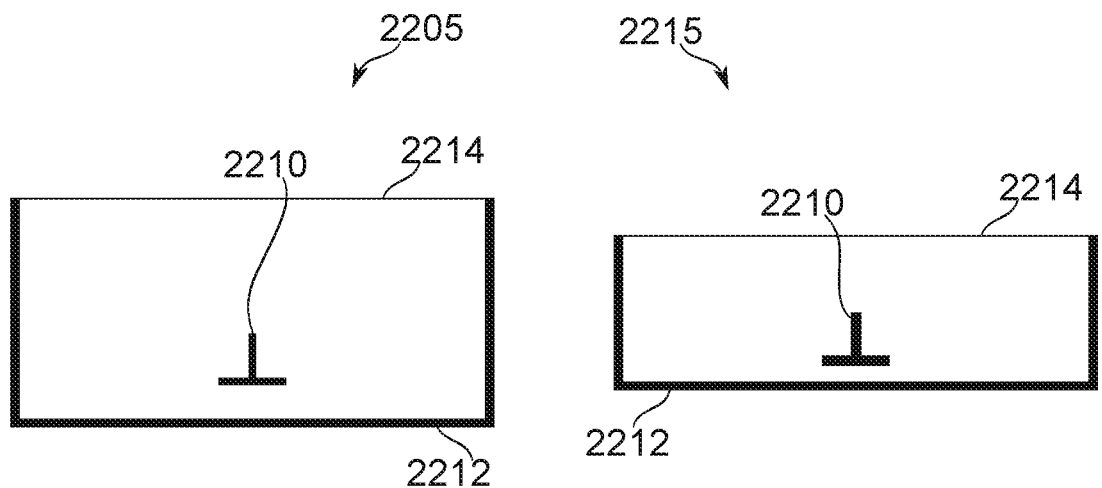
FIGS. 18C-18D show filter elements having at least one side protected from waste contamination by a sealing element, according to some exemplary embodiments of the invention.

Reference is now made to FIGS. 18C-18D, which show filter elements 2205, 2215 having at least one side protected from waste contamination by a sealing element 2212, according to some exemplary embodiments of the invention.

In some embodiments a filter element 2205, 2215 has a preferred orientation conferred by sealing of one or more sides from which waste leakage is deemed most likely to arrive (for example, since that is the direction across which lies the pouch waste inlet). Thus, for example, filter element 2205 is positioned with the long side facing the pouch inlet sealed. The short sides are sealed as well, in some embodiments.

In some embodiments, sealing allows an outlet aperture 2210 to be positioned closer to a sealed side, without shortening the shortest available path from filter intake to filter outlet. In some embodiments, this allows more thorough (if potentially slower) filtering from a given size of filter element. In some embodiments, it allows reduction of the amount of filter material used. A potential advantage of this is cost savings, another potential advantage is reduced effect on pouch package size, and yet another potential advantage is placement of the outlet aperture nearer to the edge of the panel (in a less occluded position, for example), without increasing interference with panel creasing.

Figure 19A:
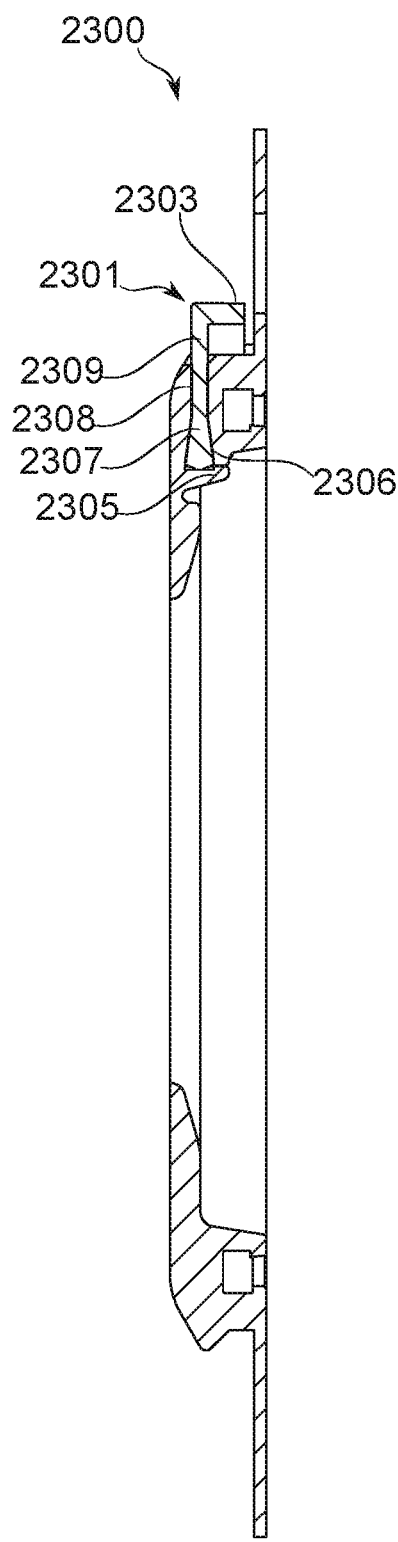
FIGS. 19A-19B show cross-sectional views of an ostomy appliance comprising a flap valve, according to some exemplary embodiments of the invention.
Figure 19B:
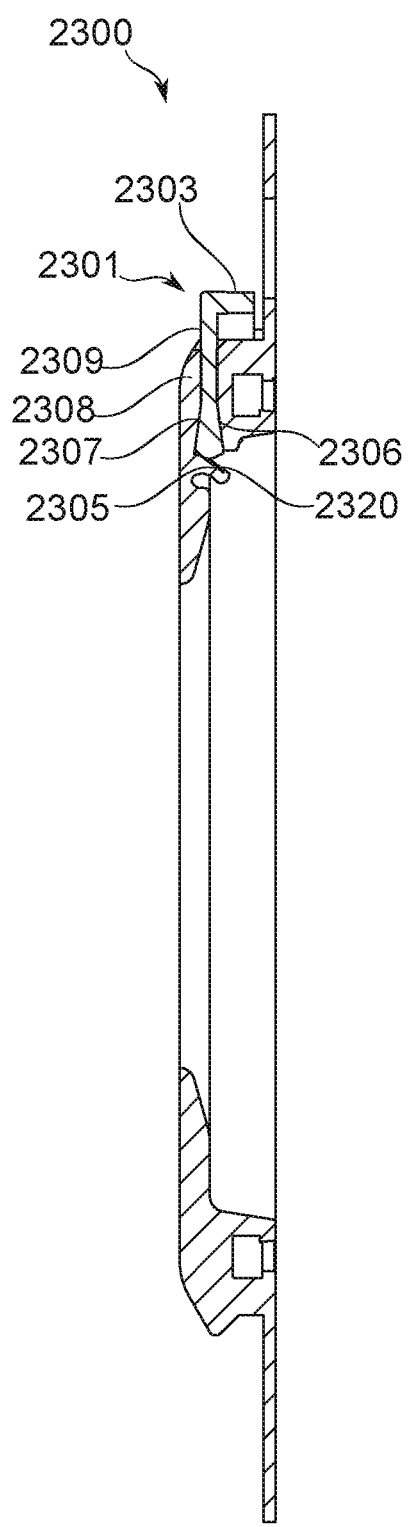

Reference is now made to FIGS. 19A-19B, which show cross-sectional views of an ostomy appliance 2300 comprising a flap valve, according to some exemplary embodiments of the invention.

In some embodiments of the invention, a valve member 2301 is inserted to a lumen 2308 of an ostomy appliance

2300. In some embodiments, a control surface 2303 is located outside the ostomy appliance. A valve stem 2309 passes into lumen 2308, terminating in a pressing end 2307. In some embodiments, pressing end 2307 forms a seal against the wall of lumen 2308. Sealing, in some embodiments of the invention, comprises pressing end 2307 having an inverse taper 2306 (for example, a conical taper growing wider toward the pressing end), such that back pressure from the stoma, and/or force from a spring or other tensioning member tends to jam the tapered region more tightly against the walls of lumen 2308. To open this seal, the valve stem 2309 is advanced in the lumen, opening a gap 2320 between the lumen 2309 and the taper 2306 and/or other surface in contact with the lumen 2309.

In some embodiments of the invention, pressing end 2307 is configured to contact a valve flap 2305 when it is advanced forward in lumen 2308. In some embodiments, pressing downward on control surface 2303 advances pressing end 2307 to push against valve flap 2305. In FIG. 19B, valve flap 2305 is shown deflected due to pressure from pressing end 2307.

In some embodiments of the invention, valve flap 2305 serves to prevent flow into the valve body during wear. In some embodiments, valve flap 2305 is the main or only sealing portion of the valve assembly. In some embodiments, valve flap 2305 operates together with sealing by the valve stem/pressing end 2307, 2309 against lumen 2308.

In some embodiments, valve flap 2305 is comprised of a flexible elastomer (for example, having a Shore A of about 40-60, 50-70, 70-90, or within another range of Shore A values having the same, intermediate, larger and/or smaller bounds). In some embodiments valve flap 2305 is configured to normally press upward against sealing surface 2310. A gap between flap 2305 and sealing surface 2310 opens when pressing member 2307 presses down on it. When released, flap 2305 is sufficiently elastic, in some embodiments, that it returns to its sealing position.

A potential advantage of flap 2305 is to protect the main valve apparatus from contamination by waste, except when the valve is in operation to be opened. Another potential advantage is to provide a higher sealing resistance and/or sealing redundancy to the valve.

Reference is now made to FIGS. 20A-20C, which show views of an ostomy appliance comprising a valve member 1623 protected from waste entering the stomal enclosure area 2001 by a secondary sealing member 2020, 2022 according to some exemplary embodiments of the invention.

In some embodiments of the invention, valve member 1623 crosses between the outside of ostomy component housing 1621 and the stomal enclosure. In some embodiments of the invention, a sealing element 2020, 2022 occupies the space between the stoma itself and the valve member 1623. In some embodiments, the sealing element 2020, 2022 is gas permeable. It is a potential advantage to provide a sealing member to absorb and/or block liquid and/or solid waste before it reaches the vicinity of valve member 2022, 2020, to avoid fouling of the valve, and/or to avoid leakage from the valve aperture across which valve member 1623 extends.

In some embodiments of the invention, sealing element 2020 extends all the way around the stomal enclosure. In some embodiments, sealing element 2022 comprises a gap region 2022, at which a thickness is reduced in order to accommodate the intruding end of valve member 1623 and or valve flap 2305 (for example, during motion to vent) and/or to create a space around the valve member 1623 into which gas can diffuse. Optionally, the foam is soft enough that a special venting gap is not required or used.

In some embodiments of the invention, sealing element 2020, 2022 is a foam element (comprised, for example, of a foamed polymer, such as a soft, polyether-based polyurethane). The foam, in some embodiments, is permeable, such that gas can pass through it to reach the valve member 1623 for venting. In some embodiments, cells of the foamed rubber are made small enough that waste particles entering the foam plug it, impeding the passage of further waste. Cell diameter in some embodiments is, for example, an average diameter of less than 50 µm, 100 µm, 200 µm, 300 µm, or less than another larger, smaller or intermediate size. An exemplary density of the foam is, for example 0.25 kg/m$^3$. In some embodiments, the density is, for example, about 0.10 kg/m$^3$, 0.20 kg/m$^3$, 0.15 kg/m$^3$, 0.30 kg/m$^3$, or another larger, smaller, or intermediate density.

In some embodiments of the invention, the sealing element 2020, 2022 is sized to extend across the stomal chamber (from the distal floor to the proximal end of the chamber), such that it comprises a complete closure in this direction. In some embodiments, the uncompressed foam element 2020, 2022 is sized to be larger than the distal-proximal chamber dimension, such that it is compressed upon installation to ensure a seal. In some embodiments, sealing element 2020, 2022 is attached on at least one side (for example to proximal wall 2011) by adhesive or welding. In some embodiments, attachment and/or positioning is achieved by supplying the proximal component with a flange which is sized to center the sealing element 2020, 2022 in position. Attachment of the sealing element 2020, 2022 to the stoma is a potential advantage to allow removal of a (potentially soiled) sealing element 2020, 2022 from the stomal area along with the proximal component, rather than requiring separate, potentially messy, retrieval.

In some embodiments of the invention, the sealing element 2022 is a partial seal, which extends sufficiently to prevent waste access to the valve member 1623, without extending fully around the stoma itself. In some embodiments of the invention, the sealing element 2020, 2022 acts as a waste sink, absorbing waste that exits the stoma so that it is not free to move around inside the stomal enclosure. In some embodiments, waste is excluded by the sealing element (due to hydrophobicity, and/or small cell size relative). Optionally, the sealing element 2020, 2022 is sized to lie nearby, without putting pressure on the stomal tissue itself. Optionally, the sealing element 2020, 2022 is spaced from the stoma so that it does not touch it. In some embodiments, multiple inner and/or outer diameters of sealing element are provided, allowing an ostomate to choose a size best suited to their own stoma. In some embodiments, the sealing element comprised a series of partially-attached foam rings, which an ostomate tears off to make a suitable size for their stoma.

In some embodiments, the sealing element 2020, 2022 is manufactured by cutting from a foam sheet, for example, by die cutting. Alternatively, the foam is cast into a desired shape.

As used herein, the term "about" refers to within ±10%.

The terms "comprises", "comprising", "includes", "including", "having" and their conjugates mean: "including but not limited to".

The term "consisting of" means: "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

The words "example" and "exemplary" are used herein to mean "serving as an example, instance or illustration". Any embodiment described as an "example or "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features except insofar as such features conflict.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. An ostomy appliance with a gas release valve, comprising:
    a shell configured to be removably attached to an ostomy wafer configured to attach to peristomal skin around a stoma, wherein said shell comprises a lumenal sidewall forming part of an enclosure for a stoma and having a first aperture passing through said sidewall between an inner peripheral edge adjacent said stoma and an outer peripheral edge of said sidewall;
    a pouch attached to said shell;
    a passive filter for release of gas within or adjacent said pouch, said passive filter comprising a second aperture that does not pass through said luminal sidewall, wherein the passive filter allows gas outflow from the stoma to the outside of the ostomy appliance through said second aperture without passing through said first aperture; and
    a valve member comprising a stopper and a control member, wherein said stopper crosses through said first aperture and is configured to block gas outflow through said first aperture, and wherein said control member is operable from an exterior of said ostomy appliance to move said stopper and unblock said first aperture.

2. The ostomy appliance of claim 1, wherein said valve member comprises a connecting member connecting said stopper to said control member across said first aperture.

3. The ostomy appliance of claim 2, wherein said stopper, said control member, and said connecting member are integrally formed.

4. The ostomy appliance of claim 2, wherein said connecting member is elastic, and under tension urges said stopper into said blocking position.

5. The ostomy appliance of claim 1, wherein said lumenal wall is deformed in compression against said stopper in said blocking position.

6. The ostomy appliance of claim 1, further comprising a spring in compression or tension urging said stopper into said blocking position.

7. The ostomy appliance of claim 6, wherein said stopper, said control member, and said spring are integrally formed.

8. The ostomy appliance of claim 1, wherein said stopper comprises a filter body providing a portion of a passageway for gas outflow across said lumenal wall, and said blocking position prevents gas outflow passing around said filter body.

9. The ostomy appliance of claim 1, wherein said gas outflow is blocked only below a predetermined threshold of an interior pressure.

10. The ostomy appliance of claim 9, wherein the interior pressure of said ostomy appliance presses against said stopper to move it from said blocking position above the predetermined threshold of pressure; or
    wherein said predetermined threshold is between 50 mmHg and 100 mmHg.

11. The ostomy appliance of claim 1, wherein said blocking position comprises said stopper being pressed against an interior or exterior surface of said lumenal wall.

12. The ostomy appliance of claim 1, wherein said stopper comprises a member extending through said first aperture, and operation to move said stopper out of said blocking position comprises a rotation.

13. The ostomy appliance of claim 12, wherein said control member comprises an external lever attached to said member extending through said first aperture, and said lever is operable to rotate said member extending through said first aperture of the stopper so that gas is releasable.

14. The ostomy appliance of claim 1, wherein said stopper comprises a region flaring toward one end of said valve member, and said blocking position comprises a narrow end of said flared region being at least partially inserted into said first aperture, forming a seal therewith.

15. The ostomy appliance of claim 1, wherein said stoma is separated from said stopper by a gas-permeable sealing element.

16. The ostomy appliance of claim 15, wherein said sealing element blocks solid and liquid waste from reaching said stopper from said stoma.

17. The ostomy appliance of claim 1, wherein said lumenal wall has a thickness of at least 3 mm through which said valve member extends.

18. The ostomy appliance of claim 1, wherein the pouch is collapsed.

19. The ostomy appliance of claim 18, wherein the pouch comprises the passive filter for release of gas.

* * * * *